United States Patent [19]

Billig et al.

[11] Patent Number: 4,717,775

[45] Date of Patent: Jan. 5, 1988

[54] TRANSITION METAL COMPLEX CATALYZED REACTIONS

[75] Inventors: Ernst Billig; Anthony G. Abatjoglou, both of Charleston; David R. Bryant, South Charleston; Rex E. Murray; John M. Maher, both of Charleston, all of W. Va.

[73] Assignee: Union Carbide Corporation, Danbury, Conn.

[21] Appl. No.: 865,061

[22] Filed: May 20, 1986

Related U.S. Application Data

[63] Continuation-in-part of Ser. No. 685,025, Dec. 28, 1984, Pat. No. 4,599,206, which is a continuation-in-part of Ser. No. 581,352, Feb. 17, 1984, abandoned.

[51] Int. Cl.$^4$ ............................................. C07C 45/50
[52] U.S. Cl. ...................................... 568/454; 556/13
[58] Field of Search ................. 568/454; 252/522 R; 260/439 P, 936; 558/85, 81; 556/404

[56] References Cited

U.S. PATENT DOCUMENTS

| | | | |
|---|---|---|---|
| 3,102,899 | 9/1963 | Cannell | 556/13 |
| 3,152,158 | 10/1964 | Clark | 556/13 |
| 3,213,155 | 8/1965 | Schriesheim et al. | 585/665 |
| 3,219,714 | 11/1965 | Kutepow et al. | 556/13 |
| 3,271,438 | 9/1966 | Cannell | 556/13 |
| 3,271,481 | 9/1966 | Kujawa et al. | 260/960 |
| 3,290,348 | 12/1966 | Mullineaux | 556/13 |
| 3,297,631 | 1/1967 | Bown et al. | 524/117 |
| 3,328,443 | 6/1967 | Clark et al. | 556/13 |
| 3,346,608 | 10/1967 | Kutepow et al. | 551/13 |
| 3,437,720 | 4/1969 | Guttag | 260/927 |
| 3,491,024 | 1/1970 | Kujawa et al. | 252/32.5 |
| 3,527,809 | 1/1981 | Brewester | 568/454 |
| 3,536,748 | 10/1970 | Drinkard et al. | 556/13 |
| 3,631,191 | 12/1971 | Kane et al. | 556/13 |
| 3,647,841 | 3/1972 | Kauder | 556/13 |
| 3,655,832 | 4/1972 | Kauder et al. | 260/930 |
| 3,661,843 | 5/1972 | Hechenbleikner et al. | 556/13 |
| 3,676,554 | 7/1972 | McGusty et al. | 556/13 |
| 3,832,404 | 8/1974 | Allum et al. | 556/13 |
| 3,847,959 | 11/1974 | Shook et al. | 556/13 |
| 3,903,120 | 9/1975 | Shook | 556/13 |
| 3,927,056 | 12/1975 | Gosser | 556/13 |
| 4,094,855 | 6/1978 | Spivack | 524/1 |
| 4,120,882 | 10/1978 | Wilke et al. | 556/13 |
| 4,148,830 | 4/1979 | Pruett | 568/454 |
| 4,196,117 | 4/1980 | Spivack | 524/119 |
| 4,200,591 | 4/1980 | Hignett et al. | 568/454 |
| 4,247,486 | 9/1970 | Pruett | 568/454 |
| 4,252,750 | 2/1981 | Buysch et al. | 260/927 R |
| 4,283,562 | 8/1981 | Billing | 568/454 |
| 4,287,370 | 9/1981 | Harris et al. | 568/454 |
| 4,288,391 | 9/1981 | Spivack | 260/927 R |
| 4,298,541 | 11/1981 | Oswald et al. | 260/429 R |
| 4,318,845 | 3/1982 | Spivack et al. | 524/91 |
| 4,330,678 | 5/1982 | Van Leeuwen et al. | 568/454 |
| 4,351,759 | 9/1982 | Spivack | 524/100 |
| 4,362,830 | 12/1982 | Minagawa et al. | 524/101 |
| 4,374,219 | 2/1983 | Spivack et al. | 524/91 |
| 4,388,476 | 6/1983 | Cooper | 568/451 |
| 4,400,548 | 8/1983 | Abatoglom | 568/454 |
| 4,482,749 | 11/1984 | Dennis et al. | 568/454 |
| 4,496,768 | 1/1985 | Dennis et al. | 568/454 |
| 4,599,206 | 7/1982 | Billig et al. | 568/454 |

FOREIGN PATENT DOCUMENTS

| | | | |
|---|---|---|---|
| 0002821 | 12/1978 | European Pat. Off. | 568/454 |
| 0009115 | 8/1979 | European Pat. Off. | 568/454 |
| 0016285 | 10/1980 | European Pat. Off. | 568/454 |
| 0016286 | 10/1980 | European Pat. Off. | 568/454 |
| 0054986 | 6/1982 | European Pat. Off. | 568/454 |
| 0096988 | 12/1983 | European Pat. Off. | 568/454 |
| 0096986 | 12/1983 | European Pat. Off. | |
| 0096987 | 12/1983 | European Pat. Off. | |
| 0149894 | 7/1985 | European Pat. Off. | 568/454 |
| 1325199 | of 1973 | United Kingdom | 568/454 |
| 2068377 | 8/1981 | United Kingdom | 568/454 |

OTHER PUBLICATIONS

*J. Org. Chem.* vol. 34, No. 2, Feb. 1969, pp. 327–329, "A Low Pressure System for Producing Normal Aldehydes" by Pruett et al.

*J. Organicmetallic Chem.* vol. 258 (1983) pp. 343–350, "Hydroformylation of Less Reactive Olefins with Modified Rhodium Catalysts" by P. Van Leeuwen et al.

*Tetrahedron* vol. 23, pp. 2067–2080 (1967) "Reaction of Trialkyl Phosphites with Aromatic Aldehydes" by F. Ramirez et al.

*Bulletin of the Japan Petroleum Institute,* vol. 19, No. 1 (1977) "Hydroformylation of Olefins Using Rhodium Complex Catalysts by Y. Matsui et al., Part 1 (pp. 62–67) and Part 2 (pp. 68–72).

*Zhurnal Obshchel Kchimii,* vol. 31, No. 6 (1961) "The Saponification of Full Esters of Phosphoric Acid by Pure Water" by M. Imaev (pp. 1646–1650).

Rohm & Hass Co. Brochure on Amberlyst® A-21 pp. 1-7, Jan. 1963 (Rev. Jul. 1966).

*J. Organometal. Chem.,* 27 (1971) pp. 119–131, "Metal Carbonyl Chemistry XIV Reactions of Rhodium Compounds with Ligands" by B. L. Booth et al.

*American Chem. Soc.,* 73 (1981) pp. 351–354 "Selected Novel Trivalent Organophosphorus Processing Stabilizers for Polyolefins" by J. D. Spivack et al.

*Primary Examiner*—Werren B. Lone
*Attorney, Agent, or Firm*—Reynold J. Finnegan

[57] ABSTRACT

Transition metal-diorganophosphite complex catalyzed carbonylation processes, especially hydroformylation, as well as transition metal-diorganophosphite ligand complex compositions, diorganophosphite ligands and transition metal-diorganophosphite catalysts.

33 Claims, No Drawings

TRANSITION METAL COMPLEX CATALYZED REACTIONS

This application is a continuation-in-part of U.S. application Ser. No. 685,025 filed Dec. 28, 1984, now U.S. Pat. No. 4,599,206, in which in turn is a continuation-in-part of U.S. application, Ser. No. 581,352 filed Feb. 17, 1984, now abandoned.

BRIEF SUMMARY OF THE INVENTION

1. Technical Field

This invention relates to transition metal complex catalyzed reactions using diorganophosphite ligands. More particularly this invention relates to transition metal-diorganophosphite complex catalyzed carbonylation processes, especially hydroformylation, as well as to transition metal-diorganophosphite ligand complexes.

2. Background Art

It is well known in the art the carbonylation reactions are enhanced by the use of a modified Group VIII metal catalyst e.g., catalysts comprising a Group VIII transition metal-phosphorus ligand complex.

Carbonylation processes directed to production of oxygenated products in the presence of a catalyst in general involve the reaction of an organic compound with carbon monoxide and preferably another reactant, especially hydrogen, and are well known in the art, e.g., see J. Falbe, "New Snythesis With Carbon Monoxide" Springer Verlag, New York 1980. Such processes may include the carbonylation of organic compounds such as olefins, acetylenes, alcohols and activated chlorides with carbon monoxide alone or with carbon monoxide and either hydrogen, alcohol, amine or water, as well as ring closure reactions of functional unsaturated compounds e.g. unsaturated amides with CO. One of the major types of known carbonylation reactions is the hydroformylation of an olefinic compound with carbon monoxide and hydrogen to produce oxygenated products such as aldehydes using a Group VIII transition metal-phosphorus ligand complex wherein the phosphorus ligand is a triorganophosphine or triorganophosphite, followed by a subsequent aldolization reaction if desired.

It is further well known that the phosphorus ligand employed in such catalyzed carbonylation processes may have a direct effect on the success of such a given process. Moreover, while it is evident that the selection of the particular phosphorus ligand to be used in any such transition metal catalyzed carbonylation process depends in the main on the end result desired, the best overall processing efficiency may require a compromise selection among numerous factors involved, for it is known that not all phosphorus ligands will provide identical results with regard to all factors under all conditions. For example, in hydroformylation such factors as product selectivity, catalyst reactivity and stability, and ligand stability are often of major concern in the selection of the desired phosphorus ligand to be employed. Moreover, such a selection may also depend on the olefinic starting material involved in the hydroformylation process, since all olefins do not have the same degree of reactivity under all conditions. For instance, internal olefins and sterically hindered alpha olefins e.g. isobutylene, are in general much less reactive than sterically unhindered alpha olefins.

Thus, e.g. by tailoring of the metal-phosphorus ligand complex catalyst, specific desired results for the product, the process and/or catalyst performance may be obtained. For example, U.S. Pat. No. 3,527,809 teaches how alpha olefins can be selectively hydroformylated with rhodium-triorganophosphine or triorganophosphite ligand complexes to produce oxygenated products rich in normal aldehydes, while U.S. Pat. Nos. 4,148,830 and 4,247,486 disclose both liquid and gas recycle operations directed to the same result using a rhodiumtriphenylphosphine ligand complex catalyst. U.S. Pat. No. 4,283,562 discloses that branched-chain alkylphenylphosphine or branched-chain cycloalkylphenylphosphine ligands can be employed in a rhodium catalyzed hydroformylation process of olefin to produce aldehydes in order to provide a more stable catalyst against intrinsic deactivation while retarding the rate of the hydroformylation reaction far less than n-alkyldiphenylphosphine ligands, relative to that obtained using triphenylphosphine. U.S. Pat. No. 4,400,548 discloses that bisphosphine monooxide ligands can be employed to provide rhodium complex catalysts of improved thermal stability useful for the hydroformylation production of aldehydes.

However, despite the obvious benefits attendent with the prior art references mentioned above, the search for a more effective phosphorus ligand which will provide a more active, more stable and/or more all purpose type metal-phosphorus ligand complex catalyst is a constant one in the art and heretofore, unlike the present invention, has been centered for the most part on the use of triorganophosphine and triorganophosphite ligands.

DISCLOSURE OF INVENTION

It has now been discovered that diorganophosphite ligands may be employed as the phosphorus ligand in Group VIII transition metal complex catalyzed carbonylation processes to provide numerous advantages relative to heretofore commonly proposed Group VIII transition metal-phosphorus ligand complex catalysts.

For instance, the diorganophosphite ligands employable herein are useful in providing both improved catalytic activity and at the same time improved catalyst and ligand stability in carbonylation processes and particularly hydroformylation, even with less reactive olefins such as isobutylene and internal olefins. For example, the high catalytic activity provided by the diorganophosphite lignads allows one to carry out the hydroformylation of olefins at lower temperatures than generally preferred when conventional ligands such as triorganophosphines are employed. Likewise, in the hydroformylation of olefins enhanced ligand and catalyst stability against inherent side reactions, such as stability against reacting with the aldehyde product, hydrolytic stability and stability against hydrogenolysis of the ligand may be achieved by the use of the diorganophosphite ligands relative to the use of triorganophosphite ligands. Further, the use of the diorganophosphite ligands employable herein provide an excellent means for controlling product selectivity in hydroformylation reactions. For example, the diorganophosphites have been found to be very effective ligands when oxygenated products, e.g. aldehydes, having very low normal to iso (branched) product ratios are desired. Moreover, the diorganophosphite ligands employable herein have not only been found to provide excellent catalyst activity and both catalyst and ligand stability in the hydroformylation of sterically unhindered alpha olefins, as well as less reactive type olefins, such as sterically hindered alpha olefins e.g. isobutylene, and internal olefins, but have also been found to be especially useful in providing such catalyst activity and both catalyst and ligand stability when hydroformylating mixed alpha olefin and internal olefin starting materials.

Thus it is an object of this invention to provide an improved carbonylation process and especially a hydroformylation process, wherein said process is carried out in the presence of a Group VIII transition metal-diorganophosphite ligand complex catalyst. It is also an object of this invention to provide a novel class of Group VIII transition metal-diorganophosphite ligand complexes suitable for use in such carbonylation and hydroformylation processes. Other objects and advantages of this invention will become readily apparent from the following written description and appended claims.

Accordingly, a generic aspect of this invention can be described as a process for carbonylation comprising reacting an organic compound capable of being carbonylated with carbon monoxide in the presence of a Group VIII transition metal-phosphorus ligand complex catalyst wherein the phosphorus ligand of said complex catalyst is a diorganophosphite ligand having the general formula

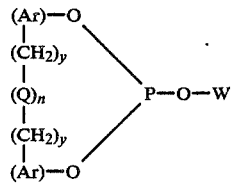

wherein W represents an unsubstituted or substituted monovalent hydrocarbon radical; wherein each Ar group represents an identical or different substituted or unsubstituted aryl radical, wherein each y individually has a value of 0 to 1, wherein Q is a divalent bridging group selected from the class consisting of —$CR^1R^2$—, —O—, —S—, —$NR^3$—, —$SiR^4R^5$— and —CO—, wherein each $R^1$ and $R^2$ radical individually represents a radical selected from the group consisting of hydrogen, alkyl of 1 to 12 carbon atoms (e.g. methyl, propyl, isopropyl, butyl, isodecyl, dodecyl, etc.) phenyl, tolyl and anisyl, wherein each $R^3$, $R^4$, and $R^5$ radical individually represents —H or —$CH_3$, and wherein n has a value of 0 or 1. Preferably each $R^1$ and $R^2$ radical individually represents —H or —$CH_3$.

Another preferred generic aspect of this invention comprises the Group VIII transition metal-diorganophosphite ligand complexes and catalyst precursor solutions thereof as described more fully herein below.

DETAILED DESCRIPTION

As seen by the above formula the diorganophosphite ligands employable herein represent an entirely different class of compounds than triorganophosphite ligands. The diorganophosphites employable herein contain only two organic radicals bonded to the phosphorus atom through oxygen, one of said organic radicals being bonded through two phenolic oxygen atoms (wherein each oxygen atom is bonded to a separate aryl radical) and the other organic radical through a single phenolic or alcoholic oxygen atom. Triorganophosphites contain three organic radicals each radical being bonded to the phosphorus atom through its own individual oxygen atom. Thus if hydrolyzed, the diorganophosphite ligands employable herein would yield both a diphenolic compound in which each phenolic oxygen atom is bonded to a separate aryl radical, and a mono-ol compound, while triorganophosphite ligands would yield the equivalent of three mono-ol compounds.

Accordingly, the subject invention encompasses the carrying out of any known carbonylation process in which the catalyst thereof is replaced by a Group VIII transition metal-diorganophosphite ligand catalyst as disclosed herein. As noted above such caerbonylation reactions may involve the reaction of organic compounds with carbon monoxide, or carbon monoxide and a third reactant e.g. hydrogen in the presence of a catalytic amount of a Group VIII transition metal-diorganophosphite ligand complex catalyst, said ligand having the general formula

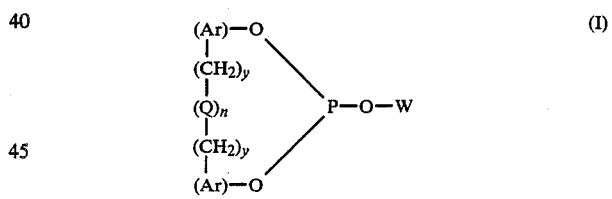

wherein W, Ar, Q, y and n are the same defined above.

More preferably the subject invention involves the use of such a Group VIII transition metal-diorganophosphite ligand complex catalyst and free diorganophosphite ligand in the production of aldehydes wherein an olefinic compound is reacted with carbon monoxide and hydrogen. Th aldehydes produced correspond to the compounds obtained by the addition of a carbonyl group to an olefinically unsaturated carbon atom in the starting material with simultaneous saturation of the olefinic bond. Such preferred processes are known in industry under varying names such as the oxo process or reaction, oxonation, the Roelen reaction and more commonly hydroformylation. Accordingly, the processing techniques of this invention may correspond to any of the known processing techniques heretofore employed in conventional carbonylation and especially hydroformylation reactions.

For instance, the preferred hydroformylation process can be conducted in continuous, semicontinuous, or batch fashion and involve a liquid recycle and/or gas recycle operation as desired. Likewise, the manner or order of addition of the reaction ingredients, catalyst and solvent are also not critical and may be accomplished in any conventional fashion.

In general, the preferred hydroformylation reaction is preferably carried out in a liquid reaction medium that contains a solvent for the catalyst, preferably one in which both the olefinically unsaturated compound and catalyst are substantially soluble. In addition, as is the case with prior art hydroformylation processes that employ a rhodiumphosphorus complex catalyst and free phosphorus ligand, it is highly preferred that the hydroformylation process of this invention be effected in the presence of free diorganophosphite ligand as well as in the presence of the complex catalyst. By "free ligand" is meant diorganophosphite ligand that is not complexed with the Group VIII transition metal atom in the active complex catalyst.

The more preferred hydroformylation process of this invention is an improved selective hydroformylation over those known Group VIII transition metalphosphorus ligand complex catalyzed hydroformylation reactions due to the improved catalyst reactivity as well as simultaneous improved catalyst and ligand stability, and other benefits, afforded by the use of the diorganophosphite ligands employable herein, as opposed to the triorganophosphine and triorganophosphite ligands heretofore employed in the prior art.

The Group VIII transition metals which make up the metal-diorganophosphite complexes of this invention include those selected from the group consisting of rhodium (Rh), cobalt (Co), iridium (Ir), ruthenium (Ru), iron (Fe), nickel (Ni), palladium (Pd), platinum (Pt) and osmium (Os), and mixtures thereof, with the preferred metals being Rh, Co, Ir and Ru, more preferably Rh and Co, especially Rh. It is to be noted that the successful practice of this invention does not depend and is not predicated on the exact structure of the catalytically active metal complex species, which may be present in their mononuclear, dinuclear and or higher nuclearity forms. Indeed the exact active structure is not known. Although it is not intended herein to be bound to any theory of mechanistic discourse, it appears that the active catalytic species may in its simplest form consist essentially of the Group VIII transition metal in complex combination with the carbon monoxide and a diorganophosphite ligand.

The term "complex" as used herein and in the claims means a coordination compound formed by the union of one or more electronically rich molecules or atoms capable of independent existence with one or more electronically poor molecules or atoms, each of which is also capable of independent existence. The diorganophosphite ligands employable herein which possess the element phosphorus have one available or unshared pair of electrons and thus are capable of forming a coordinate bond with the Group VIII transition metal. As can be surmised from the above discussion, carbon monoxide (which is also properly classified as a ligand) is also present and complexed with the Group VIII transition metal. The ultimate composition of the active complex catalyst may also contain an additional organic ligand or anion satisfying the coordination sites or nuclear charge of the Group VIII transition metal as in the case of heretofore conventional Group VIII transition metal-triorganophosphine or phosphite catalysts. Illustrative additional organic ligands and anions include e.g. hydrogen− ($H^-$), halogen− ($Cl^-$, $Br^-$, $I^-$), alkyl−, aryl−, substituted aryl−, $CF_3^-$, $C_2F_5^-$, $CN^-$, $R_2PO^-$ and $RP(O)(OH)O^-$ (wherein each R is alkyl or aryl), acetate−, acetylacetonate−, $SO_4^{2-}$, $PF_4^-$, $PF_6^-$, $NO_2^-$, $NO_3^-$, $CH_3O^-$, $CH_2\!=\!CHCH_2^-$, $C_6H_5CN$, $CH_3CN$, $NO$, $NH_3$, pyridine, $(C_2H_5)_3N$, mono-olefins, diolefins and triolefins, tetrahydrofuran, and the like. It is of course to be understood that the active complex species is preferably free of any additional organic ligand or anion that might poison the catalyst and have an undue adverse effect on catalyst performance. For instance it is known that in conventional rhodium catalyzed hydroformylation reactions that halogen anions and sulfur compounds can poison the catalyst. Accordingly it is preferred that in the rhodium catalyzed hydroformylation reactions of this invention that the active catalysts also be free of halogen and sulfur directly bonded to the rhodium.

The number of available coordination sites on such Group VIII transition metals is well known in the art and may range in number from 4 to 6. By way of illustration it appears that the preferred active rhodium catalyst species of this invention contains, in its simplest form, an amount of diorganophosphite ligand and carbon monoxide equal to a total of four moles in complex combination with one mole of rhodium. Thus the active species may comprise a complex catalyst mixture, in their monomeric, dimeric or higher nuclearity forms, which are characterized by one, two, and/or three diorganophosphite molecules complexed per one molecule of rhodium. As noted above carbon monoxide is also present and complexed with the rhodium in the active species. Moreover, as in the case of conventional rhodium-triorganophosphine or phosphite ligand complexed catalyzed hydroformylation reactions, the active catalyst species of which is generally considered to also contain hydrogen directly bonded to the rhodium, it is likewise considered that the active species of the preferred rhodium catalyst employed in this invention during hydroformylation may also be complexed with hydrogen in addition to the diorganophosphite and carbon monoxide ligands. Indeed it is believed that the active species of any Group VIII transition metal catalyst of this invention may also contain hydrogen in addition to the diorganophosphite and carbon monoxide ligands during a hydroformylation process particularly in view of the hydrogen gas employed in the process.

Moreover, regardless of whether one preforms the active complex catalyst prior to introduction into the carbonylation reaction zone or whether the active species is prepared in situ during the carbonylation reaction, it is preferred that the carbonylation, and especially the hydroformylation reaction be effected in the presence of free diorganophosphite ligand. Thus by way of illustration the ultimate composition of the preferred active rhodium complex species catalyst can be likened or attributable to the outcome of competing reactions between carbon monoxide and the diorganophosphite ligands for complexing or coordination sites with the rhodium element. These competing reactions can be disturbed or influenced, within significant limits, by increasing or decreasing the concentration of the diorganophosphite ligand. As a generalized statement, the component (carbon monoxide or diorganophosphite ligand) which can shift the equilibrium of the competing reaction in its favor should enjoy the greater opportunities of occupying the coordination or complexing sites. For example, one may view the function of free diorganophosphite ligand as either maintaining the status quo of the various forms of active complex catalyst during the hydroformylation, or as a means for shifting the equilibrium of the competing reactions in its favor and therefore causing additional diorganophosphite ligands to enter into complex combination with rhodium with the probable eviction of a similar number of carbon monoxide ligands from the complex catalyst.

The diorganophosphite ligands employable in this invention as noted above are those having the general formula

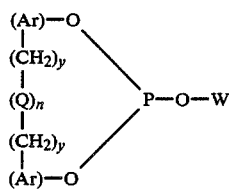

wherein W represents an unsubstituted or substituted monovalent hydrocarbon radical; wherein each Ar group represents an identical or different substituted or unsubstituted aryl radical, wherein each y individually has a value of 0 or 1, preferably 0, wherein Q is a divalent bridging group selected from the class consisting of $-CR^1R^2-$, $-O-$, $-S-$, $-NR^3-$, $-Si^4R^5-$ and $-CO-$, wherein each $R^1$ and $R^2$ radical individually represents a radical selected from the group consisting of hydrogen, alkyl of 1 to 12 carbon atoms (e.g. methyl, propyl, isopropyl, butyl, isodecyl, dodecyl, etc.), phenyl, tolyl and anisyl, wherein each $R^3$, $R^4$, and $R^5$ radical individually represent $-H$ or $-CH_3$, and wherein n has a value of 0 to 1. Moreover, when n is 1, Q is preferably a $-CR^1R^2-$ bridging group as defined above and more preferably methylene ($-CH_2-$) or alkylidene ($-CHR^2-$, wherein $R^2$ is an alkyl radical of 1 to 12 carbon atoms as defined above, especially methyl).

Illustrative monovalent hydrocarbon radicals represented by W in the above diorganophosphite formula include substituted or unsubstituted monovalent hydrocarbon radicals containing from 1 to 30 carbon atoms selected from the group consisting of substituted or unsubstituted alkyl, aryl, alkaryl, aralkyl and alicyclic radicals. Preferably W represents a substituted or unsubstituted radical selected from the group consisting of alkyl and aryl radicals.

More specific illustrative monovalent hydrocarbon radicals represented by W include primary, secondary and tertiary alkyl radicals such as methyl, ethyl, n-propyl, isopropyl, butyl, sec-butyl, t-butyl, t-butylethyl, t-butylpropyl, n-hexyl, amyl, sec-amyl, t-amyl, iso-octyl, 2-ethylhexyl, decyl, octadecyl and the like; aryl radicals, such as phenyl, naphthyl, anthracyl, and the like; aralkyl radicals, such as benzyl, phenylethyl, and the like; alkaryl radicals, such as tolyl, xylyl, and the like; and alicyclic radicals, such as cyclopentyl, cyclohexyl, cyclooctyl, cyclohexylethyl, and the like. Preferably the unsubstituted alkyl radicals may contain from 1 to 18 carbon atoms, more preferably from 1 to 10 carbon atoms, while the unsubstituted aryl, aralkyl, alkaryl and alicyclic radicals preferably contain from 6 to 18 carbon atoms.

Illustrative aryl radicals represented by the Ar groups in the above diorganophosphite formula include both substituted and unsubstituted aryl radicals. Such aryl radicals may contain from 6 to 18 carbon atoms such as phenylene ($C_6H_4$), naphthylene ($C_{10}H_6$), anthracylene ($C_{14}H_8$), and the like.

Illustrative substituent groups that may be present on the monovalent hydrocarbon radicals represented by W as well as the aryl groups represented by Ar in the above diorganophosphite formula include monovalent hydrocarbon radicals such as the same type of substituted or unsubstituted alkyl, aryl, alkaryl, aralkyl and alicyclic radicals mentioned above for W, as well as silyl radicals such as $-Si(R^6)_3$ and $-Si(OR^6)_3$, amino radicals such as $-N(R^6)_2$, acyl radicals such as $-C(O)R^6$, carbonyloxy radicals such as $-C(O)OR^6$, oxycarbonyl radicals such as $-OC(O)R^6$, amido radicals such as $-C(O)N(R^6)_2$ and $-N(R^6)C(O)R^6$, sulfonyl radicals such as $-S(O)_2R^6$, sulfinyl radicals such as $-S(O)R^6$, ether (i.e. oxy) radicals such as $-OR^6$, thionyl ether radicals such as $-SR^6$, phosphonyl radicals such as $-P(O)(R^6)_2$, and halogen, nitro, cyano, trifluoromethyl and hydroxy radicals, and the like, wherein each $R^6$ individually represents the same or different, substituted or unsubstituted monovalent hydrocarbon radical having the same meaning as defined herein with the proviso that in amino substituents such as $-N(R^6)_2$, each $R^6$ taken together can also represent a divalent bridging group that forms a heterocyclic radical with the nitrogen atom and in amino and amido substituents such as $-N(R^6)_2$, $-C(O)N(R^6)_2$ and $-N(R^6)C(O)R^6$ each $-R^6$ bonded to N can also be hydrogen, while in phosphonyl substituents such as $-P(O)(R^6)_2$, one $R^6$ radical can also be hydrogen. Preferably the monovalent hydrocarbon substituent radicals, including those represented by $R^6$, are unsubstituted alkyl or aryl radicals, although if desired they in turn may be substituted with any substituent which does not unduly adversely effect the process of this invention, such as e.g. those hydrocarbon and non-hydrocarbon substituent radicals already herein outlined above.

Among the more specific unsubstituted monovalent hydrocarbon substitute radicals, including those represented by $R^6$, that may be bonded to the monovalent hydrocarbon radicals represented by W and/or the Ar groups of the above diorganophosphite formula that may be mentioned are alkyl radicals including primary, secondary and tertiary alkyl radicals such as methyl, ethyl, n-propyl, isopropyl, butyl, sec-butyl, t-butyl, t-butylethyl, t-butylpropyl, n-hexyl, amyl, sec-amyl, t-amyl, iso-octyl, decyl, and the like; aryl radicals such as phenyl, naphthyl and the like; aralkyl radicals such as benzyl, phenylethyl, triphenylmethylethane, and the like; alkaryl radicals such as tolyl, xylyl, and the like; and alicyclic radicals such as cyclopentyl, cyclohexyl, 1-methylcyclohexyl, cyclooctyl, cyclohexylethyl, and the like. More specific illustrative non-hydrocarbon substituents that may be present on the monovalent hydrocarbon radicals represented by W and/or the Ar groups of the above diorganophosphite formula include e.g. halogen, preferably chlorine or fluorine, $-NO_2$, $-CN$, $-CF_3$, $-OH$, $-Si(CH_3)_3$, $-Si(OCH_3)_3$, $-Si(C_3H_7)_3$, $-C(O)CH_3$, $-C(O)C_2H_5$, $-OC(O)C_6H_5$, $-C(O)OCH_3$, $-N(CH_3)_2$, $-NH_2$, $-NHCH_3$, $-NH(C_2H_5)$, $-CONH_2$, $-CON(CH_3)_2$, $-S(O)_2C_2H_5$, $-OCH_3$, $-OC_6H_5$, $-C(O)C_6H_5$, $-O(t-C_4H_9)$, $-SC_2H_5$, $-OCH_2CH_2OCH_3$, $-(OCH_2CH_2)_2OCH_3$, $-(OCH_2CH_2)_3OCH_3$, $-SCH_3$, $-S(O)CH_3$, $-SC_6H_5$, $-P(O)(C_6H_5)_2$, $-P(O)(CH_3)_2$, $-P(O)(C_2H_5)_2$, $-P(O)(C_3H_7)_2$, $-P(O)(C_4H_9)_2$, $-P(O)(C_6H_{13})_2$, $-P(O)CH_3(C_6H_5)$, $-P(O)(H)(C_6H_5)$, $-NHC(O)CH_3$,

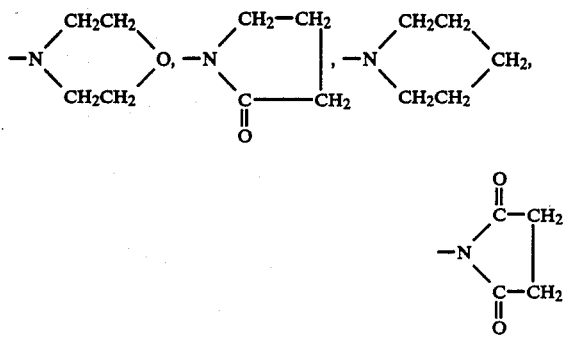

and the like. In general, the substituent radicals present on the monovalent hydrocarbon radicals represented by W and the Ar groups of the above diorganophosphite formula may also contain from 1 to 15 carbon atoms and may be bonded to the monovalent hydrocarbon radicals represented by W and/or such Ar groups in any suitable position as may the bridging group $-(CH_2)_y-(Q-)_n-(CH_2)_y-$ connecting the two Ar groups of the above formula. Moreover, each Ar radical and/or radical represented by W may contain one or more such substituent groups which substituent groups may also be the same or different in any given diorganophosphite.

Among the more preferred diorganophosphite ligands are those wherein the two Ar groups linked by the bridging group represented by $-(CH_2)_y-(Q-)_n-(CH_2)_y-$ in the above diorganophosphite formula are bonded through their ortho positions in relation to the oxygen atoms that connect the Ar groups to the phosphorus atom. It is also preferred that any substituent radical, when present on such Ar groups, including any aryl radical represented by W be bonded in the para and/or ortho position of the aryl group in relation to the oxygen atom that bonds the given substituted aryl group to the phosphorus atom.

Accordingly, a preferred class of diorganophosphite ligands employable herein are those wherein W is a substituted or unsubstituted alkyl radical. Preferred alkyl radicals include those unsubstituted alkyl radicals containing from 1 to 18 carbon atoms, more preferably from 1 to 10 carbon atoms, such as those defined above, and such alkyl radicals when substituted with a non-hydrocarbon substituent as discussed above e.g. silyl radicals such as $-Si(R^6)_3$, and $-Si(OR^6)_2$; acyl radicals such as $-C(O)R^6$; carbonyloxy radicals such as $-C(O)OR^6$; oxycarbonyl radicals such as $-OC(O)R^6$; amido radicals such as $-C(O)N(R^6)_2$ and $-N(R^6)-C(O)R^6$; sulfonyl radicals such as $-S(O)_2R^6$; sulfinyl radicals such as $-S(O)R^6$; ether (i.e. oxy) radicals such as $-OR^6$, thionyl ether radicals such as $-SR^6$ and phosphonyl radicals such as $-P(O)(R^6)_2$, wherein $R^6$ is the same as defined above, as well as halogen, nitro, cyano, trifluoromethyl and hydroxy radicals, and the like. An electronegatively substituted alkyl radical has the potential of forming a weak coordinate bond with the Group VIII transition metal complex, and such substituents may render the Group VIII transition metal-diorganophosphite complex catalyst, and in particular the rhodium catalysts, in hydroformylation, more catalytically stable. The most preferred electronegatively substituted alkyl radicals are those of the formula $-C(R^7)_2-_pP(O)(R^6)_2$ wherein each $R^6$ is the same as defined above, wherein each $R^7$ is individually a radical which may be the same or different and which is selected from the group consisting of hydrogen and an alkyl radical containing from 1 to 4 carbon atoms, and p has a value of 1 to 10, especially $-(CH_2)-_pP(O)(R^6)_2$ radicals wherein p is 1 to 3 and each $R^6$ is individually the same or different and is a radical selected from the group consisting of alkyl radicals containing from 1 to 4 carbon atoms, phenyl, and cyclohexyl radicals, with the proviso that one $R^6$ radical can also be hydrogen.

Such types of diorganophosphite ligands employable in this invention and/or methods for their preparation are well known. For instance a conventional method for preparing such ligands comprises reacting a corresponding organic diphenolic compound (e.g. 2,2'-dihydroxybiphenyl) with phosphorus trichloride to form an organic phosphorochloridite intermediate (e.g. 1,1'-biphenyl-2,2'diyl-phosphorochloridite) which in turn is reacted with a corresponding mono-hydroxy compound (e.g. 2,6-di-t-butyl-4-methylphenol) in the presence of an HCl acceptor, e.g. an amine, to produce the desired diorganophosphite ligand [e.g. 1,1'-biphenyl-2,2'-diyl-(2,6-di-t-butyl-4-methylphenyl)phosphite]. Optionally, these ligands may also be prepared in the reverse order, for instance, from a preferred organic phosphorodichloridite (e.g. 2,6-di-t-butyl-4-methylphenyl phosphorodichloridite) and a corresponding diphenolic compound (e.g. 2,2'-di-hydroxybiphenyl) in the presence of an HCl acceptor, e.g. an amine, to produce the desired diorganophosphite ligand, [e.g. 1,1'-biphenyl-2,2'-diyl-(2,6-di-t-butyl-4-methylphenyl)phosphite].

Accordingly, a preferred class of diorganophosphite ligands employable in this invention is that of the formula

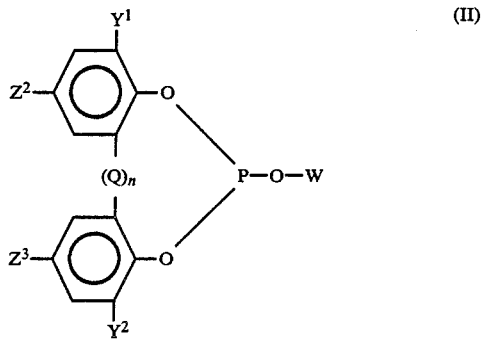
(II)

wherein Q is $-CR^1R^2$ wherein each $R^1$ and $R^2$ radical individually represents a radical selected from the group consisting of hydrogen, alkyl of 1 to 12 carbon atoms (e.g. methyl, propyl, isopropyl, butyl, isodecyl, dodecyl, etc.) phenyl, tolyland anisyl, and n has a value of 0 to 1; wherein each $Y^1$, $Y^2$, $Z^2$, and $Z^3$ group individually represents a radical selected from the group consisting of hydrogen, an alkyl radical having from 1 to 8 carbon atoms, substituted or unsubstituted aryl, alkaryl, aralkyl and alicyclic radicals as defined and exemplified herein above (e.g. phenyl, benzyl, cyclohexyl, 1-methylcyclohexyl, and the like), cyano, halogen, nitro, trifluoromethyl, hydroxy, as well as the carbonyloxy, amino, acyl, phosphonyl, oxycarbonyl, amido, sulfinyl, sulfonyl, silyl, ether, and thionyl radicals as defined and exemplified herein above, with the proviso that both $Y^1$ and $Y^2$ are radicals having a steric hindrance of isopropyl, or more preferably t-butyl, or greater, and wherein W represents an alkyl radical having from 1 to 18 carbon atoms, preferably from 1 to 10 carbon atoms. Preferably Q represents a methylene ($-CH_2-$) bridging group or an alkylidene ($-CHR^2-$) bridging group wherein $R^2$ is an alkyl radical of 1 to 12 carbon atoms as defined above, especially methyl ($-CHCH_3-$). The preferred ligands are those of Formula (II) above, wherein both $Y^1$ and $Y^2$ are branched chain alkyl radicals having three to five carbon atoms, especially t-butyl, $Z^2$ and $Z^3$ are hydrogen or an alkyl radical, especially t-butyl.

Another preferred class of diorganophosphite ligands employable herein are those wherein W is a substituted or unsubstituted aryl radical such as defined above, especially substituted or unsubstituted phenyl radicals.

Further, it has been observed that in rhodium catalyzed hydroformylation reactions, when the diorganophosphite ligand employed is one in which W represents an aryl radical, that substitution (excluding any substitution caused by the bridging group $-(CH_2)_y-(Q)_n-(CH_2)_y-$) of the ortho position of the aryl group (W) and the two Ar groups of Formula (I), i.e. those positions relative to the oxygen atom that bonds each aryl group to the phosphorus atom of the diorganophosphite ligands may influence the catalytic activity and/or stability of the ligand. Apparently steric hindrance around the phosphorus atom of the diorganophosphite ligand caused by substitution in such ortho positions of all the aryl groups has an influence on ligand stability and/or catalytic activity, particularly with regard to hydroformylations carried out in the presence of excess free diorganophosphite ligand. For instance, diorganophosphite ligands in which all the aryl groups are unsubstituted aryl radicals (too little steric hindrance) and diorganophosphite ligands in which four of the total accumulative number of such ortho positions on the aryl groups are substituted with a radical having a steric hindrance of isopropyl or greater, (too much steric hindrance), are not considered desirable because of the poor ligand stability and/or catalytic activity that may be obtained with their use particularly in the presence of excess free ligand. On the other hand improved ligand stability and/or catalytic activity in rhodium catalyzed hydroformylation even in the presence of excess free ligand may be obtained when at least two of the total accumulative number of such ortho positions on all the aryl groups of the diorganophosphite ligand are substituted with a substituent radical having a steric hindrance of isopropyl, or more preferably t-butyl, or greater, provided that no more than three and preferably not more than two of the total accumulative number of such ortho positions on all the aryl groups are substituted with a radical having a steric hindrance of isopropyl or greater at the same time. In addition, diorganophosphite ligands in which two such available ortho positions of the two Ar groups of generic Formula (I) above are substituted with a radical having a steric hindrance of isopropyl, or more preferably t-butyl, or greater, appear to possess better ligand stability as a general rule than if the diorganophosphite ligands were so substituted in the two such available ortho positions of the aryl group represented by W. Moreover, in the preferred diorganophosphite ligands, the catalytic activity and/or stability may be further enhanced if one of said ortho positions of the aryl radical represented by W is substituted with an electronegative substituent, e.g. cyano, having the capability of forming a weak coordinate bond with the Group VIII transition metal.

Thus another preferred class of diorganophosphite ligands employable in this invention are those of the formulas

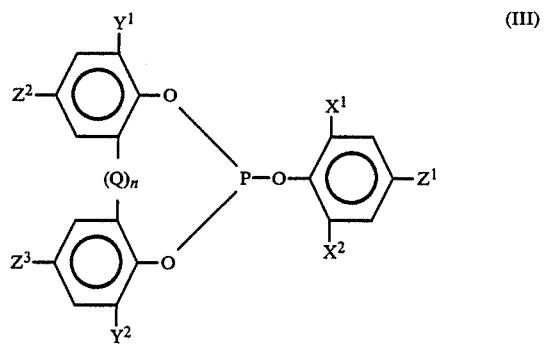
(III)

-continued

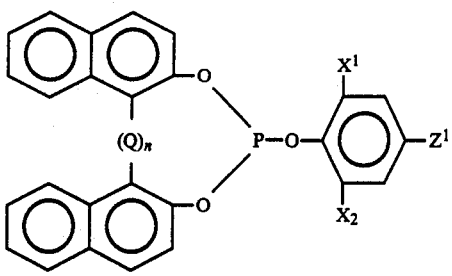

and

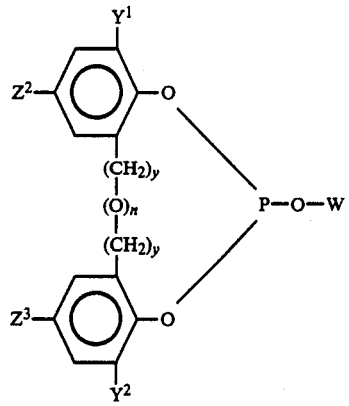

wherein Q is $-CR^1R^2$ wherein each $R^1$ and $R^2$ radical individually represents a radical selected from the group consisting of hydrogen, alkyl of 1 to 12 carbon atoms (e.g. methyl, propyl, isopropyl, butyl, isodecyl, dodecyl, etc.), phenyl, tolyl and anisyl, and n has a value of 0 to 1; wherein each $X^1$, $X^2$, $Y^1$, $Y^2$, $Z^1$, $Z^2$, and $Z^3$ group individually represents a radical selected from the group consisting of hydrogen, an alkyl radical having from 1 to 8 carbon atoms, substituted or unsubstituted aryl, alkaryl, aralkyl and alicyclic radicals as defined and exemplified above (e.g. phenyl, benzyl, cyclohexyl, 1-methylcyclohexyl, and the like), cyano, halogen, nitro, trifluoromethyl, hydroxy, as well as, amino, acyl, carbonyloxy, oxycarbonyl, amido, sulfonyl, sulfinyl, silyl, ether, phosphonyl, and thionyl radicals, as defined and exemplified hereinabove, with the proviso that at least both of the $X^1$ and $X^2$ groups or at least both of the $Y^1$ and $Y^2$ groups on a given diorganophosphite of Formulas (III) and (IV) above are radicals having a steric hindrance of isopropyl, or more preferably t-butyl, or greater, and with the proviso that in Formula (III) above no more than three and preferably no more than two of the $X^1$, $X^2$, $Y^1$, or $Y^2$ groups is a radical having a steric hindrance of isopropyl or greater at the same time. Preferably Q represents a methylene ($-CH_2-$) bridging group or an alkylidene ($-CHR^2-$) bridging group wherein $R^2$ is an alkyl radical of 1 to 12 carbon atoms as defined above, especially methyl ($-CHCH_3-$). Preferably the $X^1$, $X^2$, $Y^1$, and $Y^2$ groups are branched chain alkyl radicals having 3 to 5 carbon atoms, especially t-butyl. The more preferred ligands in Formula III are those wherein either both $Y^1$ and $Y^2$ groups are t-butyl or both $X^1$ and $X^2$ groups are t-butyl.

Yet another preferred class of diorganophosphite ligands, which are considered to be novel compositions of matter per se, employable in this invention are those of the formula wherein $Z^2$ and $Z^3$ each individually represent a radical selected from the group consisting of hydroxy ($-OH$) and an ether (i.e. oxy) radical such as $-OR^6$ wherein $R^6$ is the same as defined above and wherein W, $Y^1$, $Y^2$, Q, n and y are the same as defined above. Preferably $R^6$ is an alkyl radical of 1 to 18 carbon atoms, more preferably from 1 to 10 carbon atoms, e.g. primary, secondary, and tertiary alkyl radicals, such as methyl, ethyl, n-propyl, isopropyl, butyl, sec-butyl, t-butyl, t-butylethyl, t-butylpropyl, n-hexyl, amyl, sec-amyl, t-amyl, iso-octyl, 2-ethylhexyl, decyl, dodecyl, octadecyl, and the like. Further each y group preferably has a value of zero, and when n is 1, Q is preferably a $-CR^1R^2-$ bridging group as defined above, and especially $-CH_2-$ and $-CHCH_3-$. Most preferably n has a value of zero. Preferred unsubstituted and substituted monovalent hydrocarbon radicals represented by W include those as defined and exemplified above, for example alkyl radicals having from 1 to 18 carbon atoms, preferably from 1 to 10 carbon atoms, such as primary, secondary and tertiary alkyl radicals e.g. methyl, ethyl, n-propyl, isopropyl, butyl, sec-butyl, t-butyl, t-butylethyl, t-butylpropyl, n-hexyl, amyl, sec-amyl, t-amyl, iso-octyl, 2-ethylhexyl, decyl, octadecyl, and the like, as well as, aryl radicals, such as alpha-naphthyl, beta-naphthyl, and aryl radicals of the formula

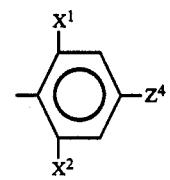

wherein $X^1$ and $X^2$ are the same as defined above, and $Z^4$ represents a radical selected from the group consisting of hydrogen, an alkyl radical having from 1 to 18, preferably from 1 to 12 carbon atoms, e.g. primary, secondary and tertiary alkyl radicals such as methyl, ethyl, n-propyl, isopropyl, butyl, sec-butyl, t-butyl, t-butylethyl, t-butylpropyl, n-hexyl, amyl, sec-amyl, t-amyl, iso-octyl, 2-ethylhexyl, nonyl, decyl, dodecyl, octadecyl, and the like, as well as, substituted and unsubstituted aryl, alkaryl, aralkyl and alicyclic radicals (e.g. phenyl, benzyl, cyclohexyl, 1-methylcyclohexyl, and the like), and cyano, halogen, nitro, trifluoromethyl, hydroxy, amino, acyl, carbonyloxy, oxycarbonyl, amido, sulfonyl, sulfinyl, silyl, ether, phosphonyl, and thionyl radicals as defined and exemplified above, with the proviso that at least both of the $X^1$ and $X^2$ groups or at least both of the $Y^1$ and $Y^2$ groups on a given diorganophosphite ligand of Formula (V) above are radicals having a steric hinderance of isopropyl, or more preferably t-butyl, or greater, and with the proviso that in Formula (V) above, no more than three and preferably no more than two of the $X^1$, $X^2$, $Y^1$ or $Y^2$ groups is a radical having a steric hinderance of isopropyl or greater at the same time.

Among the even more preferred diorganophosphite ligands of Formula (V) above are those of the formula

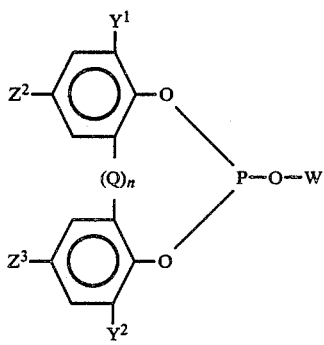
(VI)

wherein $Z^2$ and $Z^3$ each individually represent a radical selected from the group consisting of hydroxy and a —$OR^6$ radical wherein $R^6$ is an alkyl radical having from 1 to 18 carbon atoms, more preferably from 1 to 10 carbon atoms, as defined above; wherein Q represents a —$CR^1R^2$— bridging group as defined above and n has a value of 0 to 1, preferably 0; wherein $Y^1$ and $Y^2$ each individually represent a radical selected from the group consisting of branched chain alkyl radicals having from 3 to 12 carbon atoms, phenyl, benzyl, cyclohexyl and 1-methylcyclohexyl, preferably a branched chain alkyl radical of 3 to 5 carbon atoms; and wherein W represents a radical selected from the group consisting of an alkyl radical of 1 to 18 carbon atoms, preferably from 1 to 10 carbon atoms, alpha-naphthyl, beta-naphthyl, and an aryl radical of the formula

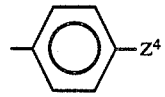

wherein $Z^4$ is the same as defined above.

The most preferred diorganophosphite ligands represented by Formula (VI) above are those wherein $Z^2$ and $Z^3$ are hydroxy or methoxy radicals, especially methoxy, wherein $Y^1$ and $Y^2$ both represent a branched chain alkyl radical of 3 to 5 carbon atoms; especially t-butyl; wherein W is selected from the group consisting of an alkyl radical of 1 to 10 carbon atoms and an aryl radical having the formula

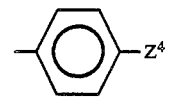

wherein $Z^4$ is selected from the group consisting of hydrogen and a methoxy radical, especially hydrogen; and wherein Q is a —$CR^1R^2$— bridging group as defined above, n having a value of 0 to 1. More preferably W is a methyl radical.

Illustrative examples of such diorganophosphite ligands include e.g.

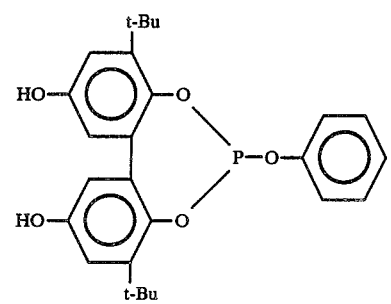

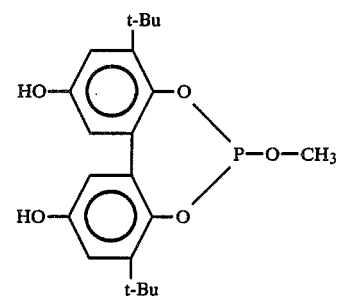

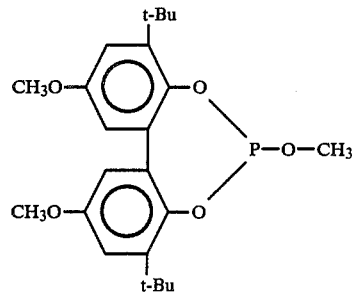

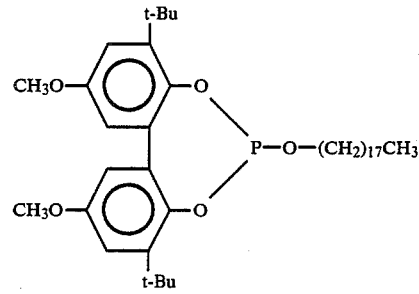

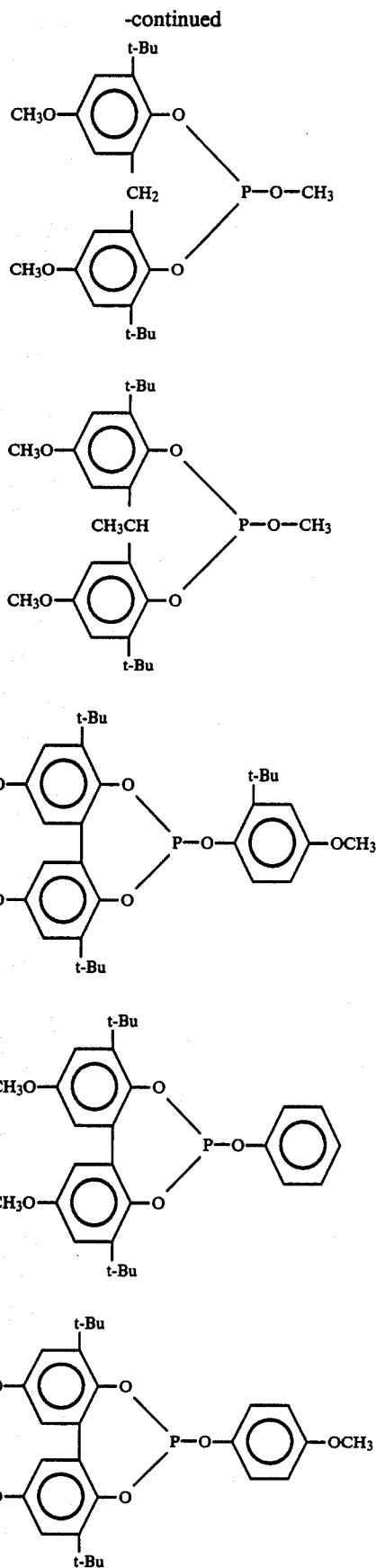
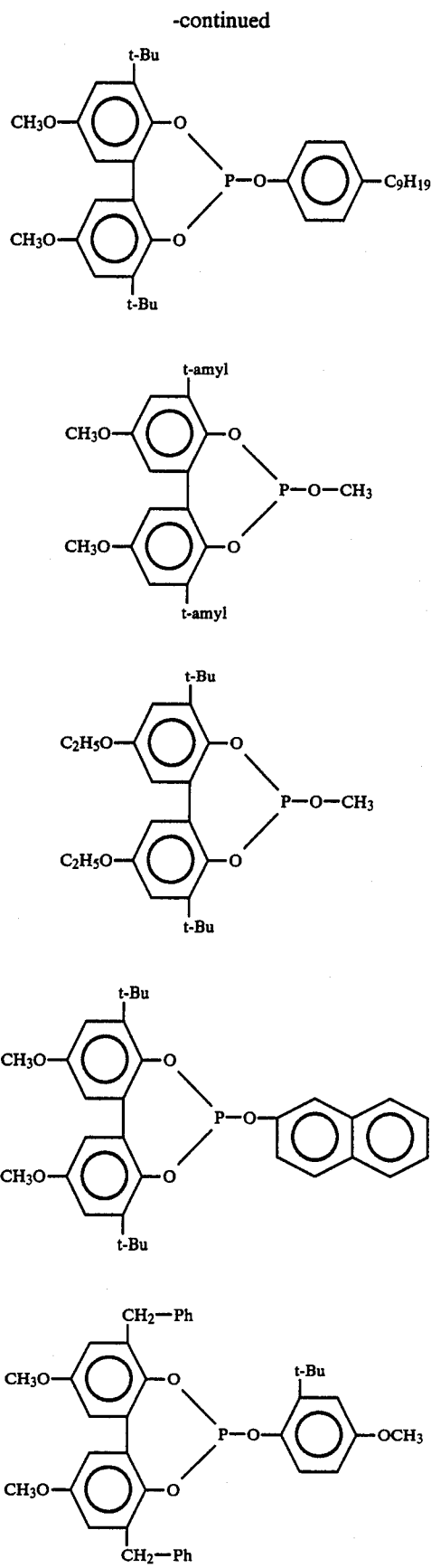

-continued
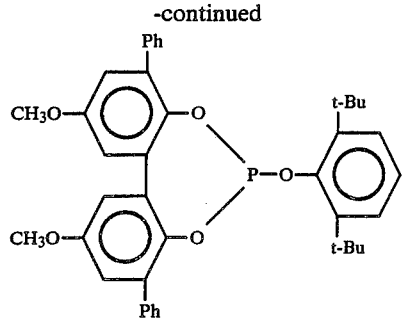
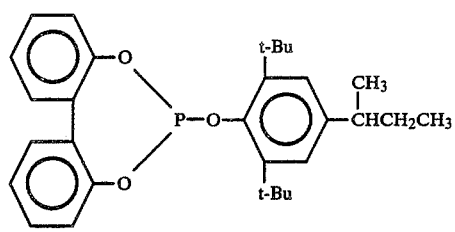
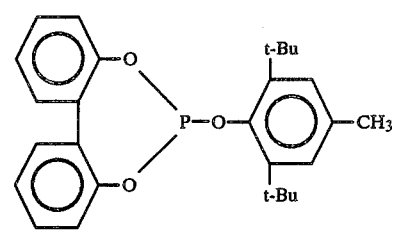
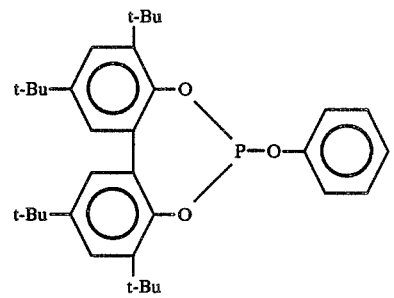
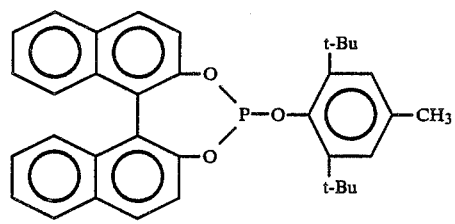
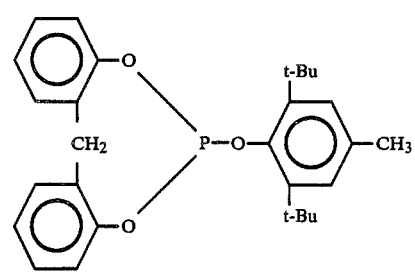
-continued
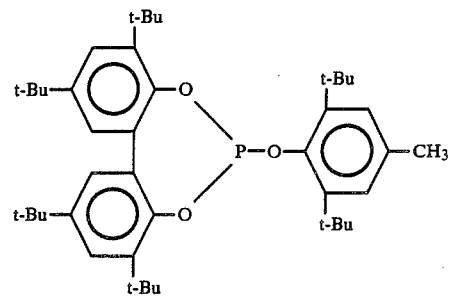
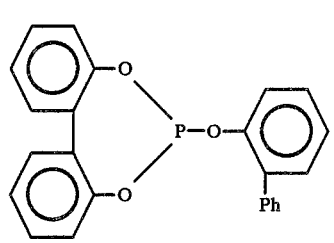
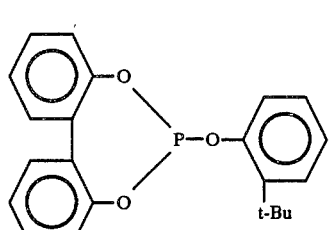
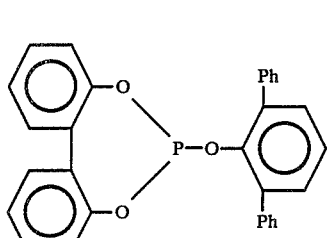
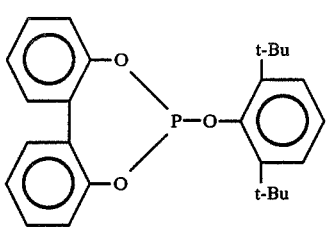
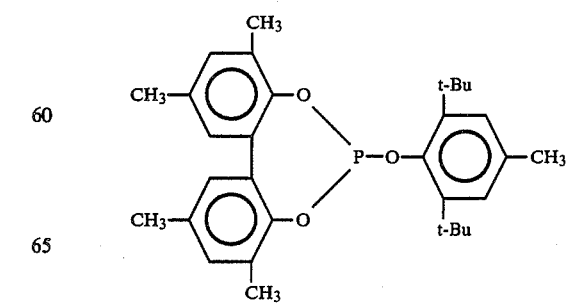

-continued
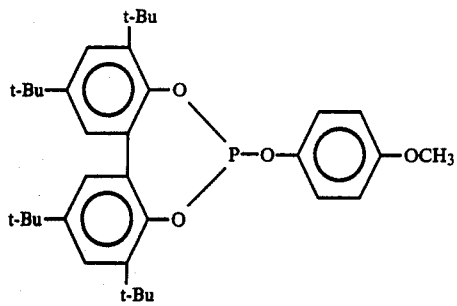
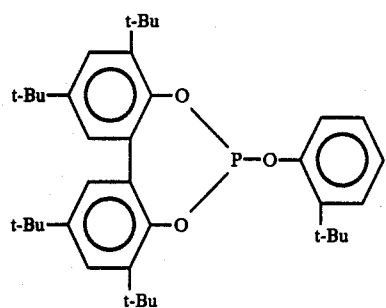
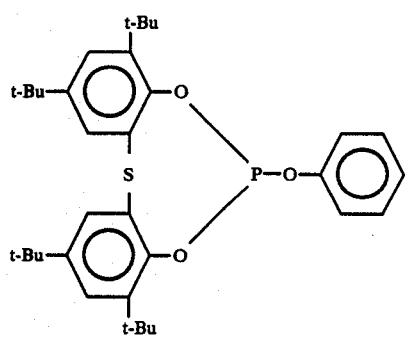
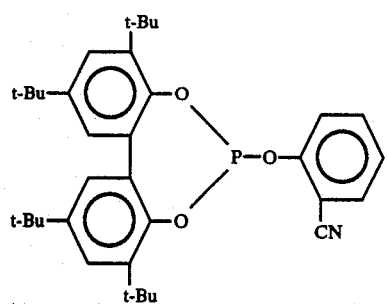
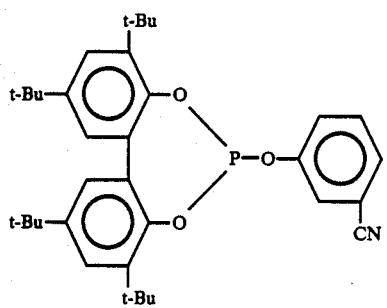
-continued
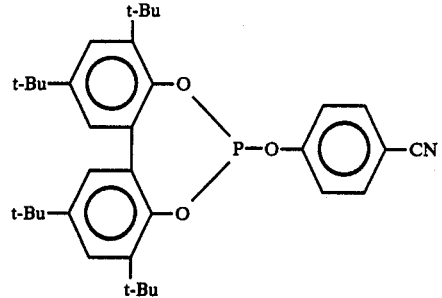
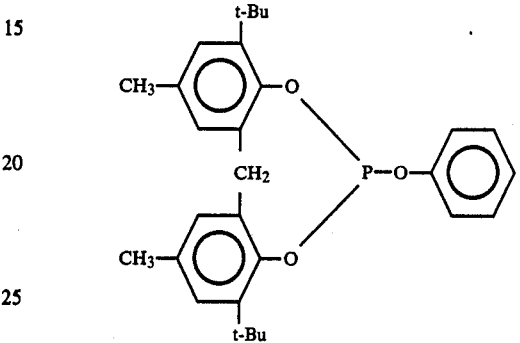
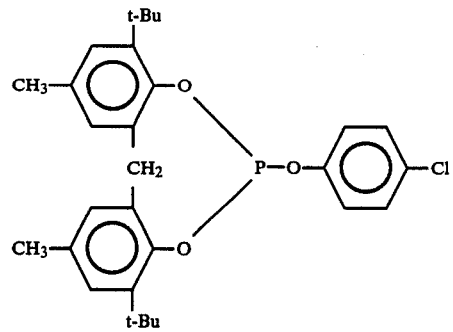
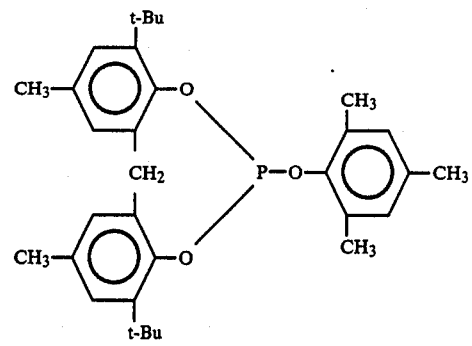
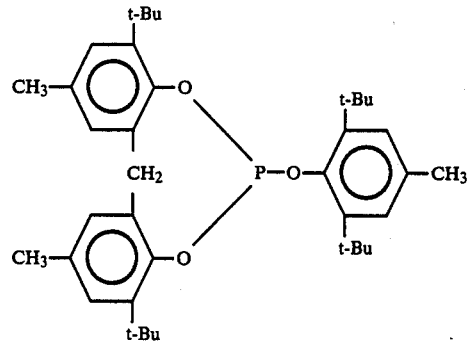

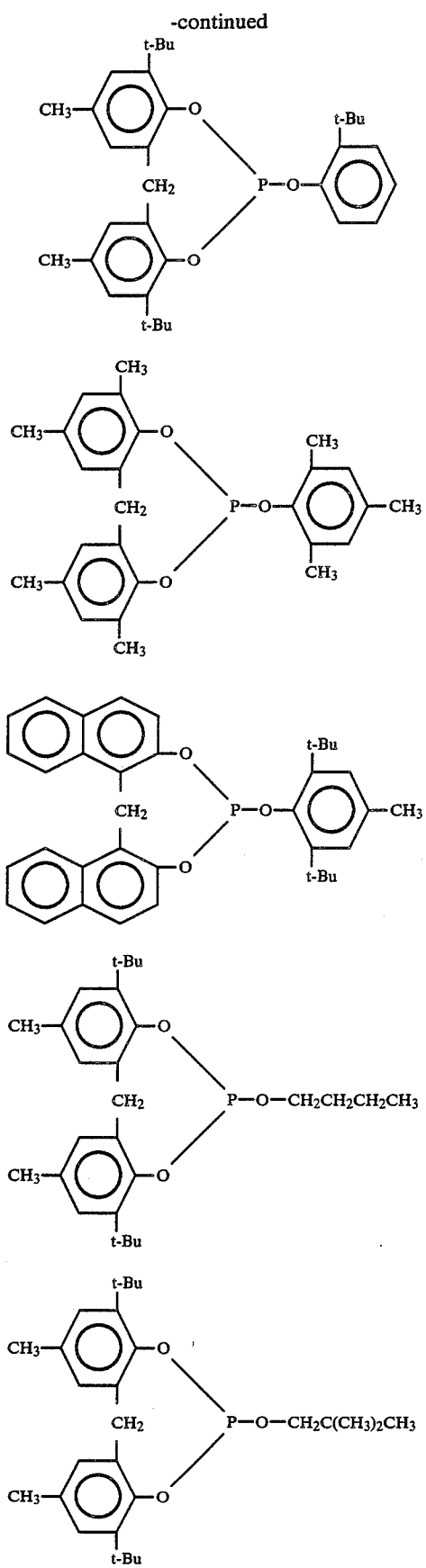

-continued
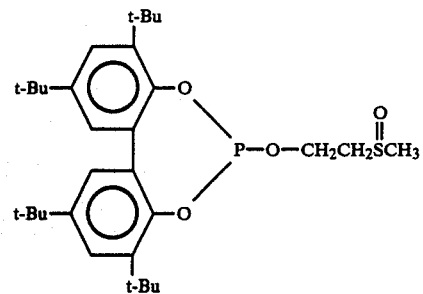
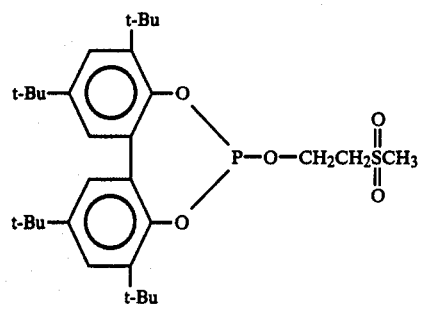
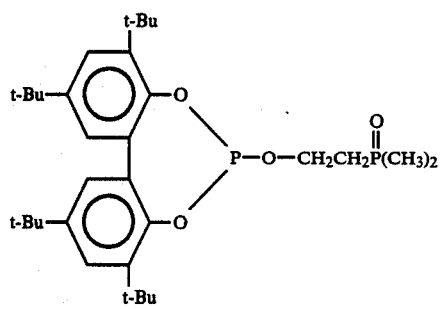
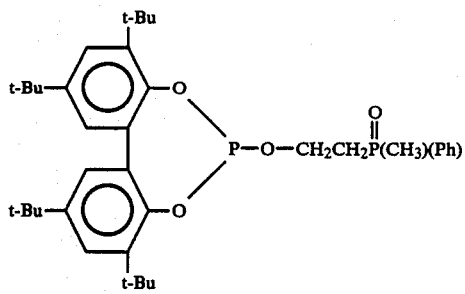
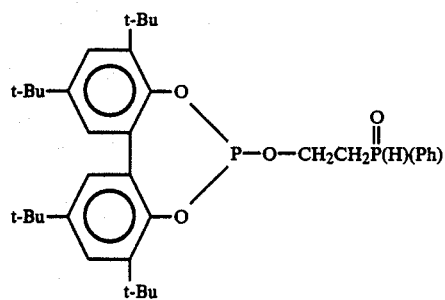
-continued
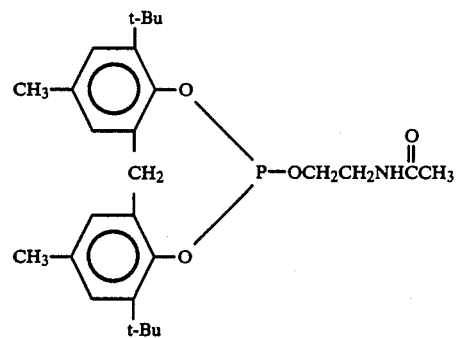
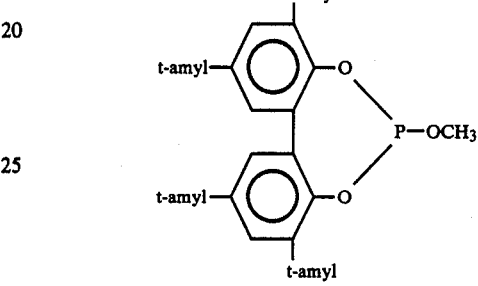
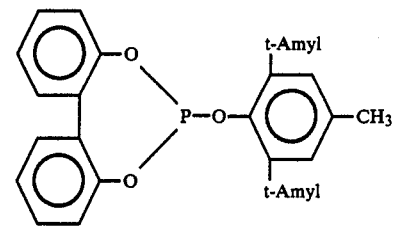
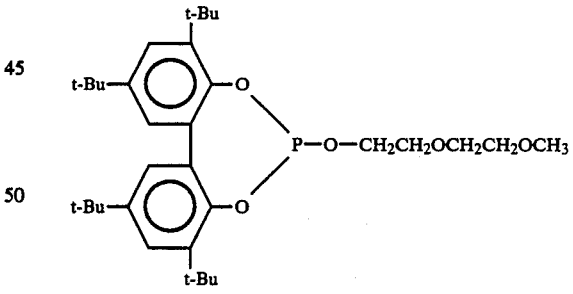
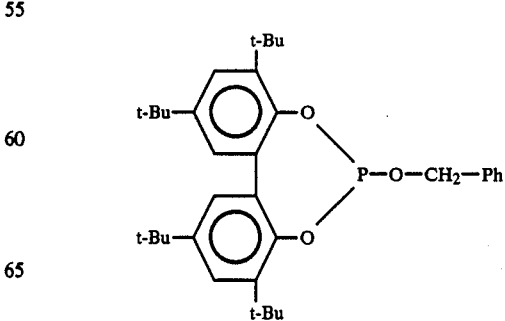

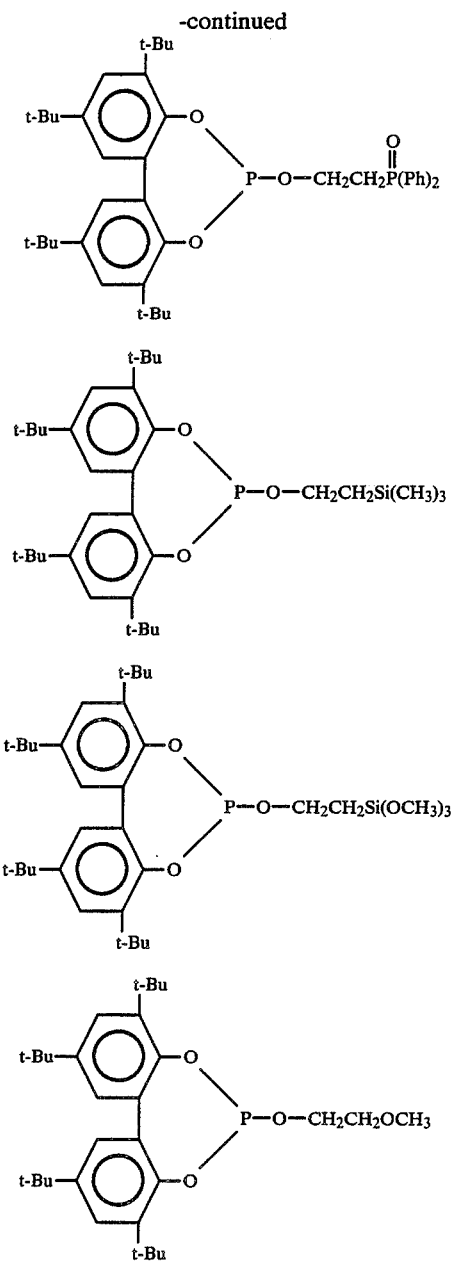

In the above diorganophosphite formulas t-Bu represents a tertiary butyl radical, Ph represents a phenyl (—C₆H₅) radical and (—C₉H₁₉) represents branched mixed nonyl radicals. The most preferred diorganophosphite ligands employable in this invention are those of the formulas

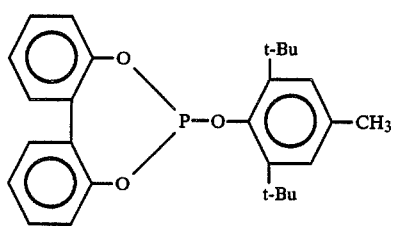

1,1′-biphenyl-2,2′-diyl-(2,6-di-t-butyl-4-methylphenyl)phosphite

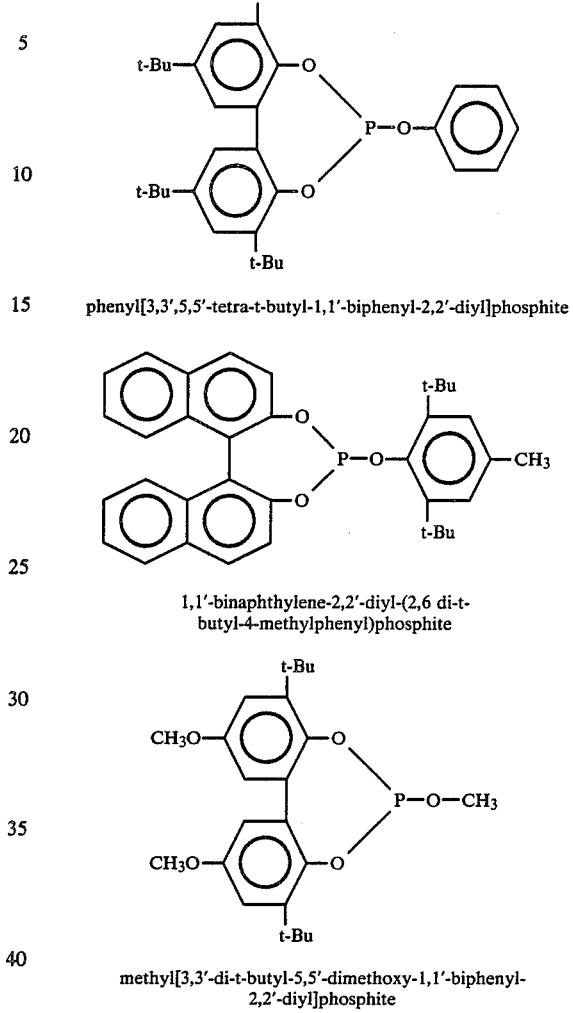

phenyl[3,3′,5,5′-tetra-t-butyl-1,1′-biphenyl-2,2′-diyl]phosphite 1,1′-binaphthylene-2,2′-diyl-(2,6 di-t-butyl-4-methylphenyl)phosphite methyl[3,3′-di-t-butyl-5,5′-dimethoxy-1,1′-biphenyl-2,2′-diyl]phosphite As noted above the diorganophosphite ligands defined above are employed in this invention as both the phosphorus ligand of the Group VIII transition metal complex catalyst, as well as, the free phosphorus ligand that is preferably present in the reaction medium of the process of this invention. In addition, it is to be understood that while the phosphorus ligand of the Group VIII transition metal-diorganophosphite complex catalyst and excess free phosphorus ligand preferably present in a given process of this invention are normally the same type of diorganophosphite ligand, different types of diorganophosphite ligands, as well as, mixtures of two or more different diorganophosphite ligands may be employed for each purpose in any given process, if desired.

As in the case of prior art Group VIII transition metal-phosphorus complex catalysts, the Group VIII transition metal-diorganophosphite complex catalysts of this invention may be formed by methods known in the art. For instance, preformed Group VIII transition metal hydridocarbonyl (diorganophosphite) catalysts may possibly be prepared and introduced into the reaction medium of a hydroformylation process. Most preferably, the Group VIII transition metal-diorganophosphite complex catalysts of this invention can be derived from a metal catalyst precursor which may be introduced into the reaction medium for in situ formation of the active catalyst. For example, rhodium catalyst precursors such as rhodium dicarbonyl acetylacetonate, $Rh_2O_3$, $R_4(CO)_{12}$, $Rh_6(CO)_{16}$, $Rh(NO_3)_3$ and the like may be introduced into the reaction medium along with the diorganophosphite ligand for the in situ formation of the active catalyst. In a preferred embodiment rhodium dicarbonyl acetylacetonate is employed as a rhodium precursor and reacted in the presence of a solvent with the diorganophosphite to form a catalytic rhodium carbonyl diorganophosphite acetylacetonate precursor which is introduced into the reactor along with excess free diorganophosphite ligand for the in situ formation of the active catalyst. In any event, it is sufficient for the purpose of this invention to understand that carbon monoxide, hydrogen and diorganophosphite are all ligands that are capable of being complexed with the Group VIII transition metal, e.g. rhodium and that an active Group VIII transition metal-diorganophosphite catalyst is present in the reaction medium under the conditions of the carbonylation and more preferably hydroformylation process.

Accordingly, the Group VIII transition metal-diorganophosphite complex catalysts of this invention may be defined as consisting essentially of a Group VIII transition metal complexed with carbon monoxide and a diorganophosphite ligand. Of course, it is to be understood that the catalyst terminology "consisting essentially of" is not meant to exclude, but rather include hydrogen complexed with the metal particularly in the case of rhodium catalyzed hydroformylation, in addition to carbon monoxide and the diorganophosphite ligand. Moreover, as noted above such terminology is also not meant to exclude the possibility of other organic ligands and/or anions that might also be complexed with the metal. However, such catalyst terminology preferably is meant to exclude other materials in amounts which unduly adversely poison or unduly deactivate the catalyst and thus rhodium most desirably is free of contaminants such as rhodium bound halogen e.g. chlorine, and the like. As noted, the hydrogen and/or carbonyl ligands of an active rhodium-diorganophosphite complex catalyst may be present as a result of being ligands bound to a precursor catalyst and/or as a result of in-situ formation e.g. due to the hydrogen and carbon monoxide gases employed in a hydroformylation process.

Moreover, like prior art Group VIII transition metal phosphorus ligand complex catalysts it is clear that the amount of complex catalyst present in the reaction medium of a given process of this invention need only be that minimum amount necessary to provide the given Group VIII transition metal concentration desired to be employed and which will furnish the basis for at least that catalytic amount of Group VIII transition metal necessary to catalyze the particular carbonylation process desired. Moreover, one of the benefits of this invention is the generally improved catalytic activity obtainable by the use of the diorganophosphite ligands employable herein. Such improved catalytic activity can translate into a considerable processing asset, particularly when rare and expensive Group VIII transition metals such as rhodium are to be employed, since lower reaction temperatures and/or lower amounts of catalytically active metal may be employed to achieve a desired rate of productivity than may be possible when less active catalysts are employed. In general, Group VIII transition metal concentrations in the range of from about 10 ppm to about 1000 ppm, calculated as free metal, should be sufficient for most carbonylation processes. Moreover, in the rhodium catalyzed hydroformylation processes of this invention, it is generally preferred to employ from about 10 to 500 ppm of rhodium and more preferably from 25 to 350 ppm of rhodium, calculated as free metal.

The olefinic starting material reactants encompassed by the processes of this invention can be terminally or internally unsaturated and be of straight-chain, branched-chain or cyclic structure. Such olefins can contain from 2 to 20 carbon atoms and may contain one or more ethylenic unsaturated groups. Moreover, such olefins may contain groups or substituents which do not essentially adversely interfere with the hydroformylation process such as carbonyl, carbonyloxy, oxy, hydroxy, oxycarbonyl, halogen, alkoxy, aryl, haloalkyl, and the like. Illustrative olefinic unsaturated compounds include alpha olefins, internal olefins, alkyl alkenoates, alkenyl alkanoates, alkenyl alkyl ethers, alkenols, and the like, e.g. ethylene, propylene, 1-butene, 1-pentene, 1-hexene, 1-octene, 1-decene, 1-dodecane, 1-octadecene, 2-butene, 2-methyl propene (isobutylene), isoamylene, 2-pentene, 2-hexene, 3-hexene, 2-heptene, cyclohexene, propylene dimers, propylene trimers, propylene tetramers, 2-ethyl-1-hexene, styrene, 3-phenyl-1-propene, 1,4-hexadiene, 1,7 octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl-7-octenoate, 3-butenenitrile, 5-hexenamide, and the like. Of course, it is understood that mixtures of different olefinic starting materials can be employed, if desired, by the hydroformylation process of the subject invention. More preferably the subject invention is especially useful for the production of aldehydes, by hydroformylating alpha olefins containing from 2 to 20 carbon atoms and internal olefins containing from 4 to 20 carbon atoms as well as starting material mixtures of such alpha olefins and internal olefins. The most preferred olefin starting materials are butene-1, butene-2 (cis and-/or trans), isobutene and various mixture thereof.

The carbonylation and preferably hydroformylation process of this invention is also preferably conducted in the presence of an organic solvent for the Group VIII transition metal-diorganophosphite complex catalyst. Any suitable solvent which does not unduly adversely interfere with the intended carbonylation process can be employed and such solvents may include those heretofore commonly employed in known Group VIII transition metal catalyzed processes. By way of illustration suitable solvents for rhodium catalyzed hydroformylation processes include those disclosed e.g. in U.S. Pat. Nos. 3,527,809 and 4,148,830. Of course, mixtures of one more different solvents may be employed if desired. In general, in rhodium catalyzed hydroformylation it is preferred to employ aldehyde compounds corresponding to the aldehyde products desired to be produced and/or higher boiling aldehyde liquid condensation by-products as the primary solvent such as the higher boiling aldehyde liquid condensation by-products that are produced in situ during the hydroformylation process. Indeed, while one may employ, if desired, any suitable solvent at the start up of a continuous process (aldehyde compounds corresponding to the desired aldehyde products being preferred), the primary solvent will normally eventually comprise both aldehyde products and higher boiling aldehyde liquid condensation by-products due to the nature of such continuous processes. Such aldehyde condensation by-products can also be preformed if desired and used accordingly. Moreover, such higher boiling aldehyde condensation by-products and methods for their preparation are more fully described in U.S. Pat. Nos. 4,148,830 and 4,247,486. Of course, it is obvious that the amount of solvent employed is not critical to the subject invention and need only be that amount sufficient to provide the reaction medium with the particular Group VIII transition metal concentration desired for a given process. In general, the amount of solvent when employed may range from about 5 percent by weight up to about 95 percent by weight or more based on the total weight of the reaction medium.

It is further generally preferred to carry out the carbonylation and especially the hydroformylation process of this invention in a continuous manner. Such types of continuous processes are well known in the art and may involve e.g. hydroformylating the olefinic starting material with carbon monoxide and hydrogen in a liquid homogeneous reaction medium comprising a solvent, the Group VIII transition metal-diorganophosphite catalyst, and free diorganophosphite ligand; supplying make-up quantities of the olefinic starting material, carbon monoxide and hydrogen to the reaction medium; maintaining reaction temperature and pressure conditions favorable to the hydroformylation of the olefinic starting material; and recovering the desired aldehyde hydroformylation product in any conventional manner desired. While the continuous process can be carried out in a single pass mode, i.e. wherein a vaporous mixture comprising unreacted olefinic starting material and vaporized aldehyde product is removed from the liquid reaction medium from whence the aldehyde product is recovered and make-up olefinic starting material, carbon monoxide and hydrogen are supplied to the liquid reaction medium for the next single pass through without recycling the unreacted olefinic starting material, it is generally desirable to employ a continuous process that involves either a liquid and/or gas recycle procedure. Such types of recycle procedures are well known in the art and may involve the liquid recycling of the Group VIII transition metal-diorganophosphite complex catalyst solution separated from the desired aldehyde reaction product, such as disclosed e.g. in U.S. Pat. No. 4,148,830 or a gas recycle procedure such as disclosed e.g. in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process.

The desired aldehyde product may be recovered in any conventional manner such as described, e.g. in U.S. Pat. Nos. 4,148,830 and 4,247,486. For instance, in a continuous liquid catalyst recycle process the portion of the liquid reaction solution (containing aldehyde product, catalyst, etc.) removed from the reactor can be passed to a vaporizer/separator wherein the desired aldehyde product can be separated via distillation, in one or more stages, under normal, reduced or elevated pressure, from the liquid reaction solution, condensed and collected in a product receiver, and further purified if desired. The remaining non-volatilized catalyst containing liquid reaction solution may then be recycled back to the reactor as may if desired any other volatile materials, e.g. unreacted olefin, together with any hydrogen and carbon monoxide dissolved in the liquid reaction solution after separation thereof from the condensed aldehyde product, e.g. by distillation in any conventional manner. In general, it is preferred to separate the desired aldehyde product from the rhodium catalyst containing product solution under reduced pressure and at low temperatures such as below 150° C. and more preferably below 130° C.

As noted above, the carbonylation process and especially the hydroformylation process of this invention is preferably carried out in the presence of free diorganophosphite ligand, i.e. ligand that is not complexed with the Group VIII transition metal of the metal complex catalyst employed. Thus the free diorganophosphite ligand may correspond to any of the above defined diorganophosphite ligands discussed above. However, while it is preferred to employ a free diorganophosphite ligand that is the same as the diorganophosphite ligand of the Group VIII transition metal-diorganophosphite complex catalyst such ligands need not be the same in a given process, but can be different if desired. While the carbonylation and preferably hydroformylation process of this invention may be carried out in any excess amount of free diorganophosphite ligand desired, e.g. at least one mole of free diorganophosphite ligand per mole of Group VIII transition metal present in the reaction medium, it has been found that in rhodium catalyzed hydroformylation large amounts of free diorganophosphite ligand are not necessary for catalytic activity and/or catalyst stabilization, and generally retard the activity of the rhodium catalyst. Accordingly, in general amounts of diorganophosphite ligand of from about 4 to about 50, and preferably from about 6 to about 25, moles per mole of Group VIII transition metal (e.g. rhodium) present in the reaction medium should be suitable for most purposes, particularly with regard to rhodium catalyzed hydroformylation; said amounts of diorganophosphite ligand employed being the sum of both the amount of diorganophosphite that is bound (complexed) to the Group VIII transition metal present and the amount of free (non-complexed) diorganophosphite ligand present. Of course, if desired, make-up diorganophosphite ligand can be supplied to the reaction medium of the hydroformylation process, at any time and in any suitable manner, to maintain a predetermined level of free ligand in the reaction medium.

The ability to carry out the process of this invention in the presence of free diorganophosphite ligand is an important beneficial aspect of this invention in that it removes the criticality of employing very low precise concentrations of ligand that may be required of certain complex catalysts whose activity may be retarded when even any amount of free ligand is also present during the process, particularly when large scale commercial operations are involved, thus helping to provide the operator with greater processing latitude.

The reaction conditions for effecting a carbonylation and more preferably a hydroformylation process of this invention may be those heretofore conventionally used and may comprise a reaction temperature of from about 45° C. to about 200° C. and pressures ranging from about 1 to 10,000 psia. While the preferred carbonylation process is the hydroformylation of olefinically unsaturated compounds and more preferably olefinic hydrocarbons, with carbon monoxide and hydrogen to produce aldehydes, it is to be understood that the Group VIII transition metal-diorganophosphite complexes of this invention may be employed as catalysts in any other type of prior art carbonylation process to obtain good results. Moreover, while such other prior carbonylation art processes may be performed under their usual conditions, in general it is believed that they may be performed at lower temperatures than normal and/or at a higher rate of reaction due to the Group VII transition metal-diorganophosphite complex catalysts of this invention.

As noted the more preferred process of this invention involves the production of aldehydes via hydroformylation of an olefinic unsaturated compound with carbon monoxide and hydrogen in the presence of a Group VIII transition metal-diorganophosphite complex catalyst and free diorganophosphite ligand. While it may be possible to produce aldehyde products having a high normal (straight chain) to branched chain aldehyde product ratio, e.g. on the order of about 5 to 1 or greater, by the hydroformylation process of this invention, in general the preferred hydroformylation will be that process which is most efficient in producing aldehyde product rich in branched chain aldehyde, i.e. aldehyde product having a low normal (straight chain) aldehyde to branched chain aldehyde product ratio, e.g. on the order of 5 moles or less of n-aldehyde product to 1 mole of branched aldehyde product. Moreover, a unique feature of the present invention is the overall processing latitude afforded in controlling the aldehyde product selectivity that is provided by the use of the diorganophosphite ligands employable herein. For instance, due to isomerization of the olefin starting material during hydroformylation that occurs with the use of the diorganophosphite ligands employable herein, one may control or preselect the particular richness of branched aldehyde in the product desired (i.e. preselect the particular desired ratio of normal to branched aldehyde product), which is in marked contrast to hydroformylations that employ phosphorus ligands which show little or no ability to permit isomerization of the olefin starting material during such reactions leaving one with little or no ability to control the ratio of normal to branched chain aldehyde product that may be desired.

For example, alpha-olefins such as butene-1 may be readily hydroformylated by the process of this invention to produce aldehyde products having straight chain to branched chain aldehyde product ratios of less than 5 to 1, preferably less than 3 to 1 and more preferably about 2 to 1. On the other hand internal olefins may be surprisingly hydroformylated by the process of this invention to obtain aldehyde products that are even richer in their branched chain isomers. For instance pure butene-2 can be hydroformylated to obtain more 2-methyl-butyraldehyde, i.e. aldehyde products wherein the ratio of n-valeraldehyde to 2-methylbutyraldehyde is about 2 to 1 or less, preferably less than 1 to 1 and more preferably less than 0.5 to 1. Such processing latitude of the present invention, provided in part by isomerization of the olefin starting material during hydroformylation and the choice of the diorganophosphite ligand employed, is especially useful in those instances when a particular optimization of the branched chain aldehyde product is desirable. For instance, since 2-methylbutyraldehyde is the precursor of isoprene which is used to produce synthetic rubber, the ability to produce essentially only 2-methylbutyraldehyde directly by the hydroformylation process of this invention is extremely beneficial to the art in that it greatly facilitates the refining operation (separation from n-valeraldehyde) and allows for the production of higher amounts of desired 2-methylbutyraldehyde product per given amount of butene-2 starting material. On the other hand, there are clearly instances when it may be desirable that the aldehyde product need not be quite so rich in branched chain aldehyde, but may comprise a slightly higher normal to branched chain aldehyde product ratio such as when the aldehydes are employed as precursors for alcohols and acids which in turn may find utility in such diverse fields as synthetic lubricants, solvents, paints, fertilizers, and the like.

Likewise mixtures of alpha-olefins and internal olefins can also be readily hydroformylated by the process of this invention to obtain aldehyde products that are rich in their branched chain isomers. For instance starting material mixtures of butene-1 and butene-2 can readily be hydroformylated to obtain aldehyde products wherein the ratio of straight chain aldehyde to branched chain aldehyde is about 3 to 1 or less and more preferably about 2 to 1 or less. The ability to hydroformylate both types of olefins concurrently with comparable facility from the same starting material mixture is highly beneficial to the art since such mixed alpha olefin and internal olefin starting materials are readily available and are the most economical olefin feedstocks. Moreover, the versatility of the diorganophosphite ligands employable herein lend themselves readily to the continuous hydroformylation of both alphaolefins and internal olefins wherein different reactors in series may be employed. Such aiblity not only provides one with the processing latitude of further hydroformylating in the second reactor any unreacted olefin passed to it from the first reactor but also allows one, if desired, to optimize the reaction conditions for hydroformylation of e.g. the alpha-olefin in the first reactor, while also optimizing the reaction conditions for the hydroformylation of e.g. the internal olefin in the second reactor.

Of course, it is to be understood that while the optimization of the reaction conditions necessary to achieve the best results and efficiency desired are dependent upon one's experience in the utilization of the subject hydroformylation invention, only a certain measure of experimentation should be necessary to ascertain those conditions which are optimum for a given situation and such should be well within the knowledge of one skilled in the art and easily obtainable by following the more preferred aspects of this invention as explained herein and/or by simple routine experimentation.

For instance, the total gas pressure of hydrogen, carbon monoxide and olefinic unsaturated starting compound of the hydroformylation process of this invention may range from about 1 to about 10,000 psia. More preferably, however, in the hydroformylation of olefins to produce aldehydes it is preferred that the process be operated at a total gas pressure of hydrogen, carbon monoxide and olefinic unsaturated starting compound of less than about 1500 psia. and more preferably less than about 500 psia. The minimum total pressure of the reactants is not particularly critical and is limited predominately only by the amount of reactants necessary to obtain a desired rate of reaction. More specifically the carbon monoxide partial pressure of the hydroformylation process of this invention is preferably from about 1 to about 120 psia. and more preferably from about 3 to about 90 psia, while the hydrogen partial pressure is preferably about 15 to about 160 psia and more preferably from about 30 to about 100 psia. In general $H_2:CO$ molar ratio of gaseous hydrogen to carbon monoxide may range from about 1:10 to 100:1 or higher, the more preferred hydrogen to carbon monoxide molar ratio being from about 1:1 to about 10:1.

Further as noted above the hydroformylation process of this invention may be conducted at a reaction temperature from about 45° C. to about 200° C. The preferred reaction temperature employed in a given process will of course be dependent upon the particular olefinic starting material and metal catalyst employed as well as the efficiency desired. While conventional carbonylation and/or hydroformylation reaction temperatures may also be employed herein, the operation of the hydroformylation process of this invention can be optimized in a surprisingly lower temperature range than heretofore preferably advance by the prior art.

For example, compared to prior art rhodium catalyzed hydroformylation systems, the improved catalytic activity and/or stability afforded by the rhodium-diorganophosphite complex catalysts of this invention is particularly unique for achieving high rates of selective hydroformylation at comparatively low reaction temperatures. In general, hydroformylations at reaction temperatures of about 50° C. to about 120° C. are preferred for all types of olefinic starting materials. More preferably, $\alpha$-olefins can be effectively hydroformylated at a temperature of from about 60° C. to about 110° C. while even less reactive olefins than conventional $\alpha$-olefins such as isobutylene and internal olefins as well as mixtures of $\alpha$-olefins and internal olefins are effectively and preferably hydroformylated at a temperature of from about 70° C. to about 120° C. Indeed in the rhodium-catalyzed hydroformylation process of this invention no substantial benefit is seen in operating at reaction temperatures much above 120° C. and such is considered to be less desirable, due to possible catalyst activity decline and/or rhodium losses that may be caused by the higher temperatures.

As outlined herein the carbonylation and more preferably hydroformylation process of this invention can be carried out in either the liquid or gaseous state and involve a continuous liquid or gas recycle system or combination of such systems. Preferably the rhodium catalyzed hydroformylation of this invention involves a continuous homogeneous catalysis process wherein the hydroformylation is carried out in the presence of both free diorganophosphite ligand and any suitable conventional solvent as further outlined herein. Such types of continuous hydroformylation systems and methods for carrying them out are well known in the art and thus need not be particularly detailed herein.

While the hydroformylation process of this invention may be carried out employing any olefinic unsaturated starting material such as already noted herein, the preferred rhodium catalyzed hydroformylation process of this invention has been found to be particularly effective in converting olefins such as $\alpha$-olefins having from 2 to 20 carbon atoms and internal olefins having from 4 to 20 carbon atoms, as well as mixtures of such olefins, to their corresponding aldehyde products. Moreover, the hydroformylation of olefins that are normally less reactive than their corresponding sterically unhindered $\alpha$-olefins, such as isobutylene and internal olefins is an even more preferred aspect of this invention, as is the hydroformylation of mixtures of $\alpha$-olefins and internal olefins.

In general the use of the diorganophosphite ligands provide a far more catalytically active and stable rhodium catalyst for the hydroformylation of olefins, especially internal and other such less reactive sterically hindered olefins e.g. isobutylene than obtainable with conventional triorganophosphine ligands, thus allowing for greater rates and/or increased amounts of aldehyde production at much lower reaction temperatures. The rhodium catalyzed hydroformylation process of this invention of mixtures of $\alpha$-olefins and internal olefins is further unique in that the subject process of this invention results in a high degree of aldehyde product production from both types of olefins in the starting material, in contrast to those prior art processes that promote hydroformylation of primarily only the more reactive sterically unhindered α-olefins. Of course, it is to be understood that the proportional make up of the mixed olefin starting materials employable in this invention is not critical and any desired proportional amounts of such olefins may be employed in the starting olefin mixture. In general, it is especially preferred to hydroformylate mixtures of butene-1 and butene-2 (cis and/or trans), which mixtures may also optionally contain isobutene, in order to obtain proportionate product mixtures of valeraldehyde, 2-methylbutyraldehyde and optionally 3-methylbutyraldehyde.

Further, undesirable side reactions that may occur in rhodium catalyzed hydroformylation may be curtailed by the use of the diorganophosphite ligands of this invention such as, undue aldehyde by-product heavies formation, as well as ligand stability towards the aldehyde product. For example, while the use of the diorganophosphite ligands employable herein may curtail undue higher boiling aldehyde condensation by-product formation, it is axiomatic that in commercial continuous hydroformylation of such olefins the concentration of such higher boiling aldehyde condensation by-products (e.g. dimeric and trimeric aldehydes) will eventually continue to build over a period of time until it is finally desirable or necessary to remove at least a portion of such higher boiling aldehyde condensation by-products, as described e.g. in U.S. Pat. Nos. 4,148,430 and 4,247,486. In such an occurrance it is desirable that phosphorus ligand which is also present (preferably in an excess amount) have a lower vapor pressure (higher boiling point) than that of the aldehyde condensation by-products so that the ligand will not be lost or depleted when such aldehyde condensation by-products are removed. For example, volatility is related to molecular weight and is inversely proportional to molecular weight within a homologous series. Accordingly, it is desirable to employ a diorganophosphite ligand whose molecular weight exceeds that of the aldehyde by-product trimer corresponding to the aldehyde being produced. For instance, since the molecular weight of valeraldehyde trimer is about 258 ($C_{15}H_{30}O_3$) and all the preferred diorganophosphites of this invention exceed 330 in molecular weight, it is clear that the diorganophosphites of this invention are especially suitable for use in hydroformylating butene-1 and/or butene-2, is as much as there should not be any considerable loss of the diorganophosphite ligand during product aldehyde and higher boiling aldehyde by-product removal, as might predictably be the case when a different phosphorus ligand having a lower molecular weight (e.g. higher vapor pressure or lower boiling point) than the higher boiling aldehyde by-product is employed (and which would require additional processing steps if recovery and reuse of the phosphorus ligand is desired).

Further, while triorganophosphite ligands in general will provide a metal-complex catalyst with sufficient activity to hydroformylate internal olefins, experience has shown that their use, particularly with regard to continuous hydroformylation, has been less than satisfactory. This drawback in employing triorganophosphites is believed due to their very high affinity for reacting with aldehydes, the product of which has been found to readily hydrolyze to a corresponding hydroxy alkyl phosphonic acid, as shown by the following skeletal reaction mode:

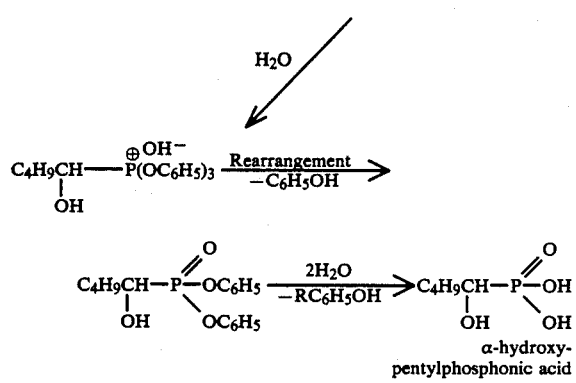

α-hydroxy-pentylphosphonic acid

Moreover, the formation of such acid is an autocatalytic process, thus rendering triorganophosphite ligands even more susceptible to the production of such undesirable acid by-products, particularly in continuous rhodium catalyzed liquid recycle hydroformylation wherein contact between the phosphite ligand and aldehyde product is prolonged. Surprisingly, the diorganophosphite ligands employable in this invention have been found in general to be far less moisture sensitive and far less reactive toward forming such phosphonic acid than conventional triorganophosphites, thus providing a more prolonged stable and active continuous rhodium catalyzed liquid recycle hydroformylation than may be possible with triorganophosphite ligands. Such is not to say however, that hydroxy alkyl phosphonic acid by-product will not be eventually formed over the course of the continuous rhodium catalyst liquid recycle hydroformylation process of this invention. However, the accumulation of such undesirable hydroxy alkyl phosphonic acid, during a continuous recycle hydroformylation process of this invention, takes place at a much slower rate than when triorganophosphite ligands are employed, which allows for a longer and more efficient continuous operation. For instance, rapid decomposition of the phosphite ligand may not only adversely effect catalyst activity and/or stability, but obviously leads to a quick loss of the phosphite ligand that must be replaced with make-up phosphite ligand, as well as helping to further promote the autocatalytic formation of the undesirable hydroxy alkyl phosphonic acid which is often insoluble in the general liquid hydroformylation reaction medium. Consequently rapid and high build-up of such hydroxy alkyl phosphonic acid can lead to precipitation of the acid to an obviously undesirable gellatinous by-product, which may plug and/or foul the recycle lines of a continuous liquid reaction system, thus necessitating periodic processing shut-downs or stoppages for removal of such acid and or precipitate from the system by an appropriate method e.g. by extraction of the acid with a weak base, e.g. sodium bicarbonate.

Moreover, it has been surprisingly found that the above mentioned disadvantages attendent with such hydroxy alkyl phosphonic acid by-product may be effectively and preferably controlled by passing the liquid reaction effluent stream of a continuous liquid recycle process either prior to or more preferably after separation of the aldehyde product therefrom through any suitable weakly basic anion exchange resin, such as a bed of amine-Amberlyst® resin, e.g. Amberlyst® A-21, and the like, to remove some or all of the undesirable hydroxy alkyl phosphonic acid by-product that might be present in the liquid catalyst containing stream prior to its reincorporation into the hydroformylation reactor. Of course if desired, more than one such basic anion exchange resin bed, e.g. a series of such beds, may be employed and any such bed may be easily removed and/or replaced as required or desired. Alternatively if desired, any part or all of the hydroxy alkyl phosphonic acid contaminated catalyst recycle stream may be periodically removed from the continuous recycle operation and the contaminated liquid so removed treated in the same fashion as outlined above, to eliminate or reduce the amount of hydroxy alkyl phosphonic acid contained therein prior to reusing the catalyst containing liquid in the hydroformylation process. Likewise, any other suitable method for removing such hydroxy alkyl phosphonic acid by-product from the hydroformylation process of this invention may be employed herein if desired.

Accordingly another preferred and novel aspect of the subject invention is directed to an improved continuous hydroformylation process for producing aldehydes which comprises reacting an olefin with carbon monoxide and hydrogen in the presence of a liquid medium containing a solubilized rhodium-organophosphite complex catalyst, a solvent, free organophosphite ligand, and aldehyde product, the improvement comprising minimizing decomposition of the free organophosphite ligand by (a) removing a stream of said liquid medium from the hydroformylation reaction zone, (b) treating the liquid medium so removed with a weakly basic anion exchange resin and (c) returning the treated reaction medium to the hydroformylation reaction zone.

Such treatment of the liquid medium with a weakly basic anion exchange resin comprises passing the liquid medium, i.e., liquid reaction effluent stream, after removal of said stream from the hydroformylation reaction zone, either prior to and/or after separation of aldehyde product therefrom, through a weakly basic anion exchange resin bed.

Any suitable weakly basic anion exchange resin bed may be employed herein. Illustrative weakly basic anion exchange resin beds employable herein may include, e.g., crosslinked tertiary amine polystyrene anion exchange resins of the gel or macroreticular type, such as a bed of amine-Amberlyst® resin and more preferably, Amberlyst® A-21, which comprises a crosslinked polystyrene backbone with pendant benzyl dimethylamino [—$C_6H_4$—$CH_2$—$N(CH_3)_2$] functional groups. Such types of weakly basic anion exchange resin beds and/or methods for their manufacture are well known in the art.

As noted above decomposition of the organophosphite ligand may be effectively controlled and minimized by the preferred treatment of this invention which as postulated removes some or all of the undesirable hydroxy alkyl phosphonic acid by-product that might be present in the liquid medium as a result of in situ build-up over the course of the hydroformylation reaction and which is an autocatalytic material for decomposition of the organophosphite, e.g., via the side reaction of phosphite ligand and aldehyde product.

While small amounts of such hydroxyalkyl phosphonic acids in hydroformylation reaction mediums are difficult to analyze for by standard analytical methods such as gas chromatography or liquid chromatography due in part to the high boiling and polar nature of such acids; $^{31}P$ NMR (Nuclear Magnetic Resonance) can be successfully employed to detect such acids in amounts as low as about 100 ppm by weight. For example, one need only determine the detectable resonance peak (chemical shift in ppm relative to external $H_3PO_4$) via $^{31}P$ NMR for a comparative synthetic solution containing 100 ppm of the hydroxyalkyl phosphonic acid, then monitor the hydroformylation reaction medium of the process in question for evidence of the corresponding acid resonance peak via the same $^{31}P$ NMR technique. Thus while the subject improvement generically encompasses a process for removal of hydroxyalkyl phosphonic acid from a liquid hydroformylation reaction medium that already contains more than merely a trace amount of such acid to thereby minimize further decomposition of the organophosphite ligand, experience has shown that decomposition of the organophosphite ligand can be very rapid when the amount of hydroxy alkyl phosphonic acid is allowed to build up to more than a trace amount. Thus the preferred process of this invention is one in which the liquid medium to be treated does not even contain a readily detectable amount of such hydroxy alkyl phosphonic acid and such is accomplished by beginning said treatment of the liquid medium prior to the build-up of a readily detectable amount (e.g. 100 ppm) by weight of such hydroxy alkyl phosphonic acid via $^{31}P$ NMR so as to remove said hydroxy alkyl phosphonic acid as it is being formed. Accordingly, while this invention encompasses both intermittent and continuous treatment of the liquid medium to minimize organophosphite ligand decomposition, continuous treatment of the liquid medium during the hydroformylation process is preferred.

Moreover the minimization of the degree of decomposition of the organophosphite ligand obtainable by the process of this invention can be readily observed and quantitatively calculated if desired, by determining in a given process, the amount of organophosphite ligand remaining and/or lost in the hydroformylation reaction medium, from that amount initially employed, after a given period of time of the continuous hydroformylation process, in contrast to the amount of organophosphite ligand remaining and/or lost in a corresponding continuous hydroformylation process carried out under the same conditions, but without employing the weakly basic anion exchange resin treatment outlined herein.

Accordingly minimizing the degree of decomposition of the organophosphite ligand by preventing and/or slowing down the rate of reaction between such ligands and aldehyde product, allows for a longer and more efficient continuous operation than a comparative hydroformylation process carried out in the absence of a weakly basic anion exchane resin treatment. Moreover in addition to preventing and/or minimizing ligand and aldehyde product loss, the subject treatment may also help sustain the rate of hydroformylation and aldehyde product ratio desired over a longer period of time, as well as help maintain catalyst activity and/or stability, which may be adversely effected by rapid decomposition of the organophosphite ligand. Further the drawback of rapid and high build-up of such hydroxy alkyl phosphonic acid which can lead to precipitation of the acid to an obviously undesirable gellatinous by-product and which may plug and/or foul the recycle lines of a continuous hydroformylation system can be overcome by the process of this invention.

The employment of a weakly basic anion exchange resin as described in this invention is indeed unique and surprising, since such resins, e.g., Amberlyst ® A-21 are known to be highly reactive with carboxylic acids, which are also minor oxo reaction by-products. This property alone would suggest that the use of such resins would not be a practical means for the removal of phosphonic acid from a hydroformylation process stream, since it suggests that the acid neutralization ability of the resin would be consumed too rapidly by the carboxylic acid generated by the hydroformylation. However, it has been surprisingly found that the carboxylic acid neutralized form of Amberlyst ® A-21 resin is still basic enough, to remove the stronger hydroxyalkyl phosphonic acid from hydroformylation streams even in the presence of carboxylic acids. Moreover, experience as shown that the addition of tertiary amines (such as dimethylaniline, triethanolamine, proton sponge, etc.) to phosphite ligand promoted rhodium complex hydroformylation catalysts can cause rapid rhodium precipitation in the form of black solids. Likewise, Amberlyst ® A-21 resin itself when added to a hydroformylation reaction medium under hydroformylation conditions has been found to cause rhodium precipitation on the resin surface and pores. It is therefore clearly unexpected and fortunate that the use of a weakly basic anion exchange resin as described herein, e.g., Amberlyst ® A-21 on a liquid medium stream that has been removed from the hydroformylation reaction zone does not adversely precipitate rhodium or unduly adversely affect the rhodium catalyst and process in any significant adverse manner, such as by increasing the rate of aldehyde heavies formation.

It is to be noted, however, that commercial grade weakly basic anion exchange resin beds, such as Amberlyst ® A-21, may contain halide impurities, e.g. chloride contaminates, which are known to poison (adversely affect) rhodium complex hydroformylation catalysts. Thus it is preferred that the weakly basic anion exchange resin beds employable herein be at least substantially free of halogen contaminates and more preferably essentially or entirely free from such halogen contaminates. Removal of such halogen contaminates, as well as any other undesirable contaminates, from such weakly basic anion exchange resin beds prior to their use may be readily accomplished by conventional washing techniques that are well known in the art.

As further noted herein the treatment of the liquid medium containing a solubilized rhodium-organophosphite complex catalyst, a solvent, free organophosphite ligand and aldehyde product must take place outside of the hydroformylation reaction zone of the continuous hydroformylation process and the medium so treated returned to the hydroformylation reactor. Accordingly, this treatment is adaptable to both well known continuous type gas and/or liquid recycle hydroformylation processes.

For example, in a continuous gas recycle hydroformylation process, the treatment of this invention may be carried out by intermittently or continuously withdrawing a portion e.g. slip stream of the liquid reaction mixture from the reactor, passing it through a weakly basic anion exchange resin bed and returning the so treated slip stream of the liquid reaction mixture to the reactor. In a liquid recycle hydroformylation process, the liquid medium removed from the reactor can be passed through the weakly basic anion exchange resin bed at any point throughout the recycle process. For instance, in a liquid recycle hydroformylation procedure, it is common place to continuously remove a portion of the liquid reaction product medium from the reactor and the desired aldehyde product recovered in one or more distillation stages e.g. by passing said liquid medium to a vaporizor/separator wherein the desired product is distilled and separated from said medium and eventually condensed and recovered. The remaining liquid residue obtained upon such separation of aldehyde product, which residue contains the rhodium-organophosphite catalyst, solvent, free organophosphite ligand and some undistilled aldehyde product is then recycled back to the reactor along with whatever by-products e.g. hydroxy alkyl phosphonic acid that might also be present in said recycled residue. While the treatment of such liquid mediums, of such continuous liquid recycle hydroformylation processes, according to this invention can be carried out prior to and/or subsequent to the separation of aldehyde product therefrom, it is preferred to carry out the treatment of this invention after the removal or separation of aldehyde product. For example, it is preferred to position the weakly basic anion exchange resin bed after the aldehyde product vaporizor/separator so that what is passed through the weakly basic anion exchange resin bed is the catalyst containing liquid recycle residue as explained above. In addition to being a more convenient and economical position in the reaction system for utilizing such a weakly basic anion exchange resin bed, it is believed that such positioning minimizes the amount of the hydridic form of the rhodium catalyst which is to come in contact with the weakly basic anion exchange resin, and it is the hydridic form of the rhodium catalyst that is believed to be the reactive form which in the presence of e.g. amines may form insoluble anionic rhodium clusters. It is believed that the hydridic form of the rhodium catalyst is changed to a less reactive non-hydridic form as it passes through the aldehyde product recovery distillation stage, e.g. vaporizor/separator, of the hydroformylation process and that this less reactive rhodium catalyst form is less likely to cause process complications when contacted with the weakly basic anion exchange resin.

In view of the fact that the weakly basic anion exchange resin treatment encompassed herein is designed to obtain a desired improvement in at least minimizing the degree of decomposition of the organophosphite ligand employed in the hydroformylation process over that experienced in the absence of such a resin treatment, it is apparent that specific values cannot be arbitrarily given to such conditions as the design, number and positioning of the resin bed in the reaction system, temperature and contact time for the treatment. Such conditions are not narrowly critical and obviously need only be at least sufficient to obtain the improvement desired. For instance, the subject invention contemplates the employment of any conventional anion exchange resin bed design through which the liquid medium to be treated may be passed, and any such bed may be easily removed and/or replaced as desired. Moreover, the number of beds employed, as well as their positioning in the reaction system involved is also not considered absolutely critical and need only be such that is suitable to obtain the result desired. Likewise, treatment conditions such as temperature, pressure and contact time may also vary greatly depending on the wishes of the operator and any suitable combination of such conditions may be employed herein so long as the desired effectiveness of the treatment is achieved. Likewise, the treatment is preferably carried out under normal operating pressures within the system employed although higher or lower pressures may be employed if desired, while the contact time of the liquid medium passing through the resin bed is normally only a matter of seconds.

Of course, it is to be understood that while the selection of the optimum levels and conditions of such variables as discussed above are dependent upon one's experience in the utilization of the subject resin treatment, only a certain measure of experimentation should be necessary in order to ascertain those conditions which are optimum for a given situation. For example, since the preferred subject invention is directed to a continuous hydroformylation process in which decomposition of the organophosphite ligand employed will be prevented and/or minimized for as long as possible, and since such decomposition is considered to be accelerated by the build-up of undesirable hydroxy alkyl phosphonic acid by-product, it is obviously preferred and beneficial to have the weakly basic anion exchange resin bed in place, at the start-up of the hydroformylation process involved, or in place soonly thereafter, so that the liquid medium to be treated can be continuously passed through the resin bed, thus preventing any undue build-up of undesirable acid by-product as discussed above. Of course, if desired, the resin bed can be used later on in the process to remove readily detectable amounts of such hydroxy alkyl phosphonic acid by-product build-up, although such is a less desirable way of minimizing decomposition of the organophosphite ligand.

Moreover, the diorganophosphite ligands employable herein have the added benefit of improved storage stability or shelf-life over that of conventional triorganophosphites, such as trialkylphosphites, e.g. trimethylphosphite, triethylphosphite, and the like, and triarylphosphites e.g. triphenylphosphite, tris(2-biphenyl)-phosphite and the like, particularly with regard to moisture sensitivity and hydrolytic stability.

Thus it should be clear that one of the featured beneficial factors involved in the employment of the diorgano phosphite ligands in this invention, in contrast to that heretofore employed in the prior art, is the wide processing latitude as taught herein that one has in selecting the proper combination of conditions that will be most useful in obtaining or at least best approaching a particular desired result or need.

Thus while it is clear that the rhodium hydroformylation process of this invention represents a clear technical advancement in the art, it should be noted that some rhodium loss, i.e. precipitation of the rhodium from solution, has been found to occur in the continuous liquid recycle hydroformylation process of this invention. It is believed that such rhodium loss has been caused by high temperatures employed in separating the desired aldehyde product from the rhodium catalyst containing product solution and that such rhodium loss may be reduced, if not eliminated, by separating the desired aldehyde product from the rhodium catalyst containing product solution under reduced pressure and at low temperatures such as below 130° C. and more preferably below 110° C.

In addition to providing the basic benefits of catalyst reactivity and stability in the hydroformylation of olefins to aldehydes as outlined hereinabove, the diorganophosphite ligands of Formulas (V) and (VI) above, as well as the rhodium complex catalysts containing such diorganophosphite ligands of Formulas (V) and (VI) above, are considered to be novel compositions of matter and uniquely beneficial in that they may allow for the use of higher aldehyde vaporization (separation) temperatures in the continuous liquid recycle hydroformylation process of this invention then heretofore considered preferred. For instance, as noted above, some rhodium loss has previously been experienced in some continuous liquid recycle hydroformylation process experiments and such loss has been attributed in part to the vaporization temperature employed in separating the desired aldehyde product from the rhodium catalyst containing product solution. Accordingly, heretofore it has been recommended that such separation of the desired aldehyde product be preferably conducted at below 110° C. to avoid such rhodium loss. It has now been surprisingly found that such separation of the desired aldehyde product may preferably be conducted at even higher temperatures, e.g. up to 120° C., and possibly even higher, when a diorganophosphite ligand of Formulas (V) or (VI) is employed as witnessed by an experiment wherein no rhodium loss was observed over a prolonged period of continuous hydroformylation and at such a higher preferred aldehyde vaporization (separation) temperature, when methyl[3,3′-di-t-butyl-5,5′-dimethoxy-1,1′-biphenyl-2,2′-diyl] phosphite was employed. Of course, the benefits attributable to a continuous process wherein the loss of rhodium is prevented or at least minimized over a long period of time and those attributable to being able to employing a higher temperature for separating the desired aldehyde product from the catalyst containing reaction solution without the attendent drawback of rhodium loss are self-evident. The higher the aldehyde separation temperature employed the more aldehyde product one may recover per given unit of time. In turn, the ability to be able to separate more aldehyde product more quickly, allows for greater processing control with regard to the build-up of higher boiling aldehyde condensation by-products that take place during the hydroformylation process, thus providing an effective means for eliminating and/or minimizing any adverse build-up of such higher boiling aldehyde condensation by-products.

In addition, the diorganophosphite ligands of Formulas (V) and (VI) above and the rhodium complex catalysts containing such ligands are believed to be more soluble in the hydroformylation reaction medium than the diorganophosphite compound counterparts of the same type wherein the $Z^2$ and $Z^3$ radicals of the above formulas are hydrocarbon radicals (e.g. t-butyl) instead of the ether (i.e. oxy) radicals, such as hydroxy aand/or —$OR^6$ as defined in said Formulas (V) and (VI) above. While not wishing to be held to any theory or mechanistic discourse, such ligand solubility may be the reason no rhodium loss was observed over a prolonged period of time at an aldehyde separation temperature higher than heretofore recommended as preferred when methyl[3,3′-di-t-butyl-5,5′-dimethoxy-1,1′-biphenyl-2,2′-diyl]phosphate was employed. Alternatively, rhodium complex catalysts containing a ligand as defined in said Formulas (V) and (VI) above may undergo some structural change under hydroformylation and/or vaporizer/separation conditions to a more stable or soluble rhodium complex due to the ether (i.e. oxy) radicals represented by $Z^2$ and $Z^3$ in Formulas (V) and (VI) above.

Moreover, while the diorganophosphite ligands of Formulas (V) and (VI) above and the rhodium complex catalysts containing such a diorganophosphite ligand are considered to be novel compositions of matter, it is of course to be understood that such ligands and catalysts can be readily made by the same general procedures, disclosed elsewhere herein, for obtaining diorganophosphite ligands and rhodium complex catalysts in general. Likewise diorganophosphites wherein $Z^2$ and $Z^3$ of Formulas (V) and (VI) are hydroxy radicals can be readily prepared by first obtaining the corresponding ligand wherein $Z^2$ and $Z^3$ are an alkoxy (e.g. benzyloxy) radical followed by any conventional dealkylation procedure (e.g. hydrogenolysis).

A further aspect of this invention can be described as a catalyst precursor composition consisting essentially of a solubilized Group VIII transition metal diorganophosphite complex precursor catalyst, an organic solvent and free diorganophosphite ligand. Such precursor compositions may be prepared by forming a solution of a Group VIII transition metal starting material, such as a metal oxide, hydride, carbonyl or salt e.g. a nitrate, which may or may not be in complex combination with a diorganophosphite ligand, an organic solvent and a free diorganophosphite ligand as defined herein. Any suitable Group VIII transition metal starting material may be employed e.g. rhodium dicarbonyl acetylacetonate, $Rh_2O_3$, $Rh_4(CO)_{12}$, $Rh_6(CO)_{16}$, $Rh(NO_3)_3$, diorganophosphite rhodium carbonyl hydrides, iridium carbonyl, diorganophosphite iridium carbonyl hydrides, osmium halide, chloroosmic acid, osmium carbonyls, palladium hydride, palladous halides, platinic acid, platinous halides, ruthenium carbonyls, as well as other salts of other Group VIII transition metals and carboxylates of $C_2$–$C_{16}$ acids such as cobalt chloride, cobalt nitrate, cobalt acetate, cobalt octoate, ferric acetate, ferric nitrate, nickel fluoride, nickel sulfate, palladium acetate, osmium octoate, iridium sulfate, ruthenium nitrate, and the like. Of course any suitable solvent may be employed such as e.g. those employable in the carbonylation process desired to be carried out. The desired carbonylation process may of course also dictate the various amounts of metal, solvent and ligand present in the precursor solution. Carbonyl and diorganophosphite ligands if not already complexed with the initial Group VIII transition metal may be complexed to the metal either prior to or in situ during the carbonylation process. By way of illustration, since the preferred Group VIII transition metal is rhodium and since the preferred carbonylation process is hydroformylation, the preferred catalyst precursor composition of this invention consists essentially of a solubilized rhodium carbonyl diorganophosphite acetylacetonate complex precursor catalyst, an organic solvent and free diorganophosphite ligand. Such precursor compositions are prepared by forming a solution of rhodium dicarbonyl acetylacetonate, an organic solvent and a diorganophosphite ligand as defined herein. The diorganophosphite readily replaces one of the dicarbonyl ligands of the rhodium-acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium carbonyl diorganophosphite acetylacetonate complex precursor are soluble can be employed. Accordingly, the amounts of rhodium complex catalyst precursor, organic solvent and diorganophosphite, as well as their preferred embodiments present in such catalyst precursor compositions may obviously correspond to those amounts employable in the hydroformylation process of this invention and which have already been discussed herein. Experience has shown that the acetylacetonate ligand of the precursor catalyst is replaced after the hydroformylation process has begun with a different ligand, e.g. hydrogen, carbon monoxide or diorganophosphite ligand, to form the active rhodium complex catalyst as explained above. The acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions thus provides a simple economical and efficient method for handling the rhodium precursor metal and hydroformylation start-up.

Finally, the aldehyde products of the hydroformylation process of this invention have a wide variety of utility that is well known and documented in the prior art e.g. they are especially useful as starting materials for the production of alcohols and acids.

Further as mentioned above, it is to be understood, that the particular choice of which diorganophosphite ligand may be best suited for use in given process will of course obviously depend on the end result most desired and such may often require balancing or compromise in overcoming or minimizing the the numerous factors that influence ligand stability and/or catalyst reactivity and stability.

For instance, when employed in the rhodium catalyzed hydroformylation processes of this invention, diorganophosphite ligands encompassed e.g. by Formulas (II) and (V) above, despite their above discussed benefits, can be susceptible in varying degrees to ligand decomposition or loss over prolonged continuous hydroformylation due to aqueous hydrolysis (i.e. hydrolysis of the ligand to its corresponding hydrogen phosphite, wherein W is replace with hydrogen) and/or due to transesterification (i.e. reaction of the ligand with a hydroxy containing compound, e.g. an alcohol wherein W is replaced by the hydroxy containing compound).

As noted above, when W of the ligands of Formulas (II) and (V) represent an aryl radical, the amount and type of substitution in the ortho positions (e.g. $X^1$, $X^2$, $Y^1$ and $Y^2$ groups of Formulas (III) and (V)) of all three aryl groups of the ligand may influence ligand stability and/or catalytic activity, particularly with regard to rhodium catalyzed hydroformylation carried out in the presence of excess free diorganophosphite ligand.

It is now considered that diorganophosphite ligands of Formulas (II) and (V) above, wherein $Z^2$, $Z^3$ Q, n and y are the same as defined above, and wherein both of the $Y^1$ and $Y^2$ groups are individually radicals having a steric hindrance of isopropyl or greater as defined above, and wherein W represents an aryl radical of formula

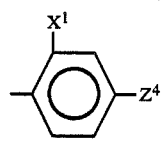

wherein $X^1$ represents a radical having a steric hindrance of isopropyl or greater, and wherein $Z^4$ is the same as defined above in Formula (V), have improved hydrolysis and transesterification properties as compared to similar ligands of Formulas (II) and (V) wherein e.g. W represents a simple alkyl radical such as methyl or a phenyl radical having no such bulky ortho substituent as said $X^1$ group.

As noted such improved hydrolysis and transesterification ligand stability may be attributed to the fact that the aryl radicals of such diorganophosphite ligands contain three bulky substituents (radicals having a steric hindrance of isopropyl or greater in ortho positions (i.e. $X^1$, $Y^1$ and $Y^2$) relative to the phosphorus atom. Moreover, diorganophosphite ligands having such steric hindrance caused by said three bulky ortho groups (i.e. $X^1$, $Y^1$ and $Y^2$) may further be employed to provide improved rhodium-phosphite complex catalyst activity by permitting smaller rhodium concentrations albeit at higher ligand concentrations to obtain essentially the same type of hydroformylation rates that are obtainable with comparable diorganophosphite containing e.g. only two such bulky ortho substituents in the ligand. A side consequence of employing lower rhodium concentrations at higher ligand concentrations is that the ligand to rhodium molar ratio is increased. Thus the ligand to rhodium molar ratio when employing such diorganophosphite containing three such bulky ortho substituents may be higher than when comparable diorganophosphite ligands containing e.g. only two such bulky ortho substituents in the ligand are employed. Accordingly the molar ratio of such diorganophosphite ligands containing three such bulky ortho substituents in the ligand per mole of Group VIII transition metal (e.g. rhodium) when employed in this invention may preferably range from about 4 to about 100 moles of ligand per mole of metal.

Indeed it has been observed that 2-t-butyl-4-methoxyphenyl-[3,3′-di-t-butyl-5,5′-dimethoxy-1,1′-biphenyl-2,2′diyl]phosphite in the rhodium catalyzed hydroformylation process of this invention is much more stable against hydrolysis and transesterification than e.g. its methyl-[3,3′-di-t-butyl-5,5′-dimethoxy-1,1′-biphenyl-2,2′-diyl]phosphite counterpart. Further it has been found that 2-t-butyl-4-methoxyphenyl[3,3′-di-t-butyl-5,5′-dimethoxy-1,1′-biphenyl-2,2′-diyl]phosphite can be employed to provide even better rhodium-phosphite complex catalytic activity than that obtainable with methyl[3,3′-di-t-butyl-5,5′-dimethoxy-1,1′-biphenyl-2,2′-diyl]phosphite in as much as essentially comparable hydroformylation rates (gram moles of aldehyde product per liter per hour) are obtainable with smaller rhodium concentrations, of said 2-t-butyl-4-methoxyphenyl-[3,3′-di-t-butyl-5,5′-dimethoxy-1,1′-biphenyl-2,2′-diyl]phosphite albeit at higher ligand concentrations than may be obtained with said methyl[3,3′-di-t-butyl-5,5′-dimethoxy-1,1′-biphenyl-2,2′-diyl]phosphite. ligands employable in this invention are those of the formula

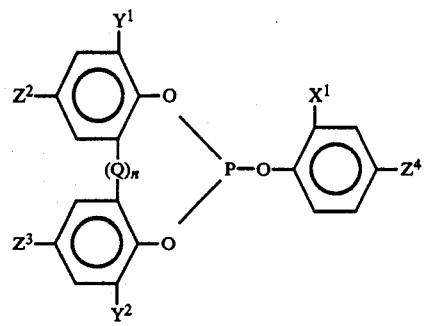

(VII)

wherein $Z^2$, $Z^3$, $Z^4$, Q and n are the same as defined above and wherein each $X^1$, $Y^1$ and $Y^2$ individually represent a radical having a steric hindrance of isopropyl or greater. More preferably, each $X^1$, $Y^1$ and $Y^2$ group individually represents t-butyl or t-amyl, and each $Z^2$ and $Z^3$ group individually represents a radical selected from the group consisting of hydroxy and an ether (i.e. oxy radical) such as —$OR^6$ as defined in Formulas (V) and (VI) above. Most preferably, $X^1$, $Y^1$ and $Y^2$ each represent a t-butyl radical while $Z^2$ and $Z^3$ each represent a methoxy radical, the most preferred ligand being 2-t-butyl-4-methoxyphenyl-[3,3'-di-t-butyl-5,5'-dimethoxy-1,1'-biphenyl-2,2'-diyl]phosphite.

It is of course to be understood that such ligands of Formula (VII) and the rhodium-phosphite complex catalysts thereof can be made by the same general procedures and employed in the processes of this invention in the same general manner as disclosed elsewhere herein for similar ligand and catalysts in general.

As further noted above some rhodium loss may be experienced in prolonged continuous hydroformylation with the diorganophosphite ligands of this invention and such also has been found to occur for example when 2-t-butyl-4-methoxyphenyl[3,3'-di-t-butyl-5,5'-dimethoxy-1,1'-biphenyl-2,2'-diyl]phosphite is employed as the ligand. However, unlike rhodium loss due to precipitation of a rhodium complex or a rhodium compound which might occur when a diorganophosphite such as methyl[3,3'-di-t-butyl-5,5'-dimethoxy-1,1'-biphenyl-2,2'-diyl]-phosphite is employed, rhodium can be lost as precipitated rhodium metal when a diorganophosphite such as 2-t-butyl-4-methoxyphenyl-[3,3'-di-t-butyl-5,5'-dimethoxy-1,1'-biphenyl-2,2'-diyl]phosphite is employed. While both types of rhodium precipitation problems may be addressed as discussed elsewhere herein (e.g. controlling vaporizer temperature) it has also now been found that rhodium metal precipitation may also be preferably addressed by either employing increased concentrations of the ligands of Formula (VII) and/or employing a small amount of a stabilizing agent such as vinylpyrrolidone-vinyl acetate copolymer.

The following examples are illustrative of the present invention and are not to be regarded as limitative. It is to be understood that all of the parts, percentages and proportions referred to herein and in the appended claims are by weight unless otherwise indicated.

EXAMPLE 1

A series of various rhodium complex catalyst precursor solutions consisting essentially of solubilized rhodium carbonyl diorganophosphite acetylacetonate complex precursor catalyst, organic solvent and free diorganophosphite ligand were prepared and employed to hydroformylate trans butene-2 into $C_5$ aldehydes in the following manner.

Rhodium dicarbonyl acetylacetonate was mixed with sufficient 1,1'-biphenyl-2,2'-diyl-(2,6-di-tertiary-butyl-4-methylphenyl)phosphite ligand having the formula

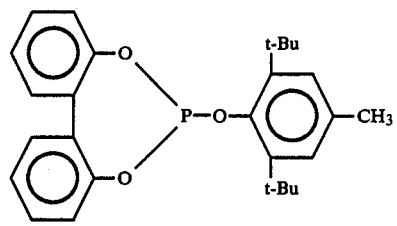

the amount of ligand being varied in each instance as shown in TABLE 1 below) and diluted with sufficient solvent Texanol® (2,2,4-trimethyl-1,3-pentanediol monoisobutyrate) to produce the various rhodium catalytic precursor solutions containing the amounts of rhodium and ligand shown in TABLE 1 below.

Each rhodium catalytic precursor solution so prepared was then employed to hydroformylate trans-butene-2 in a magnetically stirred, 100 ml capacity, stainless steel autoclave which was attached to a gas manifold for introducing gases to the desired partial pressures. The autoclave was also equipped with a pressure calibrator for determining reaction pressure to ±0.01 psia. and a platinum resistance thermometer for determining reactor solution temperatures to ±0.1° C. The reactor was heated externally by two 300 watt heating bands. The reactor solution temperature was controlled by a platinum resistance sensor connected to an external proportional temperature controller for controlling the temperature of the external band heaters.

In each hydroformylation reaction, about 20 milliliters of the rhodium catalytic precursor solution so prepared containing the rhodium complex, the diorganophosphite ligand and the solvent was charged to the autoclave reactor under nitrogen and heated to the reaction temperature employed (as given in TABLE 1 below). The reactor was then vented down to 5 psig. and 5 mL (2.9 grams) of trans-butene-2 introduced into the reactor. Then carbon monoxide and hydrogen (partial pressures given in Table 1) were introduced into the reactor via the gas manifold and the trans-butene-2 so hydroformylated.

The hydroformylation reaction rate in gram moles per liter per hour of $C_5$ aldehydes produced was determined from sequential 5 psia. pressure drops in the reactor spanning the nominal operating pressure in the reactor, while mole ratio of linear (n-valeraldehyde) to branched (2-methylbutyraldehyde) product was measured by gas chromatography and the results are given in Table 1 below, said results being determined after about a 5 to 20 percent conversion of the trans-butene-2 starting material.

product were determined in the same manner as in Example 1 and the results are given in TABLE 2 below.

TABLE 2

| Run No. | Temp. °C. | Rh, ppm | Ligand/Rhodium Mole Ratio | Partial Pressure | | butene-1 m moles | Reaction Rate Gram Moles/Liter/Hour | Linear/Branched C$_5$ Aldehyde Mole Ratio |
| --- | --- | --- | --- | --- | --- | --- | --- | --- |
| | | | | H$_2$ psia | CO psia | | | |
| 1 | 100 | 200 | 10 | 20 | 20 | 50 | 0.78 | 2.16 |
| 2 | 100 | 200 | 10 | 60 | 60 | 50 | 14.5 | 2.30 |
| 3 | 50 | 250 | 5 | 60 | 60 | 50 | 2.42 | 2.51 |
| 4 | 70 | 50 | 10 | 30 | 30 | 50 | 2.37 | 2.48 |
| 5 | 100 | 25 | 5 | 30 | 30 | 50 | 1.23 | 1.51 |
| 6 | 120 | 50 | 20 | 30 | 30 | 50 | 3.41 | 1.14 |

TABLE 1

| Run No. | Temp. °C. | Rh, ppm | Ligand/Rhodium Mole Ratio | Partial Pressure | | trans-butene-2 m moles | Reaction Rate Gram Moles/Liter/Hour | Linear/Branched C$_5$ Aldehyde Mole Ratio |
| --- | --- | --- | --- | --- | --- | --- | --- | --- |
| | | | | H$_2$ psia | CO psia | | | |
| 1 | 100 | 25 | 10 | 30 | 30 | 50 | 2.94 | 0.68 |
| 2 | 100 | 50 | 10 | 30 | 30 | 50 | 5.73 | 0.71 |
| 3 | 100 | 250 | 10 | 30 | 30 | 50 | 4.63 | 0.77 |
| 4 | 100 | 500 | 10 | 30 | 30 | 50 | 4.95 | 0.86 |
| 5 | 100 | 250 | 3 | 30 | 30 | 50 | 17.19 | 0.75 |
| 6 | 100 | 250 | 9 | 30 | 30 | 50 | 5.73 | 0.79 |
| 7 | 100 | 250 | 18 | 30 | 30 | 50 | 2.96 | 0.76 |
| 8 | 100 | 250 | 10 | 30 | 15 | 50 | 3.78 | 1.0 |
| 9 | 100 | 250 | 10 | 30 | 60 | 50 | 6.68 | 0.76 |
| 10 | 100 | 250 | 10 | 30 | 90 | 50 | 7.76 | 0.83 |
| 11 | 100 | 250 | 10 | 15 | 30 | 50 | 3.55 | 1.01 |
| 12 | 100 | 250 | 10 | 60 | 30 | 50 | 7.29 | 0.82 |
| 13 | 100 | 250 | 10 | 90 | 30 | 50 | 7.93 | 0.78 |
| 14 | 70 | 250 | 10 | 30 | 30 | 50 | 0.64 | 0.24 |
| 15 | 130 | 250 | 10 | 30 | 30 | 50 | 12.85 | 1.13 |

EXAMPLE 2

The same procedure and conditions employed in Example 1 of preparing a rhodium catalytic precursor solution using rhodium dicarbonyl acetylacetonate, Texanol ® and 1,1'-biphenyl-2,2'-diyl-(2,6-di-tert-butyl-4-methylphenyl)phosphite ligand and hydroformylating trans-butene-2 were repeated save for the exceptions of hydroformylating butene-1 instead of trans-butene-2 and using about 15 milliliters of the rhodium precursor solution instead of 20 milliliters and varying the rhodium complex catalyst precursor solutions and hydroformylation reaction conditions as shown in TABLE 2 below. The hydroformylation reaction rate in terms of gram moles per liter per hour of C$_5$ aldehydes produced as well as the mole ratio of linear (n-valeraldehyde) to branched (2-methylbutyraldehyde)

EXAMPLE 3

The same procedure and conditions employed in Example 1 of preparing a rhodium catalytic precursor solution using rhodium dicarbonyl acetylacetonate, Texanol ® and 1,1'-biphenyl-2,2'-diyl-(2,6-di-tert-butyl-4-methylphenyl)phosphite ligand and hydroformylating trans-butene-2 were repeated, save for the exceptions of using the various organophosphite ligands and varying the rhodium complex catalyst precursor solutions and hydroformylation reaction conditions as shown in TABLE 3 below. The hydroformylation reaction rate in terms of gram moles per liter per hour of C$_5$ aldehydes (pentanals) produced as well as the mole ratio of linear (n-valeraldehyde) to branched (2-methylbutyraldehyde) product were determined in the same manner as in Example 1 and the results are given in TABLE 3 below.

TABLE 3

| Run No. | Ligand (g) | Precursor Solution and Reaction Conditions | Reaction Rate Gram Moles/Liter/Hour | Linear/Branched Aldehyde Mole Ratio |
| --- | --- | --- | --- | --- |
| 1 | 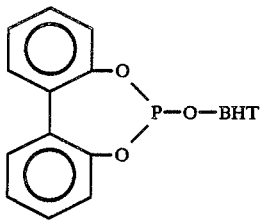 | (b) | 4.7 | 0.7 |

TABLE 3-continued

| Run No. | Ligand (g) | Precursor Solution and Reaction Conditions | Reaction Rate Gram Moles/ Liter/Hour | Linear/ Branched Aldehyde Mole Ratio |
|---|---|---|---|---|
| 2 | (PhO)₂P—O—BHT | (b) | 3.4 (h) | 0.89 |
| 3 | dibenzofuran-like diphenoxy-CH₂ bridged P—O—BHT | (b) | 17.82 (i) | 0.86 |
| 4 | 3,3',5,5'-tetra-t-Bu-biphenyl-2,2'-diyl P—O—BHT | (b) | 0.46 | 0.56 |
| 5 | biphenyl-2,2'-diyl P—O—Ph | (c) | 1.1 (j) | 1.0 |
| 6 | biphenyl-2,2'-diyl P—O—(o-t-Bu-phenyl) | (c) | 2.9 (j) | 1.0 |
| 7 | biphenyl-2,2'-diyl P—O—(2,6-di-Ph-phenyl) | (c) | 2.6 (j) | 1.0 |

TABLE 3-continued
| Run No. | Ligand (g) | Precursor Solution and Reaction Conditions | Reaction Rate Gram Moles/ Liter/Hour | Linear/ Branched Aldehyde Mole Ratio |
|---|---|---|---|---|
| 8 | 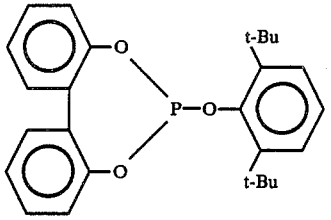 | (c) | 8.1 | 0.83 |
| 9 | 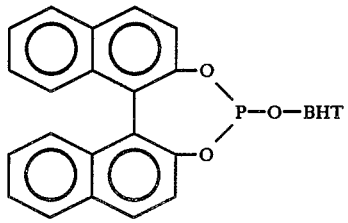 | (a) | 4.5 | 1.12 |
| 10 | 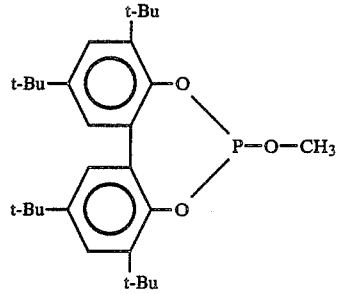 | (e,f) | 5.4 | 0.68 |
| 11 | 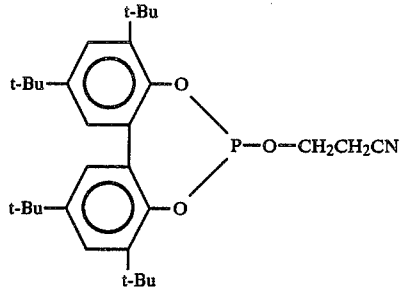 | (e,f) | 0.65 | 0.68 |
| 12 | 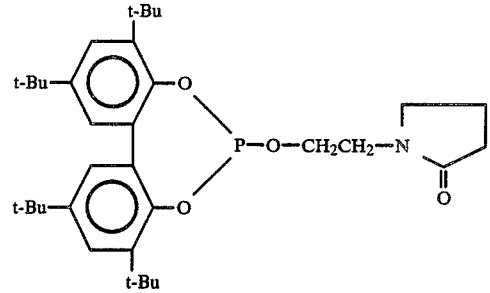 | (e) | 0.51 | 0.62 |

TABLE 3-continued
| Run No. | Ligand (g) | Precursor Solution and Reaction Conditions | Reaction Rate Gram Moles/ Liter/Hour | Linear/ Branched Aldehyde Mole Ratio |
|---|---|---|---|---|
| 13 | | (e,f) | 0.92 | 0.67 |
| 14 | | (d) | 8.7 | 0.82 |
| 15 | | (d) | 4.0 | 0.88 |
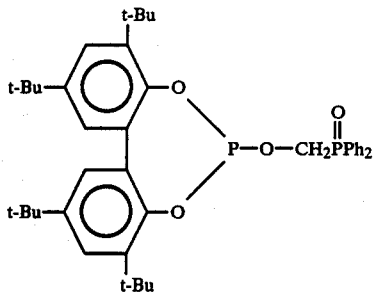

TABLE 3-continued

| Run No. | Ligand (g) | Precursor Solution and Reaction Conditions | Reaction Rate Gram Moles/ Liter/Hour | Linear/ Branched Aldehyde Mole Ratio |
| --- | --- | --- | --- | --- |
| 16 | t-Bu substituted bis(biphenyl) phosphite with cyanophenoxy group (structure shown) | (d) | 7.6 | 1.1 |

(a) Precursor solution and reaction conditions: 200 ppm rhodium; 6 moles diorganophosphite ligand per mole of rhodium; reaction temperature 100° C.; partial pressures; $H_2$ = 20 psia., CO = 20 psia, trans-butene-2 = 50 m moles.

(b) Precursor solution and reaction conditions: 200 ppm rhodium; 10 moles diorganophosphite ligand per mole of rhodium; reaction temperature 105° C.; partial pressures, $H_2$ = 30 psia, CO = 30 psia, trans-butene-2 = 50 m moles.

(c) Precursor solution and reaction conditions: 230 ppm rhodium; 3 moles diorganophosphite ligand per mole of rhodium; reaction temperature 100° C.; partial pressures; $H_2$ = 20 psia, CO = 20 psia, trans-butene-2 = 50 m moles. Used 15 milliliter rhodium catalytic precursor solution instead of 20 milliliters.

(d) Precursor solution and reaction conditions: 200 ppm rhodium; 10 moles diorganophosphite ligand per mole of rhodium; reaction temperature 105° C.; partial pressures; $H_2$ = 30 psia, CO = 30 psia, trans-butene-2 = 50 m moles. Used 15 milliliters rhodium catalytic precursor solution instead of 20 milliliters.

(e) Precursor solution and reaction conditions: 200 ppm rhodium; 6 moles diorganophosphite ligand per mole of rhodium; reaction temperature 100° C.; partial pressures; $H_2$ = 20 psia., CO = 20 psia, trans-butene-2 = 50 m moles. Used 15 milliliters rhodium catalytic precursor solution instead of 20 milliliters.

(f) Used $Rh_4(CO)_{12}$ as rhodium precursor instead of rhodium dicarbonyl acetylacetonate.

(g) BHT = 2,6-di-tert-butyl-4-methylphenyl t-Bu = tertiary-butyl radical

Ph = phenyl(h) Activity of this comparative triorganophosphite promoted catalyst rapidly declined under continuous hydroformylation (See Example 5).

(i) Activity of this diorganophosphite promoted catalyst declined very rapidly in a continuous glass reactor experiment similar to that described in Example 5

(j) The activity of these diorganophosphite promoted catalysts was sharply inhibited when the hydroformulation was carried out using more than 3 mole equivalents of ligand per mole of rhodium.

EXAMPLE 4

The same procedure and conditions employed in Example 1 of preparing a rhodium catalytic precursor solution using rhodium dicarbonyl acetylacetonate, Texanol ® and 1,1'-biphenyl-2,2'-diyl-(2,6-di-tert-butyl-4-methylphenyl)phosphite ligand and hydroformylating trans-butene-2 were repeated, save for the exceptions of employing various different olefins as the starting hydroformylation material and varying the rhodium complex catalyst precursor solutions and hydroformylation reaction conditions as shown in TABLE 4 below. The hydroformylation reaction rate in terms of gram moles per liter per hour of aldehyde produced as well as the mole ratio of linear aldehyde to branched aldehyde product were determined as in Example 1 and the results are given in TABLE 4 below.

TABLE 4

| Olefin | [Rh] ppm | Ligand/Rh mole ratio | Partial Pressure CO psia | Partial Pressure $H_2$ psia | Olefin m moles or (psia) | Temp. °C. | Reaction Rate Gram Moles/ Liter/Hour | Linear/ Branched Aldehyde Mole Ratio |
| --- | --- | --- | --- | --- | --- | --- | --- | --- |
| Butene-1 | 200 | 10 | 60 | 60 | 50 | 100 | 14.5 | 2.3 |
| Butene-2 (trans) | 250 | 10 | 30 | 30 | 50 | 100 | 4.63 | 0.77 |
| isobutene | 150 | 10 | 15 | 45 | 50 | 115 | 1.65 | a |
| Cyclohexene | 150 | 10 | 60 | 60 | 63 | 100 | 4.8 | b |
| Dicyclopentadiene | 150 | 10 | 60 | 60 | 9.2 | 100 | 2.1 | c |
| Vinyl Acetate | 200 | 10 | 60 | 60 | 54 | 80 | 0.37 | d |
| Allyl Alcohol | 100 | 10 | 60 | 60 | 73.5 | 70 | 2.97 | e |
| Allyl-tert-butyl ether | 100 | 10 | 60 | 60 | 30 | 70 | 1.90 | 1.3 |
| 1,5-Hexadiene | 100 | 10 | 60 | 60 | 43 | 70 | 2.11 | 2.5 f |
| Ethylene | 100 | 10 | 20 | 20 | (25) | 60 | 1.48 | g |
| Ethylene | 500 | 3 | 25 | 25 | (25) | 30 | 0.27 | g |
| Propylene | 500 | 3 | 25 | 25 | (25) | 30 | 0.14 | 1.77 |
| Cyclohexene | 200 | 25 | 40 | 40 | 50 | 160 | 3.5 | b |
| Decene-1 | 200 | 10 | 47.5 | 47.5 | 22 | 100 | 5.7 | 1.1 h |
| Styrene | 200 | 10 | 47.5 | 47.5 | 30 | 100 | 10.0 | 1.9 i |

TABLE 4-continued

| Olefin | [Rh] ppm | Ligand/Rh mole ratio | Partial Pressure | | Olefin m moles or (psia) | Temp. °C. | Reaction Rate Gram Moles/ Liter/Hour | Linear/ Branched Aldehyde Mole Ratio |
|---|---|---|---|---|---|---|---|---|
| | | | CO psia | $H_2$ psia | | | | |
| Methyl methacrylate | 200 | 10 | 47.5 | 47.5 | 47 | 100 | 2.5 | j | a = One product (3-methylbutyraldehyde) is formed.
b = One product (cyclohexane carboxaldehyde) is formed.
c = Several isomeric aldehydes are formed.
d = Only the branched isomer. α-acetoxypropionaldehyde, is detected.
e = Only the linear isomer, 4-hydroxy-butyraldehyde is detected.
f = The ratio refers to that of the Hept-6-ene-1-al and 2-methyl-hex-5-ene-1-al.
g = One product (propionaldehyde) is formed.
h = The ratio refers to that of n-undecanal and 2-methyldecanal.
i = The ratio refers to that of 3-phenylpropionaldehyde and 2 phenylpropionaldehyde.
j = One product [methyl (2-methyl-3 formyl) propionate] is formed.

EXAMPLE 5

The long term catalyst stability of 1,1'-biphenyl-2,2'-diyl-(2,6-di-tert-butyl-4-methylphenyl)phosphite (the diorganophosphite ligand of Example 1) promoted rhodium catalyst as compared to diphenyl(2,6-di-tert-butyl-4-methylphenyl)phosphite (the triorganophosphite ligand of Run No. 2 in Table 3 above) promoted rhodium catalyst was determined in the following manner.

These long term catalyst stability experiments were conducted by hydroformylating trans-butene-2 in a glass reactor in a continuous single pass mode. The reactor consisted of a three ounce pressure bottle submersed in an oil bath with a glass front for viewing. In each experiment about 20 mL of a freshly prepared rhodium catalytic precursor solution was charged to the reactor with a syringe after purging the system with nitrogen. Each precursor solution contained about 200 ppm rhodium introduced as rhodium dicarbonyl acetylacetonate, about 5 mole equivalents of phosphorous ligand per mole of rhodium metal and n-valeraldehyde trimer as the solvent. After closing the reactor, the system was again purged with nitrogen and the oil bath was heated to furnish the desired hydroformylation reaction temperature. The hydroformylation reaction in each experiment was conducted at a total gas pressure of about 165 psig. using about 30 psia. hydrogen, about 24 psia. trans-butene-2 and about 30 psia. carbon monoxide, the remainder being nitrogen. The flows of the feed gases (carbon monoxide, hydrogen and propylene) were controlled individually with mass flow meters and the feed gases dispersed into the precursor solution via stainless steel spargers. The unreacted portion of the feed gases stripped out the product $C_5$ aldehydes and the outlet gas was analyzed for $C_5$ aldehyde products periodically over four days of continuous operation at the reaction temperatures given in TABLE 5 below. The average reaction rates for each experiment in terms of gram moles per liter per hour of product $C_5$ aldehydes as well as the n-valeraldehyde to 2-methylbutyraldehyde product ratio for each day of operation are given in TABLE 5 below.

TABLE 5

TEST RESULTS - DAILY AVERAGES

| Ligand Used | Days Opern. | Temp. °C. | Rhodium ppm* | Ligand wt. % | Partial Pressures | | | Reaction Rate Gram Moles/ Liter/Hour | Linear/ Branched Aldehyde Mole Ratio | Mole % Butene-1** |
|---|---|---|---|---|---|---|---|---|---|---|
| | | | | | CO psia | $H_2$ psia | Trans butene-2 psia | | | |
| A | 1.0 | 105 | 170 | 0.4 | 31 | 30 | 18 | 0.83 | 1.05 | 5.90 |
| \| | 1.9 | 105 | 167 | 0.3 | 30 | 29 | 23 | 1.09 | 1.08 | 6.04 |
| \| | 2.9 | 105 | 171 | 0.4 | 30 | 29 | 22 | 1.05 | 1.09 | 5.92 |
| \| | 3.5 | 105 | 174 | 0.4 | 30 | 31 | 23 | 1.03 | 1.12 | 5.86 |
| A | 4.4 | 105 | 170 | 0.4 | 29 | 31 | 24 | 1.06 | 1.11 | 5.84 |
| B | 1.0 | 105 | 177 | 0.4 | 30 | 35 | 26 | 0.36 | 0.74 | 5.57 |
| \| | 1.9 | 105 | 184 | 0.4 | 30 | 28 | 33 | 0.26 | 0.69 | 4.98 |
| \| | 2.9 | 105 | 189 | 0.4 | 30 | 29 | 34 | 0.17 | 0.51 | 4.10 |
| \| | 3.5 | 105 | 192 | 0.4 | 29 | 31 | 34 | 0.12 | 0.47 | 3.16 |
| B | 4.4 | 105 | 186 | 0.4 | 30 | 31 | 33 | 0.09 | 0.68 | 2.56 |

A = 1,1'-biphenyyl-2,2'-diyl-(2,6-di-tert-butyl-4-methylphenyl) phosphite
B = diphenyl(2,6-di-tert-butyl-4-methylphenyl) phosphite
*Changing values reflect change in daily average liquid reactor solution levels.
**Percent of Isomerized Butene - 1 of the total amount of Butenes in the reactor outlet gas.

The above data show that the diorganophosphite ligand [1,1'-biphenyl-2,2'-diyl-(2,6-di-tert-butyl-4-methylphenyl)phosphite] of this invention maintained catalytic activity after over four days of continuous hydroformylation whereas the comparative triorganophosphite ligand [diphenyl(2,6-di-tert-butyl-4-methylphenyl)phosphite] promoted catalyst, which is not of this invention, lost about 75% of its catalytic activity over the same period of time. Analysis of the outlet gas composition indicated that total (equilibrium) isomerization of the pure butene-2 feed was achieved when the diorganophosphite (Ligand A) was employed. The outlet butene-1 concentration (of the total butenes in the outlet) approximates the calculated thermodynamic equilibrium value of 5.77 mole percent of butene-1 at 105° C. and a total pressure of 175 psia. The triorganoposphite (Ligand B) showed an ability to isomerize butene-2, but this rapidly diminished over the period of the test.

EXAMPLE 6

A series of various rhodium complex catalyst precursor solutions consisting essentially of solubilized rhodium carbonyl diorganophosphite acetylacetonate complex precursor catalyst, organic solvent and free diorganophosphite ligand were prepared and employed to hydroformylate isobutylene into aldehyde in the following manner.

Rhodium dicarbonyl acetylacetonate was mixed with a sufficient amount of diorganophosphite ligand and diluted with sufficient solvent. Texanol ®, to produce a rhodium catalytic precursor solution containing about 150 ppm of rhodium calculated as free metal and about 10 mole equivalents of diorganophosphite ligand per mole of rhodium. The ligand being varied as given in TABLE 6 below.

In each hydroformylation reaction, about 20 milliliters of the rhodium catalytic precursor solution so prepared was charged to the autoclave reactor described in Example 1 under nitrogen and heated to the reaction temperature employed as given in TABLE 6 below). The reactor was then pressurized to 10 psig. with nitrogen and 5 mL (about 3.12 grams of isobutylene) introduced into the reactor. Then about 30 psia hydrogen and about 30 psia. of a 1:1 syn gas mixture (15 psia. of carbon monoxide and 15 psia of hydrogen) were introduced into the reactor via the gas manifold and the isobutylene so hydroformylated.

The hydroformylation reaction rate in gram moles per liter per hour of aldehyde produced (3-methylbutyraldehyde being the only aldehyde product) was determined from sequential 5 psia. pressure drops in the reactor, spanning the nominal operating pressure in the reactor and the results are given in TABLE 6 below, said results being determined up to about a 30 percent conversion of the isobutylene starting material.

TABLE 6

| Run No. | Ligand | Temp. °C. | Reaction Rate gram moles/Liter/Hr. |
|---|---|---|---|
| 1 | 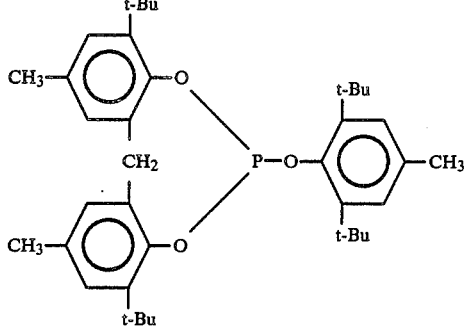 | 115 | 0.07 |
| 2 | 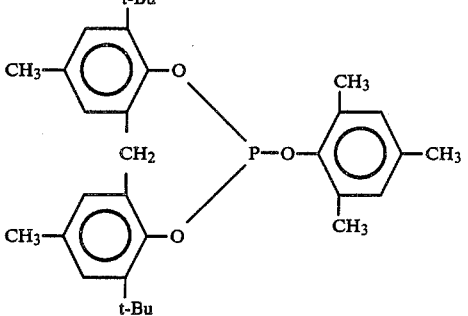 | 115 | 0.42 |
| 3 | 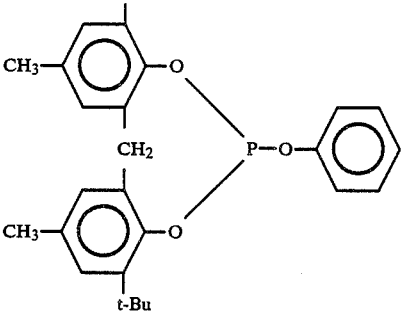 | 115 | 1.80 |
| 4 | ″ | 100 | 1.50 |
| 5 | ″ | 85 | 1.15 |

TABLE 6-continued
| Run No. | Ligand | Temp. °C. | Reaction Rate gram moles/Liter/Hr. |
|---|---|---|---|
| 6 | 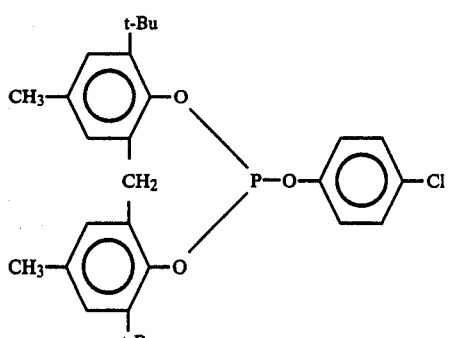 | 100 | 1.38 |
| 7 | 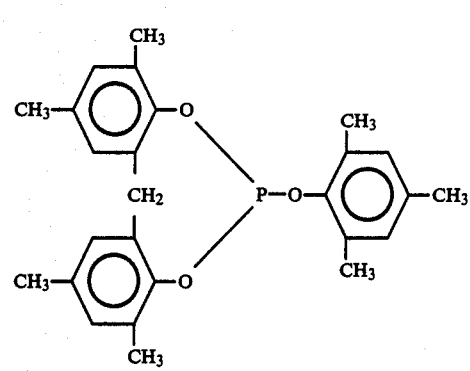 | 100 | 2.15 |
| 8 | 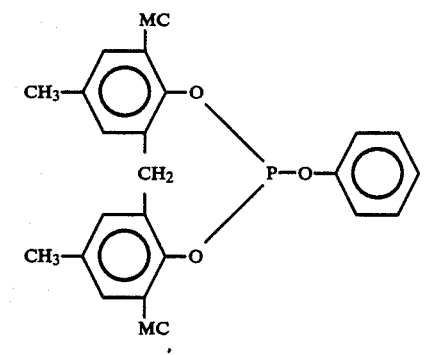 | 100 | 1.49 |
| 9 | 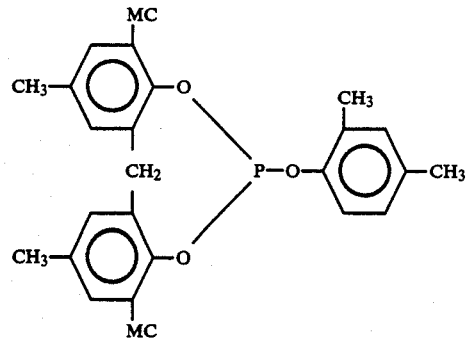 | 100 | 1.92 |

TABLE 6-continued
| Run No. | Ligand | Temp. °C. | Reaction Rate gram moles/Liter/Hr. |
|---|---|---|---|
| 10 | 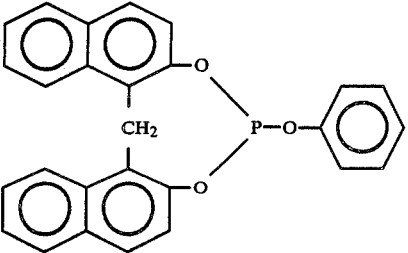 | 100 | 0.05 |
| 11 | 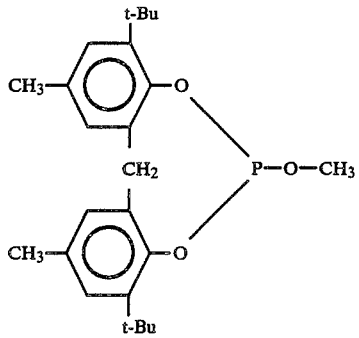 | 100 | 1.56 |
| 12 | 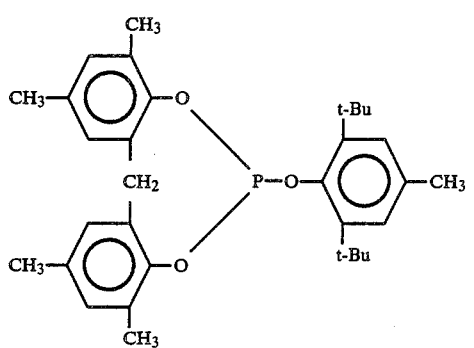 | 100 | 0.34 |
| 13 | 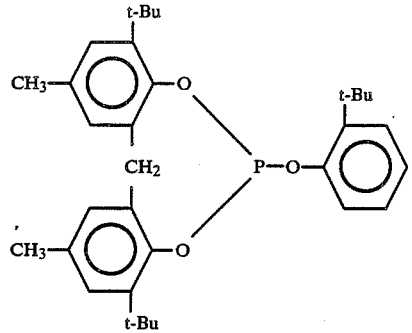 | 100 | 0.86 |
| 14 | 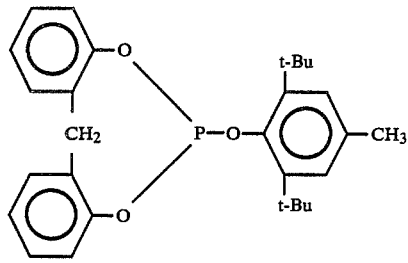 | 100 | 3.25 |

TABLE 6-continued
| Run No. | Ligand | Temp. °C. | Reaction Rate gram moles/Liter/Hr. |
|---|---|---|---|
| 15 | 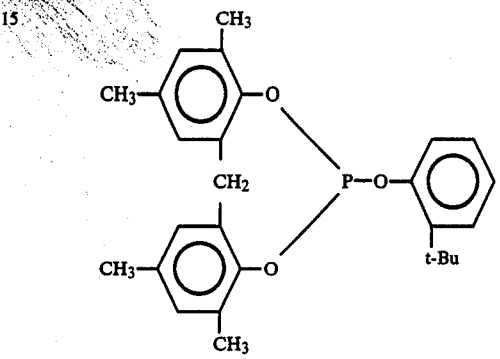 | 100 | 0.40 |
| 16 | 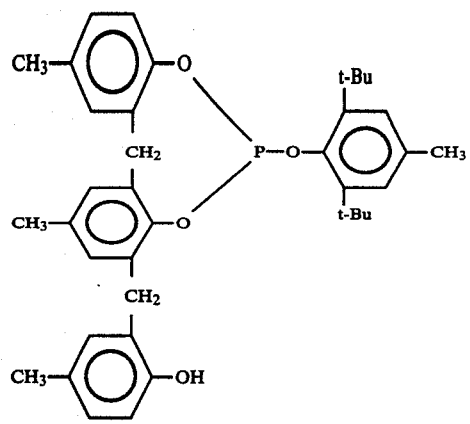 | 100 | 0.22 |
| 17 | 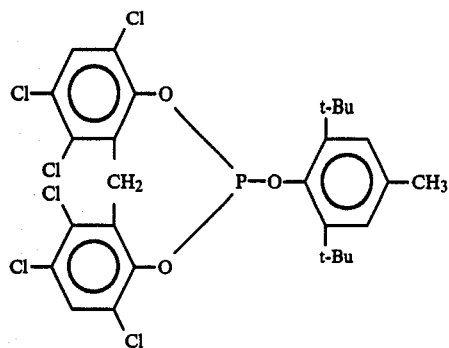 | 100 | 0.05 |
| 18 | 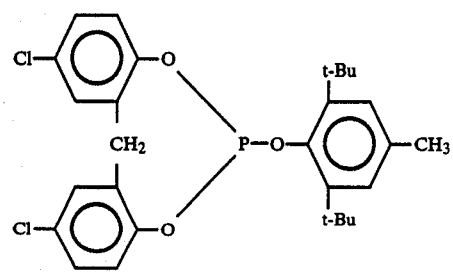 | 100 | 1.29 |

TABLE 6-continued

| Run No. | Ligand | Temp. °C. | Reaction Rate gram moles/Liter/Hr. |
|---|---|---|---|
| 19 | [structure: bis(3-methyl-6-t-butylphenyl) neopentyl phosphite-type ligand with P—O—CH$_2$—C(CH$_3$)$_3$] | 100 | 1.25 |
| 20 | " | 115 | 0.87 |
| 21 | [structure: bis(3,5-di-t-butylphenyl) phenyl phosphite-type ligand with P—O—phenyl] | 100 | 2.99 |
| 22 | [structure: bis(3,5-di-t-butylphenyl) 4-methoxyphenyl phosphite-type ligand with P—O—C$_6$H$_4$—OCH$_3$] | 100 | 3.30 | t-Bu = Tertiary-butyl radical
MC = 1-Methylcyclohexyl radical

EXAMPLE 7

A series of various rhodium complex catalyst precursor solutions consisting essentially of solubilized rhodium carbonyl diorganophosphite acetylacetonate complex precursor catalyst, organic solvent and free diorganophosphite ligand were prepared and employed to hydroformylate trans-butene-2 into C$_5$ aldehydes in the following manner.

Rhodium dicarbonyl acetylacetonate was mixed with a sufficient amount of a diorganophosphite ligand and diluted with sufficient solvent, Texanol ®, to produce a rhodium catalytic precursor solution containing about 250 ppm of rhodium calculated as free metal and about 10 mole equivalents of diorganophosphite ligand per mole of rhodium. The ligand being varied as given in TABLE 7 below.

In each hydroformylation reaction, about 15 milliliters of the rhodium catalytic precursor solution so prepared was charged to the autoclave reactor under nitrogen and heated to the hydroformylation reaction temperature of 100° C. The reactor was then vented down to 5 psig. and 5 cc (2.9 grams) of the olefin employed (as given in TABLE 7 below) introduced into the reactor. Then about 90 psia. of a 1:1 syn gas mixture (45 psia. of carbon monoxide and 45 psia of hydrogen) were introduced into the reactor via the gas manifold and the olefin so hydroformylated.

The hydroformylation reaction rate in gram moles per liter per hour of C$_5$ aldehydes produced was determined from sequential 5 psia. pressure drops in the reactor spanning the nominal operating pressure in the reactor, while mole ratio of linear (n-valeraldehyde) to branched (2-methylbutyraldehyde) product was measured by gas chromatography and the results are given in TABLE 7 below, said results being determined after about a 5 to 20 percent conversion of the trans-butene-2 starting material.
TABLE 7
| Run No. | Ligand | Reaction Rate Gram/Moles/ Liter/Hour | Linear/Branched Aldehyde Mole Ratio |
|---|---|---|---|
| 1 | 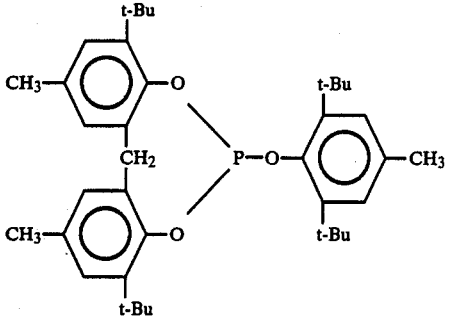 | 0.0 | — |
| 2 | 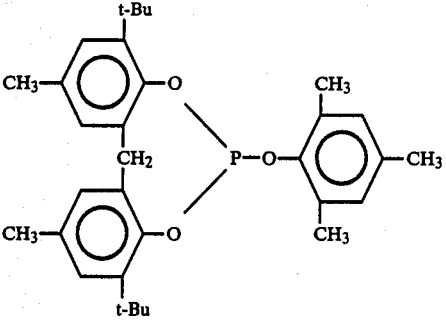 | 2.8 | 0.72 |
| 3 | 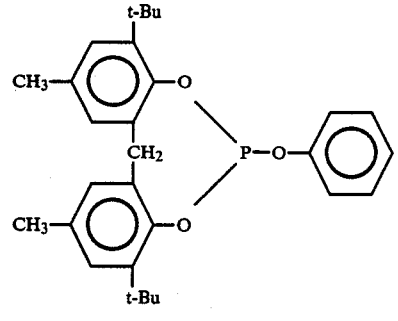 | 7.0 | 0.62 |
| 4 | 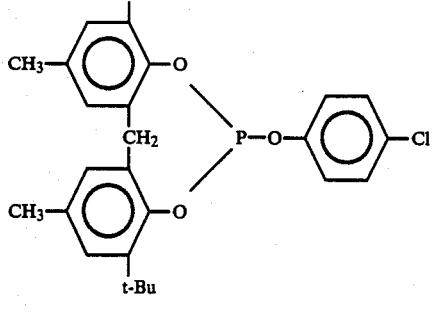 | 8.1 | 0.67 |

TABLE 7-continued
| Run No. | Ligand | Reaction Rate Gram/Moles/Liter/Hour | Linear/Branched Aldehyde Mole Ratio |
|---|---|---|---|
| 5 | 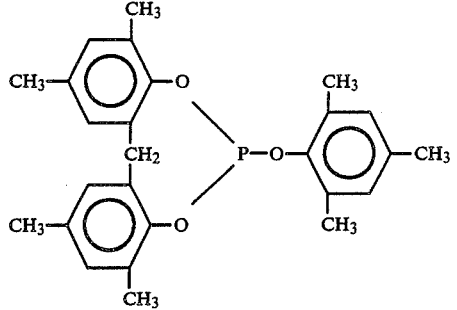 | 12.0 | 0.78 |
| 6 | 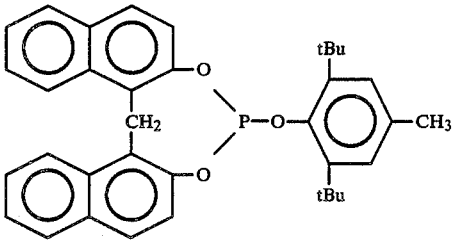 | 12.0 | 0.93 |
| 7 | 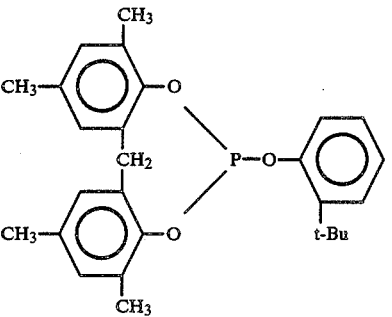 | 1.9 | 1.2 |
| 8 | 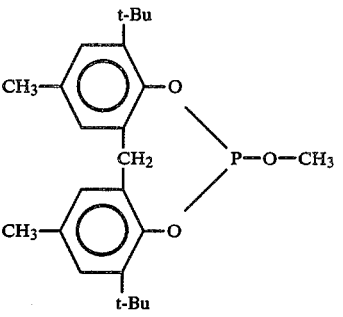 | 5.5 | 0.67 |
| 9 | 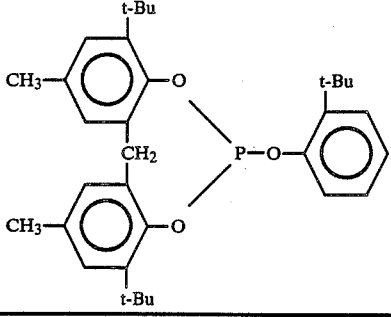 | 8.1 | 0.69 |
t-Bu = tertiary-butyl radical

EXAMPLE 8

The reactivity of various diorganophosphite and triorganophosphite ligands towards aldehyde were determined as follows.

A series of phosphite-aldehyde solutions were prepared, each in the same manner, by successively charging, to an oven dried (150° C. for one hour) 2.0-oz. narrow-neck bottle which had cooled to ambient temperature in a dry box and which contained a magnetic stirring bar, about 4.5 m moles of phosphite ligand, about 3.0 m moles of triphenyl phosphine oxide, as a phosphorus containing internal standard, and a sufficient amount of a mixture of n-valeraldehyde and 2-methylbutyraldehyde to obtain a combined weight of 30 grams for each solution. The bottle was then sealed with a serum stopper, removed from the dry box and placed on a magnetic stirrer at ambient temperature until a solution was obtained. The bottle was then returned to the dry box to remain under nitrogen atmosphere at ambient temperature. Periodically 3 milliliter samples of each solution were drawn and the phosphite concentration analyzed by phosphorus-31 NMR spectroscopy. The extent of phosphite decomposition (as a result of reacting with aldehyde) was qualitatively determined from the relative intensities of the $^{31}P$ NMR resonances corresponding to those of the pure phosphite ligand employed and the internal standard. The phosphite ligands employed and the test results are given in TABLE 8 below.

TABLE 8

| Run No. | Ligand Structure | Extent of Phosphite Decomposition | | | |
|---|---|---|---|---|---|
| | | Day 1 | Day 4 | Day 7 | Day 10 |
| 1. | (PhO)$_3$P | Some | All | — | — |
| 2. | [(C$_2$H$_5$)(C$_4$H$_9$)CH—CH$_2$O]$_3$P | Some | Most | — | — |
| 3. | [(2-Ph-C$_6$H$_4$)O]$_3$P | None | Some | Most | All |
| 4. | biphenyl-2,2'-diyl phosphite, 2-phenylphenyl ester | All | — | — | — |
| 5. | biphenyl-2,2'-diyl phosphite, 2,4,6-trimethylphenyl ester | Some | Most | — | — |

TABLE 8-continued

| Run No. | Ligand Structure | Extent of Phosphite Decomposition | | | |
|---|---|---|---|---|---|
| | | Day 1 | Day 4 | Day 7 | Day 10 |
| 6. | (biphenyl cyclic phosphite with 2,6-di-t-Bu-4-methylphenoxy group) | None | None | None | None | t-Bu = tertiary butyl radical
Ph = Phenyl radical

EXAMPLE 9

The reactivity of various phosphite ligands towards aldehyde at high temperatures were determined as follows.

A series of phosphite-aldehyde solutions were prepared, each in the same manner by successively charging a 12-oz. Fischer-Porter bottle containing a magnetic stirring bar, with about 0.005 moles of phosphite ligand, about 0.0075 moles of barium carbonate, about 0.0025 moles of barium valerate (the barium salts being employed to maintain neutrality of the solution) and a sufficient amount of a mixture of n-valeraldehyde and 2-methylbutyraldehyde to obtain a combined weight of 100 grams for each solution. The bottle was sealed with a pressure cap modified to contain a mechanical stirrer and gas purging and sampling valves and inserted into a stainless steel wire mesh protective covering. The bottle containing the phosphite-aldehyde solution was then purged with nitrogen and about 50 psig nitrogen allowed to remain. Each solution was then stirred for one hour at ambient temperature. Each phosphite-ligand solution was then heated by placing the bottle into a preheated (160° C.) silicone oil bath. Periodically samples of each solution were withdrawn and the phosphite concentration determined quantitatively by high pressure liquid chromatography. The phosphite ligands employed and extent of phosphite decomposition (as a result of reacting with the aldehyde) are give in TABLE 9 below.

TABLE 9

| Run No. | Ligand | Temp °C. | Reaction Time (hrs) | Percent Ligand Decomposed |
|---|---|---|---|---|
| 1 | (2-phenylphenoxy)$_3$P | 160 | 23.5 | 44 |
| 2 | biphenyl cyclic phosphite with 2,6-di-t-Bu-4-methylphenoxy | 160 | 21 | 13 |
| 3 | binaphthyl cyclic phosphite with 2,6-di-t-Bu-4-methylphenoxy | 160 | 25 | 0 |

TABLE 9-continued

| Run No. | Ligand | Temp °C. | Reaction Time (hrs) | Percent Ligand Decomposed |
|---|---|---|---|---|
| 4 | (structure: bis(3,5-di-t-butylphenyl) biphenyl phosphite with P—O—Ph) | 160 | 21 | 4 |
| 5 | (structure: methyl/t-Bu substituted methylene-bridged bisphenol phosphite with P—O—Ph) | 160 | 21 | 4 |
| 6 | (structure: methylene-bridged binaphthyl phosphite with P—O-(2,6-di-t-Bu-4-methylphenyl)) | 160 | 25 | 0.5 | t-Bu = tertiary butyl radical
Ph = Phenyl radical

EXAMPLE 10

In a continuous catalyst liquid recycle manner, a mixed olefin starting material of butene-1 and butene-2 (cis and trans) was hydroformylated for six days followed by the continuous catalyst liquid recycle hydroformylation of butene-1 as follows.

The liquid recycle reactor system employed contained two 2.8 liter stainless steel stirred tank reactors, connected in series, each containing a vertically mounted agitator and a circular tubular sparger near the bottom of the reactor for feeding the olefin and/or syn gas. The sparger contained a plurality of holes of sufficient size to provide the desired gas flow into the liquid body. Reactor 1 contained a silicone oil shell as means of bringing the contents of the reactors up to reaction temperature while the reaction solution in Reactor 2 was heated by an electrical heater. Both reactors contained internal cooling coils for controlling the reaction temperature. Reactors 1 and 2 were connected via a line to transfer any unreacted gases from reactor 1 to reactor 2 and were further connected via a line so that a portion of the liquid reaction solution containing aldehyde product and catalyst from reactor 1 could be pumped into reactor 2 wherein the unreacted olefin of reactor 1 is further hydroformylated in reactor 2.

Each reactor also contained a pneumatic liquid level controller for automatic control of the liquid levels in the reactors. Reactor 1 further contained a line for introducing the olefin and syn gas through the sparger, while make up syn gas was added to reactor 2 via the same transfer line carrying the unreacted gases from reactor 1. Reactor 2 also contained a blow-off vent for removal of the unreacted gases. A line from the bottom of reactor 2 was connected to the top of a vaporizer so that a portion of the liquid reaction solution could be pumped from reactor 2 to the vaporizer. Vaporized aldehyde was disengaged from the non-volatilized components of the liquid reaction solution in the gas-liquid separator part of the vaporizer. The remaining non-volatilized catalyst containing liquid reaction solution was pumped through a recycle line back into reactor 1. The recycle line also contained a pneumatic liquid level controller. The vaporized aldehyde product was passed into a water-cooled condenser, liquified and collected in a product receiver.

The hydroformylation reaction was conducted by charging about 0.789 liters of a catalyst precursor solution of rhodium dicarbonyl acetylacetonate (about 200 ppm rhodium), about 1.0 wt. % 1,1'-biphenyl-2,2'-diyl-(2,6-di-tert-butyl-4-methylphenyl)phosphite ligand (about 10 mole equivalents of ligand per mole of rhodium), about 0.5 wt. % 2,6-di-tert-butyl-4-methylphenol as an antioxidant, and about 98.5 wt. % of $C_5$ aldehyde (about 68.5 wt % valeraldehyde and about 30 wt % valeraldehyde trimer) as solvent to reactor 1. About 0.96 liters of the same catalyst precursor solution was charged to reactor 2. The reactor system was then purged with nitrogen to remove any oxygen present. Then about 100 psig. nitrogen pressure was put on both reactors and the reactors heated to their reaction temperatures given in TABLE 10 below. Controlled flows of purified hydrogen, carbon monoxide and a mixed olefin starting material of butene-1 and butene-2 (cis and trans) were fed through the sparger into the bottom of reactor 1 and the reactor pressure increased to the operating pressure given in TABLE 10 below. When the liquid level in reactor 1 started to increase as a result of liquid aldehyde product formation a portion of the liquid reaction solution of reactor 1 was pumped into reactor 2 through a line into the top of reactor 2 at a rate sufficient to maintain a constant liquid level in reactor 1. The pressure of reactor 2 increased to its operating pressure given in TABLE 10 below. Blow-off gas from reactor 2 was analyzed and measured. A controlled flow of make-up syn gas (CO and $H_2$) was added to reactor 2 in order to maintain their desired partial pressures in reactor 2. The operating pressures and reaction temperatures were maintained throughout the hydroformylation. As the liquid level in reactor 2 started to increase as a result of liquid aldehyde product formation, a portion of the liquid reaction solution was pumped to the vaporizer/separator at a rate sufficient to maintain a constant liquid level in reactor 2. The crude aldehyde product was separated at 115° C. and 20 psia. from the liquid reaction solution, condensed and collected in a product receiver. The remaining non-volatilized catalyst containing liquid reaction solution was recycled back to reactor 1.

The hydroformylation of said mixed olefin feed of butene-1 and butene-2 was carried out continuously for six days after which time the olefin feed was changed over to a predominately butene-1 feed and continued for an additional day.

The hydroformylation reaction conditions as well as the rate of $C_5$ aldehydes produced in terms of gram moles per liter per hour and the linear to branched aldehyde product ratio of n-valeraldehyde to 2-methylbutyraldehyde are given in TABLE 10 below.

TABLE 10

| Days of Operation | 2 | 6 | 7 |
|---|---|---|---|
| Butene Feed, mol % | | | |
| Butene-1 | 5.22 | 41.27 | 99.97 |
| Trans-Butene-2 | 57.00 | 34.06 | 0.0 |
| Cis-Butene-2 | 37.78 | 24.67 | 0.03 |
| Reactor No. 1 | | | |
| Temperature, °C. | 85.2 | 85.4 | 66.1 |
| Pressure, psia | 205 | 205 | 205 |
| $H_2$, psia | 86.3 | 64.2 | 78.3 |
| CO, psia | 63.7 | 63.1 | 75.9 |
| Butene-1, psia | 0.7 | 1.5 | 25.3 |
| Trans-Butene 2, psia | 23.0 | 18.5 | 1.1 |
| Cis-Butene-2, psia | 7.3 | 7.1 | 1.7 |
| Reactor No. 2 | | | |
| Temperature, °C. | 85.1 | 85.5 | 68.5 |
| Pressure, psia | 185 | 185 | 185 |
| $H_2$, psia | 83.8 | 55.1 | 54.4 |
| CO, psia | 37.9 | 54.8 | 52.0 |
| Butene-1, psia | 0.5 | 0.3 | 7.0 |
| Trans-Butene-2, psia | 16.2 | 11.0 | 2.1 |
| Cis-Butene-2, psia | 3.8 | 2.9 | 2.8 |
| Results | | | |
| $C_5$ Aldehydes, gmol/L/hr | 3.03 | 3.19 | 3.19 |
| Linear/Branched Aldehyde Ratio | 0.47 | 0.78 | 2.44 |

Subsequent analysis of the rhodium complex catalyst solution after completion of the above continuous seven day hydroformylation experiment showed said used catalyst solution to contain about 173 ppm rhodium.

A comparable experiment was conducted employing a similar procedure as described in Example 10 above, but wherein the crude aldehyde product was separated at vaporizer conditions of about 87° to 89° C. and about 5 psia. from the liquid reactor solution and wherein the recycled catalyst containing solution was passed through an Amberlyst ® A-21 bed to remove acidic by-products. After an equilibration period of one day wherein some rhodium was believed to be adsorbed onto the Amberlyst ® resin bed there were no detectable losses of rhodium inventory in the reactor over the next 10 days of continuous hydroformylation.

EXAMPLE 11

A similar continuous hydroformylation comparative experiment as set forth in Example 10 was carried out using tris-ortho-biphenylylphosphite, (Run No. 3 of TABLE 8, a phosphite not of this invention) as the ligand promoter. The start-up and operating procedure set forth in Example 10 were employed with the exception that in this test only a single reactor (in place of two reactors in series) was used with butene-1 as the olefin feed. The reactor was charged with 0.88 liters of a catalyst compositions consisting of 100 ppm rhodium as rhodium dicarbonyl acetylacetonate, 10 wt% tris-ortho-biphenylylphosphite (about 192 mole equivalents of phosphite ligand per mole equivalent of rhodium) dissolved in a 1:1 weight:weight mixture of valeraldehyde and Texanol ®. At the end of 0.8 days of operation massive percipitation of alpha-hydroxypentyl phosphonic acid occurred which caused plugging of the reactor transfer lines and subsequent shut-down of the continuous hydroformylation. Analysis of the catalyst solution by Phosphorous-31 Nuclear Magnetic Resonance Spectroscopy, showed that all tris-ortho-biphenylylphosphite had decomposed. The hydroformylation test was terminated. The data set forth in Table II below describes the operating conditions and performance prior to the forced shut-down of the process.

TABLE 11

| Days of operation | 0.8 |
|---|---|
| Butene Feed, mole % | |
| Butene-1 | 99.2 |
| Trans-Butene-2 | 0.2 |
| Cis-Butene-2 | 0.05 |
| Butane | 0.55 |
| Reaction Conditions | |
| Temperature, °C. | 80.3 |
| Pressure, Psia | 150.0 |
| $H_2$, Psia | 32.3 |
| CO, psia | 43.7 |
| Butene-1 psia | 60.6 |
| Results | |
| $C_5$ Aldehydes Reaction Rate (gmoles/liter/hour) | 1.02 |
| Linear/Branched Aldehyde Mole Ratio | 3.04 | was conducted at a total gas pressure of about 160 psig., the partial pressures of hydrogen, carbon monoxide, and propylene being given in Table 12 below, the remainder being nitrogen and aldehyde product. The flows of the feed gases (carbon monoxide, hydrogen, propylene and nitrogen) were controlled individually with mass flow meters and the feed gases dispersed into the precursor solution via fritted glass spargers. The unreacted portion of the feed gases stripped out the product $C_4$ aldehydes and the outlet gas analyzed over 22 days of continuous operation at the reaction temperatures given in TABLE 12 below. The average reaction rates for each experiment in terms of gram moles per liter per hour of product $C_4$ aldehydes as well as the n-butyraldehyde to iso-butyraldehyde product ratio are given in TABLE 12 below.

TABLE 12
TEST RESULTS - DAILY AVERAGES

| Days Opern. | Temp. °C. | Rhodium ppm* | Ligand wt. % | Partial Pressures CO psia | $H_2$ psia | Propylene psia | Reaction Rate gram moles/ Liter/Hour | Linear/ Branched Aldehyde Mole Ratio |
|---|---|---|---|---|---|---|---|---|
| 0.4 | 73 | 132 | 0.7 | 21 | 36 | 5 | 1.09 | 0.86 |
| 1.4 | 91 | 159 | 0.8 | 37 | 50 | 6 | 2.62 | 1.02 |
| 2.6 | 91 | 145 | 0.7 | 33 | 42 | 7 | 2.40 | 1.01 |
| 3.9 | 91 | 135 | 0.7 | 41 | 53 | 4 | 2.22 | 1.04 |
| 4.9 | 91 | 126 | 0.6 | 39 | 50 | 4 | 2.24 | 1.01 |
| 4.5 | 91 | 136 | 0.7 | 38 | 50 | 5 | 2.37 | 1.06 |
| 6.7 | 91 | 173 | 0.9 | 40 | 51 | 6 | 2.39 | 1.08 |
| 7.7 | 91 | 179 | 0.9 | 41 | 53 | 7 | 2.12 | 1.03 |
| 7.1 | 91 | 188 | 0.9 | 42 | 60 | 9 | 1.93 | 0.90 |
| 9.6 | 91 | 198 | 1.0 | 42 | 52 | 6 | 2.10 | 1.06 |
| 11.0 | 91 | 197 | 1.0 | 41 | 50 | 7 | 2.42 | 1.07 |
| 12.0 | 91 | 197 | 1.0 | 21 | 85 | 19 | 0.94 | 0.36 |
| 12.6 | 91 | 197 | 1.0 | 41 | 50 | 8 | 2.35 | 1.06 |
| 13.7 | 89 | 209 | 1.1 | 29 | 78 | 14 | 1.86 | 0.77 |
| 14.7 | 88 | 209 | 1.1 | 41 | 50 | 8 | 2.56 | 1.09 |
| 15.6 | 101 | 214 | 1.1 | 42 | 50 | 9 | 2.40 | 1.05 |
| 16.9 | 91 | 199 | 1.0 | 40 | 50 | 8 | 2.46 | 1.08 |
| 17.9 | 91 | 200 | 1.0 | 41 | 50 | 8 | 2.46 | 1.07 |
| 18.9 | 91 | 202 | 1.0 | 41 | 50 | 9 | 2.38 | 1.07 |
| 19.6 | 91 | 204 | 1.0 | 40 | 50 | 9 | 2.48 | 1.07 |
| 22.5 | 92 | 209 | 1.0 | 42 | 50 | 8 | 2.34 | 1.08 |

*Changing values reflect change in daily liquid reactor solution levels

EXAMPLE 12

The long term catalyst stability of 1,1'-biphenyl-2,2'-diyl-(2,6-di-tert-butyl-4-methylphenyl)phosphite promoted rhodium catalyst was determined in the following manner.

The hydroformylation was conducted in a glass reactor operating in a continuous single pass propylene hydroformylation mode. The reactor consisted of a three-ounce pressure bottle submersed in an oil bath with a glass front for viewing. About 20-mL of a freshly prepared rhodium catalytic precursor solution was charged to the reactor with a syringe, after purging the system with nitrogen. The precursor solution contained about 200 ppm rhodium introduced as rhodium dicarbonyl acetylacetonate, about 10 mole equivalents of 1,1'-biphenyl-2,2'-diyl-(2,6-di-tert-butyl-4-methylphenyl)-phosphite ligand per mole of rhodium metal and Texanol ® as the solvent. After closing the reactor, the system was again purged with nitrogen and the oil bath was heated to furnish the desired hydroformylation reaction temperature. The hydroformulation reaction

EXAMPLE 13

A similar continuous hydroformylation experiment as set forth in Example 10 was carried out using isobutylene as the olefin and phenyl [2,2'-methylene-bis(6-t-butyl-4-methylphenyl)]phosphite (the ligand in Run No. 3 of Table 6) as the ligand promoter. The start-up and operating procedure set forth in Example 10 were employed with the exception that only a single reactor (in place of the two reactors in series) was used with isobutylene as the olefin feed and the above mentioned phosphite as the ligand. The reactor was charged with 1127 mL. of a catalyst composition consisting of 200 ppm rhodium as rhodium dicarbonyl acetylacetonate, 0.9 wt. % of phenyl [2,2'-methylene-bis(6-t-butyl-4-methylphenyl)]phosphite (about 10 mole equivalents of phosphite ligand per mole equivalent of rhodium) dissolved in a mixture of about 475 gr. of valeraldehyde and about 466 gr. of Texanol ®. The data set forth in Table 13 below describes the operating conditions and performance in gram moles per liter per hour of 3- methylbutyraldehyde product over three days of continuous hydroformylation.

TABLE 13

| Days of Operation | 1 | 2 | 3 |
|---|---|---|---|
| Olefin Feed Mole % | | | |
| Isobutylene | 99.96 | 99.94 | 100 |
| Isobutane | 0.04 | 0.06 | — |
| Reaction Conditions | | | |
| Temperature, °C. | 84.8 | 84.8 | 84.8 |
| Pressure, Psia | 201 | 204 | 206 |
| H$_2$, Psia | 73.92 | 75.65 | 65.76 |
| CO, Psia | 3.34 | 7.98 | 41.64 |
| Isobutylene, Psia | 106.0 | 98.24 | 85.59 |
| Results | | | |
| 3-Methylbutyraldehyde Reaction Rate (g moles/liter/hour) | 1.55 | 1.60 | 0.64 |

EXAMPLE 14

Butene-2 was hydroformylated in the same manner as Example 12 using 1,1'-binaphthylene-2,2'-diyl-(2,6-di-t-butyl-4-methylphenyl)phosphite as the ligand, (the ligand of Run No. 9 of Table 3).

The hydroformylation was conducted in a glass reactor operating in a continuous single pass butene-2 hydroformylation mode. The reactor consisted of a three ounce pressure bottle submersed in an oil bath with a glass front for viewing. About 20 mL of a freshly prepared rhodium catalytic precursor solution was charged to the reactor with a syringe after purging the system with nitrogen. The precursor solution contained about 200 ppm rhodium introduced as rhodium dicarbonyl acetylacetonate, about 9.6 mole equivalents of 1,1'-binaphthylene-2,2'-diyl-(2,6-di-tert-butyl-4-methylphenyl)phosphite ligand per mole of rhodium metal and Texanol ® as the solvent. After closing the reactor, the system was again purged with nitrogen and the oil bath was heated to furnish the desired hydroformylation reaction temperature. The hydroformylation reaction was conducted at a total gas pressure of about 160 psig., the partial pressures of hydrogen, carbon monoxide, and butene-2 being given in Table 14 below, the remainder being nitrogen and aldehyde product. The flows of the feed gases (carbon monoxide, hydrogen and butene-2) were controlled individually with mass flow meters and the feed gases dispersed into the precursor solution via fritted glass spargers. The unreacted portion of the feed gases stripped out the product C$_5$ aldehydes and the outlet gas analyzed over about 14 days of continuous operation at the reaction temperatures given in TABLE 14 below. The average reaction rates for each experiment in terms of gram moles per liter per hour of product C$_5$ aldehydes as well as the linear n-valeraldehyde to 2-methylbutyraldehyde branched product ratio are given in TABLE 14 below.

TABLE 14

TEST RESULTS - DAILY AVERAGES

| Days Opern. | Temp. °C. | Rhodium ppm* | Ligand wt. %* | Partial Pressures | | | Reaction Rate gram moles/ Liter/Hour | Linear/Branched Aldehyde Mole Ratio |
|---|---|---|---|---|---|---|---|---|
| | | | | CO psia | H$_2$ psia | Butene-2 psia | | |
| 0.8 | 102 | 146 | 0.7 | 42 | 48 | 18 | 1.10 | 0.20 |
| 1.6 | 100 | 162 | 0.8 | 32 | 39 | 22 | 1.52 | 1.30 |
| 2.2 | 100 | 163 | 0.8 | 34 | 41 | 24 | 1.74 | 1.20 |
| 3.8 | 100 | 153 | 0.8 | 34 | 49 | 25 | 1.79 | 1.07 |
| 4.5 | 100 | 156 | 0.8 | 32 | 39 | 23 | 1.74 | 1.18 |
| 4.6 | 100 | 186 | 0.9 | 33 | 40 | 24 | 1.68 | 1.36 |
| 6.7 | 100 | 223 | 1.1 | 33 | 40 | 25 | 1.73 | 1.39 |
| 7.7 | 100 | 86 | 0.4 | 30 | 37 | 22 | 1.06 | 0.84 |
| 7.1 | 100 | 171 | 0.9 | 34 | 40 | 35 | 1.80 | 1.09 |
| 10.7 | 100 | 189 | 1.9 | 34 | 39 | 36 | 1.85 | 1.19 |
| 11.8 | 110 | 183 | 1.9 | 35 | 41 | 35 | 1.86 | 1.00 |
| 12.8 | 110 | 215 | 1.1 | 35 | 41 | 37 | 2.08 | 1.12 |
| 13.6 | 110 | 260 | 1.3 | 36 | 42 | 38 | 1.76 | 1.28 |

*Changing values reflect changes in daily liquid reactor solution levels.

EXAMPLE 15

Isobutylene was hydroformylated in the same manner as Example 12 using 1,1'-biphenyl-2,2'-diyl-(2,6-di-tert-butyl-4-methylphenyl)phosphite as the ligand (the ligand of Example 1).

The hydroformylation was conducted in a glass reactor operating in a continuous single pass isobutylene hydroformylation mode. The reactor consisted of a three ounce pressure bottle submersed in an oil bath with a glass front for viewing. About 20 mL of a freshly prepared rhodium catalytic precursor solution eas charged to the reactor with a syringe after purging the system with nitrogen. The precursor solution contained about 250 ppm rhodium introduced as rhodium dicarbonyl acetylacetonate, about 10 mole equivalents of 1,1'-biphenyl-2,2'-diyl-(2,6-di-tert-butyl-4-methylphenyl)-phosphite ligand per mole of rhodium metal and Texanol ® as the solvent. After closing the reactor, the system was again purged with nitrogen and the oil bath was heated to furnish the desired hydroformylation reaction temperature. The hydroformylation reaction was conducted at a total gas pressure of about 160 psig., the partial pressures of hydrogen, carbon monoxide, and isobutylene being given in Table 15 below, the remainder being nitrogen and aldehyde product. The flows of the feed gases (carbon monoxide, hydrogen and isobutylene) were controlled individually with mass flow meters and the feed gases dispersed into the precursor solution via fritted glass spargers. The unreacted portion of the feed gases stripped out the 3-methylbutyraldehyde product and the outlet gas analyzed over 7 days of continuous operation at the reaction temperatures given in TABLE 15 below. The average reaction rates for each experiment in terms of gram moles per liter per hour of 3-methylbutyraldehyde product is given in Table 15 below.

TABLE 15
TEST RESULTS - DAILY AVERAGES

| Days Opern. | Temp. °C. | Rhodium ppm* | Ligand wt. %* | Partial Pressures | | | Reaction Rate gram moles/ Liter/Hour |
| | | | | CO psia | $H_2$ psia | Isobutylene psia | |
|---|---|---|---|---|---|---|---|
| 0.8 | 99 | 179 | 0.8 | 32 | 69 | 27 | 1.09 |
| 1.7 | 115 | 252 | 1.1 | 31 | 85 | 51 | 1.46 |
| 2.7 | 115 | 226 | 1.0 | 26 | 26 | 96 | 1.54 |
| 3.1 | 115 | 207 | 0.9 | 83 | 74 | 11 | 1.48 |
| 5.8 | 115 | 279 | 1.2 | 70 | 73 | 26 | 0.68 |
| 6.6 | 115 | 205 | 0.9 | 72 | 71 | 26 | 0.58 |
| 7.1 | 115 | 210 | 0.9 | 63 | 62 | 43 | 0.84 |

*Changing values reflect change in daily liquid reactor solution levels

EXAMPLE 16

Methyl [3,3'-di-t-butyl-5,5'-dimethoxy-1,1'-biphenyl-2,2'-diyl]phosphite having the formula

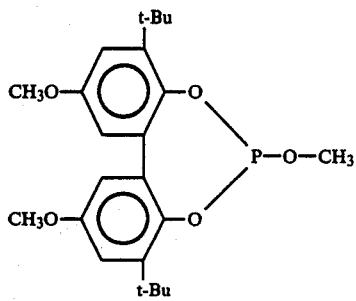

was prepared in the following manner.

A solution of about 90 grams (about 0.5 moles) of 2-t-butyl-4-methoxyphenol and 170 ml. of $H_2O$ containing about 56 grams (about 1.0 mole) of potassium hydroxide was heated with stirring to about 80° C. Air was then passed through the solution until precipitation of a diphenolic compound (i.e. 2,2'-dihydroxy-3,3'-di-t-butyl-5,5'-dimethoxy-1,1'-biphenyl) was complete (total reaction time of about 135 minutes). The white, solid diphenolic precipitate was then filtered hot and washed twice with about 200 ml. of water. About 78 grams (87.6% of theory) of the isolated 2,2'-dihydroxy-3,3'-di-t-butyl-5,5'-dimethoxy-1,1'-biphenyl product was recovered which had a melting point of about 222° to 224° C. and whose structure was confirmed by infrared and mass spectroscopy.

About 75.2 grams of the 2,2'-dihydroxy-3,3'-di-t-butyl-5,5'-dimethoxy-1,1'-biphenyl diol so prepared was then added to about 1 liter of toluene. Sufficient toluene was then removed azeotropically to remove residual traces of moisture from the solution. The diol-toluene solution was then cooled to 0° C. and about 70 grams of triethylamine added followed by the dropwise addition of about 29 grams of phosphorus trichloride at 0° C. over about 20 minutes. The reaction solution became thick with triethylamine hydrochloride salt and was heated for about 30 minutes at about 100° C. The suspension was then cooled to about 55° C. and about 13.44 grams of methanol added over about 15 minutes and the reaction medium heated at about 90° to 95° C. for about one hour. The reaction medium was then filtered hot to remove the solid triethylamine hydrochloride precipitate and the filtrate evaporated to dryness under vacuum. The recovered residue was then dissolved in about 100 ml. of refluxing acetonitrile and cooled to precipitate the desired methyl [3,3'-di-t-butyl-5,5'-dimethoxy-1,1'-biphenyl-2,2'-diyl]phosphite ligand, about 75 grams (85.4% yield of theory) of which was recovered. The desired crystalline, solid phosphite ligand product was found to have a melting point of about 64° to 69° C. and a characteristic $^{31}P$ NMR phosphite resonance at 131.9 ppm (relative to external $H_3PO_4$).

EXAMPLE 17

The following diorganophosphite ligands were prepared in the same manner as described in Example 16 above, save of course for employing the hydroxy compound reactants that correspond to and account for their diorganophosphite structures.

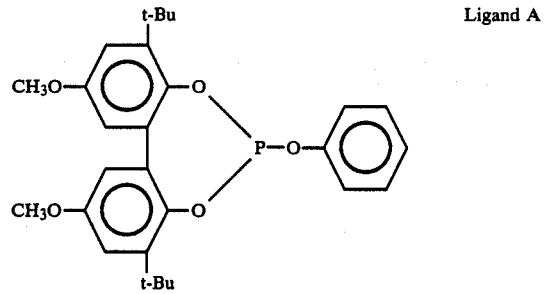

Ligand A phenyl [3,3'-di-t-butyl-5,5'-dimethoxy-1,1'-biphenyl-2,2'-diyl]phosphite. (Crystalline product having a melting point of 131° to 132° C. and having a characteristic $^{31}P$ NMR phosphite resonance at 140.1 ppm, relative to external $H_3PO_4$)

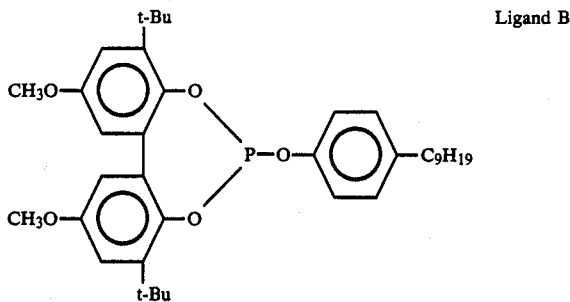

Ligand B 4-nonylphenyl [3,3'-di-t-butyl-5,5'-dimethoxy-1,1'-biphenyl-2,2'-diyl]phosphite (Non-crystalline gum product having a characteristic $^{31}P$ NMR phosphite resonances at 140.1 ppm and 139.9 ppm, relative to external $H_3PO_4$; "nonyl" represents branched mixed nonyl radicals).

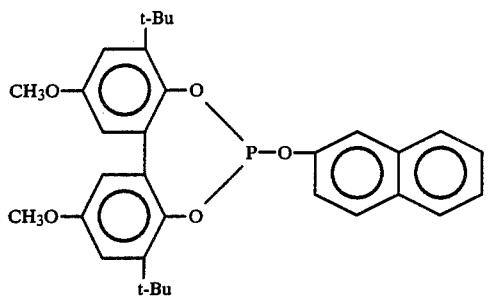

Ligand C beta-naphthyl [3,3'-di-t-butyl-5,5'-dimethoxy-1,1'-biphenyl-2,2'-diyl]phosphite (Non-crystalline gum product having a characteristic $^{31}P$ NMR phosphite resonance at 139.2 ppm, relative to external $H_3PO_4$).

EXAMPLE 18

Butene-2 was hydroformylated in the same manner as Example 12 using methyl [3,3'-di-t-butyl-5,5'-dimethoxy-1,1'-biphenyl-2,2'-diyl]phosphite as the ligand, (the ligand of Example 16).

The hydroformylation was conducted in a glass reactor operating in a continuous single pass butene-2 hydroformylation mode. The reactor consisted of a three ounce pressure bottle submersed in an oil bath with a glass front for viewing. About 20 mL of a freshly prepared rhodium catalytic precursor solution was charged to the reactor with a syringe after purging the system with nitrogen. The precursor solution contained about 250 ppm rhodium introduced as rhodium dicarbonyl acetylacetonate, about 2.0 weight percent ligand (about 19.7 mole equivalents of methyl [3,3'-di-t-butyl-5,5'-dimethoxy-1,1'-biphenyl-2,2'-diyl]phosphite ligand per mole of rhodium metal) and valeraldehyde trimer as the solvent. After closing the reactor, the system was again purged with nitrogen and the oil bath was heated to furnish the desired hydroformylation reaction temperature. The hydroformylation reaction was conducted at a total gas pressure of about 160 psig., the partial pressures of hydrogen, carbon monoxide, and butene-2 being given in Table 16 below, the remainder being nitrogen and aldehyde product. The flows of the feed gases (carbon monoxide, hydrogen and butene-2) were controlled individually with mass flow meters and the feed gases dispersed into the precursor solution via fritted glass spargers. The unreacted portion of the feed gases stripped out the product $C_5$ aldehydes and the outlet gas analyzed over about 11 days of continuous operation at the reaction temperature of about 90° C. given in TABLE 16 below. The average reaction rates for this experiment in terms of gram moles per liter per hour of product $C_5$ aldehydes as well as the linear n-valeraldehyde to 2-methylbutyraldehyde branched product ratio are given in TABLE 16 below.

TABLE 16

TEST RESULTS - DAILY AVERAGES

| Days Opern. | Temp. °C. | Partial Pressures | | | Reaction Rate gram moles/ Liter/Hour | Linear/ Branched Aldehyde Mole Ratio |
|---|---|---|---|---|---|---|
| | | CO psia | $H_2$ psia | Butene-2 psia | | |
| 0.5 | 90 | 26 | 72 | 10 | 0.7 | 0.3 |
| 3.5 | 90 | 20 | 59 | 12 | 1.7 | 0.7 |
| 4.5 | 90 | 20 | 60 | 10 | 1.5 | 0.6 |
| 5.5 | 90 | 20 | 60 | 10 | 1.5 | 0.6 |
| 6.5 | 90 | 20 | 60 | 10 | 1.7 | 0.6 |
| 7.5 | 90 | 21 | 60 | 8 | 1.5 | 0.7 |
| 10.5 | 90 | 20 | 60 | 10 | 1.6 | 0.6 |
| 10.9 | 90 | 20 | 58 | 12 | 1.9 | 0.7 |

EXAMPLE 19

Butene-2 was hydroformylated in the same manner as Example 12 using phenyl[3,3'-di-t-butyl-5,5'-dimethoxy-1,1'-biphenyl-2,2'-diyl]phosphite as the ligand, (Ligand A of Example 17).

The hydroformylation was conducted in a glass reactor operating in a continuous single pass butene-2 hydroformylation mode. The reactor consisted of a three ounce pressure bottle submersed in an oil bath with a glass front for viewing. About 20 mL of a freshly prepared rhodium catalytic precursor solution was charged to the reactor with a syringe after purging the system with nitrogen. The precursor solution contained about 250 ppm rhodium introduced as rhodium dicarbonyl acetylacetonate, about 2.0 weight percent ligand (about 17.2 mole equivalents of phenyl[3,3'-di-t-butyl-5,5'-dimethoxy-1,1'-biphenyl-2,2'-diyl]phosphite ligand per mole of rhodium metal) and valeraldehyde trimer as the solvent. After closing the reactor, the system was again purged with nitrogen and the oil bath was heated to furnish the desired hydroformylation reaction temperature. The hydroformylation reaction was conducted at a total gas pressure of about 160 psig., the partial pressures of hydrogen, carbon monoxide, and butene-2 being given in Table 17 below, the remainder being nitrogen and aldehyde product. The flows of the feed gases (carbon monoxide, hydrogen and butene-2) were controlled individually with mass flow meters and the feed gases dispersed into the precursor solution via fritted glass spargers. The unreacted portion of the feed gases stripped out the product $C_5$ aldehydes and the outlet gas analyzed over about 13 days of continuous operation at the reaction temperature of about 90° C. given in TABLE 17 below. The average reaction rates for this experiment in terms of gram moles per liter per hour of product $C_5$ aldehydes as well as the linear n-valeraldehyde to 2-methylbutyraldehyde branched product ratio are given in TABLE 17 below. Analysis after 2.5 days of operation indicated poor butene-2 feed due to plugging of the sparger. The problem was corrected and the reaction continued.

TABLE 17

TEST RESULTS - DAILY AVERAGES

| Days Opern. | Temp. °C. | Partial Pressures | | | Reaction Rate gram moles/ Liter/Hour | Linear/ Branched Aldehyde Mole Ratio |
|---|---|---|---|---|---|---|
| | | CO psia | $H_2$ psia | Butene-2 psia | | |
| 0.5 | 90 | 23 | 65 | 10 | 1.4 | 0.7 |

TABLE 17-continued

TEST RESULTS - DAILY AVERAGES

| Days Opern. | Temp. °C. | Partial Pressures | | | Reaction Rate gram moles/ Liter/Hour | Linear/ Branched Aldehyde Mole Ratio |
| | | CO psia | H$_2$ psia | Butene-2 psia | | |
|---|---|---|---|---|---|---|
| 1.5 | 90 | 20 | 60 | 9 | 1.8 | 0.8 |
| 2.5 | 90 | 43 | 6 | 1 | 0.04 | — |
| 5.5 | 90 | 21 | 59 | 14 | 1.8 | 0.8 |
| 6.5 | 90 | 21 | 59 | 13 | 2.0 | 0.8 |
| 7.5 | 90 | 21 | 60 | 12 | 1.8 | 0.7 |
| 8.5 | 90 | 22 | 60 | 12 | 1.9 | 0.7 |
| 9.5 | 90 | 22 | 60 | 10 | 1.8 | 0.7 |
| 12.5 | 90 | 21 | 60 | 12 | 1.8 | 0.7 |
| 12.9 | 90 | 21 | 60 | 13 | 1.7 | 0.7 |

EXAMPLE 20

Butene-2 was hydroformylated in the same manner as Example 12 using 4-nonyl[3,3'-di-t-butyl,-5,5'-dimethoxy-1,1'-biphenyl-2,2'-diyl]phosphite as the ligand, (Ligand B of Example 17).

The hydroformylation was conducted in a glass reactor operating in a continuous single pass butene-2 hydroformylation mode. The reactor consisted of a three ounce pressure bottle submersed in an oil bath with a glass front for viewing. About 20 mL of a freshly prepared rhodium catalytic precursor solution was charged to the reactor with a syringe after purging the system with nitrogen. The precursor solution contained about 250 ppm rhodium introduced as rhodium dicarbonyl acetylacetonate, about 2.0 weight percent ligand (about 13.6 mole equivalents of 4-nonyl[3,3'-di-t-butyl-5,5'-dimethoxy-1,1'-biphenyl-2,2'-diyl]phosphite ligand per mole of rhodium metal) and valeraldehyde trimer as the solvent. After closing the reactor, the system was again purged with nitrogen and the oil bath was heated to furnish the desired hydroformylation reaction temperature. The hydroformylation reaction was conducted at a total gas pressure of about 160 psig., the partial pressures of hydrogen, carbon monoxide, and butene-2 being given in Table 18 below, the remainder being nitrogen and aldehyde product. The flows of the feed gases (carbon monoxide, hydrogen and butene-2) were controlled individually with mass flow meters and the feed gases dispersed into the precursor solution via fritted glass spargers. The unreacted portion of the feed gases stripped out the product C$_5$ aldehydes of the outlet gas analyzed over about 13 days of continuous operation at the reaction temperature of about 90° C. given in TABLE 18 below. The average reaction rates for this experiment in terms of gram moles per liter per hour of product C$_5$ aldehydes as well as the linear n-valeraldehyde to 2-methylbutyraldehyde branched product ratio are given in TABLE 18 below.

TABLE 18

TEST RESULTS - DAILY AVERAGES

| Days Opern. | Temp. °C. | Partial Pressures | | | Reaction Rate gram moles/ Liter/Hour | Linear/ Branched Aldehyde Mole Ratio |
| | | CO psia | H$_2$ psia | Butene-2 psia | | |
|---|---|---|---|---|---|---|
| 0.5 | 90 | 20 | 60 | 15 | 1.0 | 0.7 |
| 1.5 | 90 | 16 | 70 | 12 | 1.2 | 1.0 |
| 2.5 | 90 | 15 | 70 | 15 | 1.5 | 1.0 |
| 5.5 | 90 | 16 | 68 | 15 | 1.7 | 1.5 |
| 6.5 | 90 | 16 | 69 | 14 | 1.8 | 1.5 |
| 7.5 | 90 | 17 | 70 | 12 | 1.7 | 1.5 |
| 8.5 | 90 | 16 | 70 | 13 | 1.8 | 1.5 |
| 9.5 | 90 | 17 | 70 | 12 | 1.6 | 1.5 |
| 12.5 | 90 | 16 | 70 | 14 | 1.7 | 1.6 |
| 12.9 | 90 | 16 | 70 | 13 | 1.5 | 1.7 |

EXAMPLE 21

A similar continuous hydroformylation experiment as set forth in Example 10 was carried out using isobutylene as the olefin and methyl[3,3'-di-t-butyl-5,5'-dimethoxy-1,1'-biphenyl-2,2'-diyl]phosphite (the ligand of Example 16) as the ligand promoter. The start-up and operating procedure set forth in Example 10 was employed.

The hydroformylation reaction was conducted by charging about 1.03 liters of a catalyst precursor solution of rhodium dicarbonyl acetylacetonate (about 450 ppm rhodium), about 2.8 wt. methyl[3,3'-di-t-butyl-5,5'-dimethoxy-1,1'-biphenyl-2,2'-diyl)phosphite ligand (about 15.3 mole equivalents of ligand per mole of rhodium), about 2.0 triphenylphosphine oxide as an internal standard, and about 95.8 wt. % of C$_5$ aldehyde (about 82.8 wt. % valeraldehyde and about 13.0 wt % valeraldehyde trimer) as solvent to reactor 1. About 1.2 liters of the same catalyst precursor solution was charged to reactor 2. The reactor system was then purged with nitrogen to remove any oxygen present. Then about 100 psig. nitrogen pressure was put on both reactors and the reactors heated to their reaction temperatures given in TABLE 19 below. Controlled flows of purified hydrogen, carbon monoxide and isobutylene (the composition of the isobutylene feed throughout this process consisted of at least 99.9 mole % or greater of isobutylene, any remainder being isobutane) were fed through the sparger into the bottom of reactor 1 and the reactor pressure increased to the operating pressure given in TABLE 19 below. When the liquid level in reactor 1 started to increase as a result of liquid aldehyde product formation a portion of the liquid reaction solution of reactor 1 was pumped into reactor 2 through a line into the top of reactor 2 at a rate sufficient to maintain a constant liquid level in reactor 1. The pressure of reactor 2 increased to its operating pressure given in TABLE 19 below. Blow-off gas from reactor 2 was analyzed and measured. A controlled flow of make-up syn gas (CO and H$_2$) was added to reactor 2 in order to maintain their desired partial pressures in reactor 2. The operating pressures and reaction temperatures were maintained throughout the hydroformylation. As the liquid level in reactor 2 started to increase as a result of liquid aldehyde product formation, a portion of the liquid reaction solution was pumped to the vaporizer/separator at a rate sufficient to maintain a constant liquid level in reactor 2. The crude aldehyde product was separated (at varying temperatures) from the liquid reaction solution, condensed and collected in a product receiver. The remaining non-volatilized catalyst containing liquid reaction solution was recycled back to reactor 1.

The hydroformylation experiment was carried out continuously for about 33 days. During the first 15 days of operation the aldehyde product was separated from the liquid reaction solution at about 115° C. and 22–26 psia.; from day 16 to day 19 this separation was conducted at about 117° C. and 22–26 psia; from day 19 through day 22 this separation was conducted at about 123° C. and 22–26 psia. and from day 23 to day 32.5 this separation was conducted at 133° C. and 22–26 psia.

The data set forth in TABLE 19 below describes the operating conditions and performance in gram moles per liter per hour of 3-methylbutyraldehyde product over about 33 days of continuous hydroformylation.

TABLE 19

| Days of Operation | 6.9 | 13.9 | 21.8 | 32.5 |
|---|---|---|---|---|
| Reactor No. 1 | | | | |
| Temperature, °C. | 95.0 | 95.0 | 94.9 | 95.5 |
| Pressure, psia | 185 | 185 | 185 | 185 |
| $H_2$, psia | 72.7 | 70.8 | 70.6 | 62.5 |
| CO, psia | 57.9 | 55.2 | 53.1 | 55.9 |
| Isobutylene, psia | 34.3 | 37.5 | 39.7 | 46.9 |
| Reactor No. 2 | | | | |
| Temperature, °C. | 95.3 | 95.4 | 95.5 | 95.4 |
| Pressure, psia | 165 | 165 | 165 | 165 |
| $H_2$, psia | 76.3 | 75.0 | 73.0 | 66.1 |
| CO, psia | 48.4 | 43.3 | 49.2 | 53.6 |
| Isobutylene, psia | 13.7 | 15.4 | 16.4 | 24.3 |
| Results | | | | |
| 3-Methylbutyraldehyde (g mol/L/hr) | 1.77 | 1.81 | 1.74 | 1.49 |

The rhodium inventory in the reactor system was monitored daily during the course of the experiment and no detectable loss of rhodium in the reactor system was observed over the first 26 days of continuous hydroformylation. However, continued analysis showed that about a 10 percent loss of rhodium inventory in the reactor system occurred over the continuous period from day 26 to day 32.5 (completion of the experiment).

The above experiment demonstrates the high rhodium complex catalyst activity and stability obtained in employing methyl[3,3'-di-t-butyl-5,5'-dimethoxy-1,1'-biphenyl-2,2'-diyl]phosphite ligand when hydroformylating even a normally highly unreactive olefin, such as isobutylene. In addition, said experiment demonstrates that the use of a ligand such as methyl[3,3'-di-t-butyl-5,5'-dimethoxy-1,1'-biphenyl-2,2'-diyl]phosphite permitted the crude aldehyde product to be separated from the liquid reaction solution at vaporization temperatures even as high as about 120° C. without experiencing any loss in rhodium inventory over a prolonged period of operation, while the steady production of 3-methylbutyraldehyde indicates the ligand's high stability against in situ phosphite decomposition to undesirable hydroxy alkyl phosphonic acid by-product.

EXAMPLE 22

Butene-1 was hydroformylated in the same manner as Example 12 using beta-naphthyl[3,3'-di-t-butyl-5,5'-dimethoxy-1,1'-biphenyl-2,2'-diyl]phosphite as the ligand, (Ligand C of Example 17).

The hydroformylation was conducted in a glass reactor operating in a continuous single pass butene-1 hydroformylation mode. The reactor consisted of a three ounce pressure bottle submersed in an oil bath with a glass front for viewing. About 20 mL of a freshly prepared rhodium catalytic precursor solution was charged to the reactor with a syringe after purging the system with nitrogen. The precursor solution contained about 25 ppm rhodium introduced as rhodium dicarbonyl acetylacetonate, about 2.0 weight percent ligand (about 155 mole equivalents of beta-naphthyl[3,3'-di-t-butyl-5,5'-dimethoxy-1,1'-biphenyl-2,2'-diyl]phosphite ligand per mole of rhodium metal) and valeraldehyde trimer as the solvent. After closing the reactor, the system was again purged with nitrogen and the oil bath was heated to furnish the desired hydroformylation reaction temperature. The hydroformylation reaction was conducted at a total gas pressure of about 160 psig., the partial pressures of hydrogen, carbon monoxide, and butene-1 being given in Table 20 below, the remainder being nitrogen and aldehyde product. The flows of the feed gases (carbon monoxide, hydrogen and butene-1) were controlled individually with mass flow meters and the feed gases dispersed into the precursor solution via fritted glass spargers. The unreacted portion of the feed gases stripped out the product $C_5$ aldehydes and the outlet gas analyzed over about 14 days of continuous operation at the reaction temperature of about 90° C. given in TABLE 20 below. The average reaction rates for each experiment in terms of gram moles per liter per hour of product $C_5$ aldehydes as well as the linear n-valeraldehyde to 2-methylbutyraldehyde branched product ratio are given in TABLE 20 below. The decreasing reaction rate of $C_5$ aldehydes produced over time is considered attributable to the very low concentration of rhodium employed.

TABLE 20

| TEST RESULTS - DAILY AVERAGES | | | | | |
|---|---|---|---|---|---|
| | | Partial Pressures | | | Reaction Rate gram | Linear/ Branched |
| Days Opern. | Temp. °C. | CO psia | $H_2$ psia | Butene-1 psia | moles/ Liter/Hour | Aldehyde Mole Ratio |
| 0.5 | 90 | 12 | 44 | 38 | 1.1 | 4.0 |
| 1.5 | 90 | 9 | 40 | 35 | 1.5 | 4.0 |
| 2.5 | 90 | 8 | 38 | 30 | 1.7 | 3.7 |
| 3.5 | 90 | 9 | 41 | 25 | 1.5 | 4.0 |
| 4.5 | 90 | 10 | 42 | 28 | 1.2 | 4.0 |
| 5.5 | 90 | 11 | 42 | 29 | 1.0 | 5.0 |
| 7.5 | 90 | 12 | 43 | 30 | 0.7 | 6.0 |
| 8.5 | 90 | 12 | 43 | 20 | 0.5 | 7.0 |
| 9.5 | 90 | 12 | 44 | 27 | 0.5 | 8.0 |
| 10.5 | 90 | 12 | 43 | 28 | 0.5 | 9.0 |
| 11.5 | 90 | 12 | 43 | 28 | 0.6 | 9.0 |
| 12.5 | 90 | 12 | 44 | 28 | 0.5 | 8.0 |
| 13.5 | 90 | 12 | 44 | 28 | 0.5 | 8.0 |
| 13.9 | 90 | 12 | 43 | 29 | 0.4 | 8.0 |

EXAMPLE 23

A similar continuous hydroformylation experiment as set forth in Example 10 was conducted and the formation of hydroxyalkyl phosphonic acid monitored.

The hydroformylation reaction was conducted by charging about 770 mL of a catalyst precursor solution of rhodium dicarbonyl acetylacetonate (about 492 ppm rhodium), about 3.5 wt. % 1,1'-biphenyl-2,2'-diyl-(2,6-di-tert-butyl-4-methylphenyl)phosphite ligand (about 16.8 mole equivalents of ligand per mole of rhodium), and about 96.3 wt. % of $C_5$ aldehyde (about 69.3 wt % valeraldehyde and about 27 wt % valeraldehyde trimer) as solvent to reactor 1. About 900 mililiters of the same catalyst precursor solution was charged to reactor 2. The start-up and operating procedures set forth in Example 10 were employed.

The hydroformylation reaction conditions as well as the rate of $C_5$ aldehydes produced in terms of gram moles per liter per hour and the linear to branched aldehyde product ratio of n-valeraldehyde to 2-methybutyraldehyde are given in TABLE 21 below.

TABLE 21

| Days of Operation | 7 | 11 | 12 |
|---|---|---|---|
| Butene Feed, mol % | | | |
| Butene-1 | 41.9 | 37.4 | 40.2 |
| Trans-Butene-2 | 35.1 | 38.2 | 36.4 |
| Cis-Butene-2 | 22.9 | 24.4 | 23.4 |
| Reactor No. 1 | | | |
| Temperature, °C. | 70.4 | 65.6 | 65.1 |
| Pressure, psia | 205 | 205 | 205 |
| $H_2$, psia | 88.7 | 86.4 | 82.4 |
| CO, psia | 19.7 | 33.0 | 46.9 |
| Butene-1, psia | 3.9 | 5.6 | 9.7 |
| Trans-Butene 2 and Cis-Butene-2, psia | 38.9 | 39.7 | 39.4 |
| Reactor No. 2 | | | |
| Temperature, °C. | 90.7 | 95.5 | 95.3 |
| Pressure, psia | 185 | 185 | 185 |
| $H_2$, psia | 89.1 | 77.9 | 69.7 |
| CO, psia | 8.6 | 23.2 | 39.7 |
| Butene-1, psia | 1.4 | 2.3 | 2.2 |
| Trans-Butene-2 and Cis-Butene-2, psia | 37.1 | 46.1 | 49.7 |
| Results | | | |
| $C_5$ Aldehydes, gmol/L/hr | 2.89 | 2.76 | 2.31 |
| Linear/Branched Aldehyde Ratio | 1.87 | 1.34 | 1.39 |

During this hydroformylation experiment the hydroformylation reaction medium was monitored by routinely withdrawing samples of the continuous catalyst-containing hydroformylation reaction medium from reactor 1 and examining same via $^{31}P$ NMR spectroscopy for a detectable signal (resonance peak) of alpha-hydroxypentyl phosphonic acid. A comparative synthetic solution containing 100 ppm (concentration by weight) of alpha-hydroxypentyl phosphonic acid which gave a detectable phosphonic acid signal (resonance peak) at about 25.8 ppm relative to external $H_3PO_4$ in the $^{31}P$ NMR after 2000 pulses (transients) was employed as the standard. Such set the low detection limit of the alpha-hydroxypentyl phosphonic acid at about 100 ppm (concentration by weight).

After about 10 days of continuous hydroformylation no detectable amount of alpha-hydroxypentyl phosphonic acid showed up on the $^{31}P$ NMR spectrum. At day 11 of the continuous operation however, a small qualitative amount of alpha-hydroxypentyl phosphonic acid had formed as evidenced by a small phosphonic acid resonance peak that appeared on the spectrum of the $^{31}P$ NMR conducted that day. At this point on day 11 an Amberlyst ® A-21 ion exchange resin bed was employed in the catalyst recycle line of the liquid recycle process and the catalyst containing recycle solution, after removal of the desired aldehyde product, passed through said bed on its return to the reactor. Within hours the alpha-hydroxypentyl phosphonic acid was scavenged from the reaction hydroformylation reaction medium as evidenced by the disappearance of the detectable phosphonic acid peak in the $^{31}P$ NMR spectrum for the sample of the hydroformylation reaction medium recorded on day 12. Note in this experiment a commercial grade Amberlyst ® A-21 resin was employed. Apparently this resin contained chloride impurities which contaminated (poisoned) a portion of the rhodium catalyst, as evidenced by new rhodium-ligand complex peaks on the $^{31}P$ NMR spectra.

EXAMPLE 24

A similar continuous hydroformylation experiment as set forth in Example 10 was conducted and the formation of hydroxyalkyl phosphonic acid monitored.

The hydroformylation reaction was conducted by charging about 770 mL of a catalyst precursor solution of rhodium dicarbonyl acetylacetonate (about 300 ppm rhodium), about 2.0 wt. % 1,1'-biphenyl-2,2'-diyl-(2,6-di-tert-butyl-4-methylphenyl)phosphite ligand (about 15.8 mole equivalents of ligand per mole of rhodium) and about 98 wt. % of $C_5$ aldehyde (about 70 wt % valeraldehyde and about 28 wt % valeraldehyde trimer) as solvent to reactor 1. About 900 mililiters of the same catalyst precursor solution was charged to reactor 2. The start-up and operating procedures set forth in Example 10 were employed. In this experiment a purified Amberlyst ® A-21 ion exchange resin bed was employed from the start of the process. Said bed was situated in the catalyst recycle line so that the recycled rhodium catalyst containing liquid reaction medium after removal of the desired aldehyde product passed through said bed on its return to the reactor. On day 1 of the process an additional amount of the same phosphite ligand was added to make up for the low concentration in the original charge. On day 7 the Amberlyst resin bed was replaced with a new purified Amberlyst-®A-21 ion exchange resin bed. On day 8 the system was shut down for two hours due to a power failure. On day 14 the rhodium complex catalysts were removed from both reactors because reactor liquid level control indications appeared erroneous. On day 15 fresh rhodium dicarbonyl acetylacetonate was added to raise the reaction rate and an additional amount of the same phosphite ligand employed was added to maintain target concentration.

The hydroformylation reaction conditions as well as the rate of $C_5$ aldehydes produced in terms of gram moles per liter per hour and the linear to branched aldehyde product ratio of n-valeraldehyde to 2-methylbutyraldehyde are given in TABLE 22 below.

TABLE 22

| Days of Operation | 7 | 16 | 22 |
|---|---|---|---|
| Butene Feed, mol % | | | |
| Butene-1 | 42.6 | 46.1 | 43.5 |
| Trans-Butene-2 | 34.6 | 30.5 | 32.5 |

TABLE 22-continued

| Days of Operation | 7 | 16 | 22 |
|---|---|---|---|
| Cis-Butene-2 | 22.8 | 23.3 | 24.0 |
| Reactor No. 1 | | | |
| Temperature, °C. | 85 | 85.5 | 85.4 |
| Pressure, psia | 205 | 205 | 205 |
| H₂, psia | 86.4 | 93.1 | 87.1 |
| CO, psia | 27.5 | 8.1 | 12.7 |
| Butene-1, psia | 6.8 | 6.4 | 7.3 |
| Trans-Butene 2 and | 52.6 | 56.8 | 61.2 |
| Cis-Butene-2, psia | | | |
| Reactor No. 2 | | | |
| Temperature, °C. | 95.2 | 95.3 | 96.7 |
| Pressure, psia | 185 | 185 | 185 |
| H₂, psia | 78.2 | 70.7 | 69.0 |
| CO, psia | 15.1 | 15.0 | 16.0 |
| Butene-1, psia | 2.7 | 3.6 | 3.8 |
| Trans-Butene-2 and | 53.0 | 66.6 | 70.1 |
| Cis-Butene-2, psia | | | |
| Results | | | |
| C₅ Aldehydes, gmol/L/hr | 3.31 | 3.15 | 3.01 |
| Linear/Branched Aldehyde Ratio | 1.59 | 1.91 | 1.81 |

During this hydroformylation experiment the hydroformylation reaction medium was monitored for alphahydroxypentyl phosphonic acid via the same $^{31}P$ NMR procedure of Example 23. $^{31}P$ NMR spectra of samples of the hydroformylation reaction medium taken from reactor 1 on days 7, 16 and 22 of the continuous process showed no detectable amounts of alphahydroxypentyl phosphonic acid decomposition product. Moreover, in this experiment the commercial grade Amberlyst ®A-21 ion exchange resin bed was purified before use via a series of elution washings to remove contaminate chlorides and aluminum oxy polymers (oligomers). The purification of the resin was conducted as follows. A 250 gram (630 mL) portion of the resin was charged to a 50 cm×36 mm glass column equipped with a stopcock and containing a glass wool plug. The resin was washed with the following solvents at the given rate of bed volumes per hour: (a) three bed volumes (1890 mL) of 10% aqueous HCl; (b) four bed volumes (2520 mL) of 5% aqueous NaOH; (c) five bed volumes (3150 mL) of deionized water; (d) four bed volumes (2520 mL) of methanol and (e) three bed volumes (1890 mL) of toluene. The resin was then discharged from the column to a one-liter flask and dried at about 40° C. and 10 mm Hg pressure using a rotary evaporator. It is noteworthy that no chloride-rhodium complexes showed up on the $^{31}P$ NMR spectra of this experiment which employed the purified Amberlyst-®A-21 resin.

EXAMPLE 25

The ligand 2-t-butyl-4-methoxyphenyl(3,3'-di-t-butyl-5,5'-dimethoxy-1,1'-biphenyl-2,2'diyl]phosphite having the formula

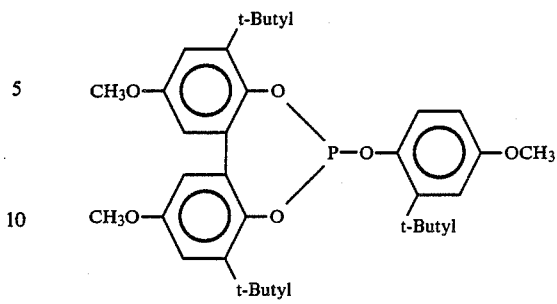

was prepared in the following manner.

About 240 grams of the 2,2'-dihydroxy-3,3'-di-t-butyl-5,5'-dimethoxy-1,1'-biphenyl prepared in the same manner as described in Example 16 was added to about 2.35 liters of toluene. Sufficient toluene was then removed azeotropically to remove residual traces of moisture from the solution. The diol-toluene solution was then cooled to 0° C. and about 314 grams of triethylamine added followed by the dropwise addition of about 92 grams of phosphorous trichloride in 0.5 liters of toluene at 0° C. over about 20 minutes. The reaction solution became thick with triethylamine hydrochloride salt and was brought to room temperature. To this suspension was added a solution of 132.7 grams of 2-t-butyl-4-methoxyphenol in 200 ml. of toluene and the reaction medium refluxed for one 1½ hour. The reaction medium was then filtered hot to remove the solid triethylamine hydrochloride precipitate and the filtrate evaporated to dryness under vacuum. The recovered residue was then dissolved in about 700 ml. of refluxing acetonitrile and cooled to precipitate the desired 2-t-butyl-4-methoxyphenyl(3,3'-di-t-butyl-5,5'-dimethoxy-1,1'-biphenyl-2,2'diyl]phosphite ligand, about 267.5 grams (70.5% of theory) of which was recovered. The desired crystalline, solid phosphite ligand product was found to have a melting point of about 147°–150° C. and a characteristic $^{31}P$ NMR resonance of 139.5 ppm (relative to external $H_3PO_4$).

EXAMPLE 26

A similar continuous hydroformylation experiment as set forth in Example 10 was carried out using a mixed olefin feed of butene-1 and butene-2 (cis and trans), and 2-t-butyl-4-methoxyphenyl(3,3'-di-t-butyl-5,5'-dimethoxy-1,1'-biphenyl-2,2'diyl]phosphite as the ligand promoter. The start-up and general operating procedures set forth in Example 10 were employed.

The hydroformylation reaction was conducted by charging about 1.03 liters of a catalyst precursor solution of rhodium dicarbonyl acetylacetonate (about 158 ppm rhodium), about 3.6 wt.% 2-t-butyl-4-methoxyphenyl(3,3'-di-t-butyl-5,5'-dimethoxy-1,1'-biphenyl-2,2'diyl)phosphite ligand (about 41.5 mole equivalents of ligand per mole of rhodium), and about 96.4 wt.% of C₅ aldehyde (about 76.4 wt.% valeraldehyde and about 20 wt.% valeraldehyde trimer) as solvent to reactor 1. About 1.2 liters of the same catalyst precursor solution was charged to reactor 2.

The hydroformylation reaction conditions as well as the rate of $C_5$ aldehydes produced in gram moles per liter per hour and the linear n-valeraldehyde to branched 2-methylbutyraldehyde product ratio over 5 days of continuous hydroformylation is set forth in Table 23 below. The aldehyde was separated from the liquid reaction solution at about 107° to 109° C. and about 18 psi and no rhodium loss was observed over said 5 days of continuous hydroformylation.

TABLE 23

| Days of Operation | 1 | 5 |
|---|---|---|
| Butene Feed, mol % | | |
| Butene-1 | 5.4 | 5.4 |
| Trans-Butene-2 | 50.5 | 50.6 |
| Cis-Butene-2 | 43.9 | 43.8 |
| n-Butane | 0.2 | 0.2 |
| Reactor No. 1 | | |
| Temperature, °C. | 80.1 | 80.2 |
| Pressure, psia | 185 | 185 |
| H₂, psia | 63.4 | 50.8 |
| CO, psia | 80.1 | 70.6 |
| Butene-1, psia | 0.2 | 0.4 |
| Butene-2 (cis and trans), psia | 20.4 | 30.0 |
| Reactor No. 2 | | |
| Temperature, °C. | 85.3 | 85.3 |
| Pressure, psia | 165 | 165 |
| H₂, psia | 28 | 15.2 |
| CO, psia | 64.6 | 65.0 |
| Butene-1, psia | 0.1 | 0.4 |
| Butene-2 (cis and trans), psia | 8.4 | 13.6 |
| Results | | |
| C₅ Aldehydes, gmols/L/Hr. | 1.98 | 1.90 |
| Linear/Branched Aldehyde Ratio | 0.31 | 0.33 |

EXAMPLE 27

A similar continuous hydroformylation experiment as set forth in Example 10 was carried out having a mixed olefin feed of butene-1 and butene-2 (cis and trans), and 2-t-butyl-4-methoxyphenyl(3,3'-di-t-butyl-5,5'-dimethoxy-1,1'-biphenyl-2,2'-diyl)phosphite as the ligand promoter. The start-up and general operating procedures set forth in Example 10 were employed.

The hydroformylation reaction was conducted by charging about 1.03 liters of a catalyst precursor solution of rhodium dicarbonyl acetylacetonate (about 155 ppm rhodium), about 3.4 wt.% 2-t-butyl-4-methoxyphenyl(3,3'-di-t-butyl-5,5'-dimethoxy-1,1'-biphenyl-2,2'diyl)phosphite ligand (about 39.9 mole equivalents of ligand per mole of rhodium), about 1% vinyl pyrrolidone-vinyl acetate copolymer, and about 95.6 wt.% of $C_5$ aldehyde (about 86.2 wt.% valeraldehyde and about 9.4 wt.% valeraldehyde trimer) as solvent to reactor 1. About 1.2 liters of the same catalyst precursor solution was charged to reactor 2.

The hydroformylation reaction conditions as well as the rate of $C_5$ aldehydes produced in gram moles per liter per hour and the linear n-valeraldehyde to branched 2-methylbutyraldehyde product ratio over 31 days of continuous hydroformylation is set forth in Table 24 below. The aldehyde was separated from the liquid reaction solution at about 106° to 110° C. and 18-21 psi and no rhodium loss was observed over said 31 days of continuous hydroformylation.

TABLE 24

| Days of Operation | 6.9 | 13.9 | 20.9 | 30.8 |
|---|---|---|---|---|
| Butene Feed, mol % | | | | |
| Butene-1 | 5.6 | 5.4 | 5.3 | 5.4 |
| Butene-2 (cis and trans), psia | 94.2 | 91.5 | 91.2 | 90.2 |
| n-Butane | 0.2 | 3.1 | 3.5 | 4.4 |
| Reactor No. 1 | | | | |
| Temperature, °C. | 80.4 | 80.4 | 80.4 | 80.5 |
| Pressure, psia | 185 | 185 | 185 | 185 |
| H₂, psia | 65.2 | 68.2 | 61.3 | 65.2 |
| CO, psia | 75.5 | 71.9 | 68.5 | 66.5 |
| Butene-1, psia | 0.5 | 0.4 | 0.4 | 0.4 |
| Butene-2 (cis and trans), psia | 31.1 | 30.0 | 30.9 | 30.3 |
| Reactor No. 2 | | | | |
| Temperature, °C. | 85.0 | 85.0 | 85.3 | 85.4 |
| Pressure, psia | 165 | 165 | 165 | 165 |
| H₂, psia | 49.9 | 56.2 | 53.9 | 59.0 |
| CO, psia | 71.9 | 66.5 | 66.6 | 63.7 |
| Butene-1, psia | 0.2 | 0.2 | 0.4 | 0.2 |
| Butene-2 (cis and trans), psia | 14.3 | 12.8 | 12.1 | 12.5 |
| Results | | | | |
| n-Valeraldehyde | 0.40 | 0.38 | 0.38 | 0.37 |
| 2-Methylbutyraldehyde (g mol/L/hr) | 1.31 | 1.23 | 1.25 | 1.21 |

EXAMPLE 28

The hydrolytic stabilities of various diorganophosphite ligands of the general formula

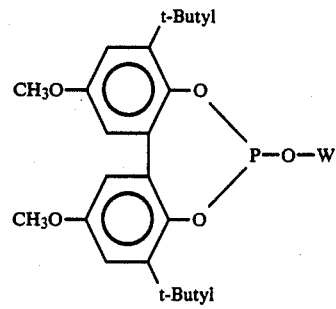

were tested as follows:

A 2 oz. bottle equipped with a magnetic stirring bar and capped with a serum stopper was charged with 10 gm Texanol ®. The solvent was degassed by stirring it while evacuating the bottle and refilling with nitrogen three times, 0.97 mmol of a diorganophosphite ligand and 0.01 gm 1-hydroxypentyl phosphonic acid were added under a stream of nitrogen, and the solution was again degassed by evacuating the bottle and refilling with nitrogen three times. When the diorganophosphite dissolved, the solution was transferred via syringe to a nitrogen flushed glass pressure bottle, and capped by a nitrogen flushed gas manifold. The bottle was attached to a source of pressurized nitrogen and purged by pressurizing to 60 psig and venting and repeating this three times. The bottle was finally pressurized to 20 psig with nitrogen and placed in an oil bath maintained at the temperature indicated in the table.

The extent of ligand decomposition was determined by analysis of the reaction by high performance liquid chromatography, and the extent of ligand decomposition as a result of acid catalyzed hydrolysis is given in terms of the percentage of ligand decomposed after the indicated number of hours of reaction relative to the the amount present at the initiation of reaction in Table 25 below.

TABLE 25

| Run No. | W | T (°C.) | Hours | Extent of Decomposition (%) |
|---|---|---|---|---|
| 1 | Methyl | 120 | 7 | 100 |
| 2 | 2,4-Dimethyl phenyl | 100 | 68 | 69 |
| 3 | 2-tert-butyl-4-methoxyphenyl | 100 | 68 | 13 |

EXAMPLE 29

The transesterification stabilities of various diorganophosphite ligands of the general formula

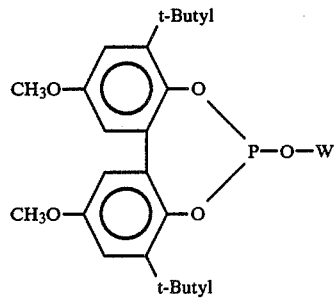

were tested as follows:

A 2 oz. bottle equipped with a magnetic stirring bar and capped with a serum stopper was charged with 10 gm Texanol ®. The solvent was degassed by stirring it while evacuating the bottle and refilling with nitrogen three times, 0.97 mmol of the indicated diorganophosphite ligand and 0.197 gm of [3,3'-di-t-butyl-5,5'-dimethoxy-1,1'-biphenyl-2,2'-diyl]hydrogen phosphite were added under a stream of nitrogen, and the solution was again degassed by evacuating the bottle and refilling with nitrogen three times. When the diorganophosphite dissolved, the solution was transferred via syringe to a nitrogen flushed glass pressure bottle, and capped by a nitrogen flushed gas manifold. The bottle was attached to a source of pressurized nitrogen and purged by pressurizing to 60 psig and venting and repeating this three times. The bottle was finally pressurized to 20 psig with nitrogen and placed in an oil bath maintained at 120 C°.

The extent of ligand decomposition was determined by analysis of the reaction by high performance liquid chromatography, and the extent of ligand decomposition as a result of transesterification is given in terms of the percentage of ligand decomposed after the indicated number of hours of reaction relative to the amount present at the initiation of reaction in Table 26 below.

TABLE 26

| Run No. | W | Hours | Extent of Decomposition (%) |
|---|---|---|---|
| 1 | Methyl | 6 | 93 |
| 2 | 2-tert-butyl-4-methoxyphenyl | 19 | 0 |

Various modifications and variations of this invention will be obvious to a worker skilled in the art and it is to be understood that such modifications and variations are to be included within the purview of this application and the spirit and scope of the appended claims.

We claim:

1. A hydroformylation process for producing aldehydes which comprises reacting an olefinically unsaturated organic compound with carbon monoxide and hydrogen in the presence of a rhodium complex catalyst consisting essentially of rhodium complexed with carbon monoxide and a diorganophosphite ligand, and in the added presence of a free diorganophosphite ligand, wherein the diorganophosphite ligand complexed with the rhodium and the free diorganophosphite ligand are each individually ligands having the formula

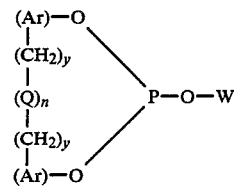

wherein W represents an unsubstituted or substituted monovalent hydrocarbon radical; wherein each Ar group represents an identical or different substituted or unsubstituted aryl radial, wherein each y individually has a value of 0 to 1, wherein Q is a divalent bridging group selected from the class consisting of $-CR^1R^2-$, $-O-$, $-S-$, $-NR^3-$, $-SiR^4R^5-$ and $-CO-$, wherein each $R^1$ and $R^2$ radical individually represents a radical selected from the group consisting of hydrogen, alkyl of 1 to 12 carbon atoms, phenyl, tolyl and anisyl, wherein each $R^3$, $R^4$, and $R^5$ radical individually represents $-H$ or $-CH_3$, and wherein n has a value of 0 to 1, and wherein the hydroformylation reaction conditions comprise a reaction temperature in the range of from about 45° C. to about 200° C., to a total gas pressure of hydrogen, carbon monoxide and olefinically unsaturated organic compound of from about 1 to about 10,000 psia, a $H_2$:CO molar ratio of gaseous hydrogen to carbon monoxide in the range of from about 1:10 to 100:1, and wherein the reaction medium contains at least one mole of free diorganophosphite ligand per mole of rhodium present in the reaction medium.

2. A process as defined in claim 1 wherein the diorganophosphite ligand complexed with the rhodium and the free diorganophosphite ligand are each individually ligands as defined by Formula (III), wherein $X^1$, $Y^1$ and $Y^2$ each represent a radical having a steric hindrance of isopropyl or greater and wherein $X^2$ represents a hydrogen radical.

3. A process as defined in claim 2, wherein $X^1$, $Y^1$ and $Y^2$ are branched chain alkyl radicals having from 3 to 5 carbon atoms, wherein Q is $-CH_2-$ or $-CHCH_3-$, and wherein $Z^2$ and $Z^3$ each individually represent a radical selected from the group consisting of hydroxy and an alkoxy radical $-OR^6$, wherein $R^6$ represents a substituted or unsubstituted monovalent hydrocarbon radical.

4. A process as defined in claim 3, wherein n is zero, wherein $Z^2$ and $Z^3$ are methoxy radicals and wherein $X^1$, $Y^1$ and $Y^2$ are t-butyl radicals.

5. A process as defined in claim 4, wherein $Z^1$ is a methoxy radical.

6. A process as defined in claim 2, wherein $Y^1$ and $Y^2$ are radicals having a steric hindrance of isopropyl or greater and wherein W represents an aryl radical of the formula

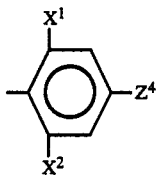

wherein $X^1$ represents a radical having a steric hindrance of isopropyl or greater, and wherein $X^2$ is hydrogen.

7. A process as defined in claim 6, wherein $Z^2$ and $Z^3$ each represent a methoxy radical, wherein $X^1$, $Y^1$ and $Y^2$ each represent a tertiary butyl radical and wherein n is zero.

8. A process as defined in claim 7, wherein $Z^4$ is a methoxy radical.

9. A process as defined in claim 4, wherein the olefin starting material is an olefin mixture consisting essentially of butene-1 and butene-2.

10. A process as defined in claim 9, wherein the hydroformylation comprises a continuous liquid catalyst recycle procedure.

11. A hydroformylation process as defined in claim 1, wherein the olefinically unsaturated compound is selected from the group consisting of alpha-olefins containing from 2 to 20 carbon atoms, internal olefins containing from 4 to 20 carbon atoms, and mixtures of such alpha and internal olefins.

12. A process as defined in claim 11 wherein the hydroformylation reaction conditions comprise, a reaction temperature in the range of from about 50° C. to 120° C., a total gas pressure of hydrogen, carbon monoxide and olefinically unsaturated organic compound of from about 1 to about 1500 psia., a hydrogen partial pressure of from about 15 to about 160 psia., a carbon monoxide partial pressure of from about 1 to about 120 psia., and wherein the reaction medium contains from about 4 to about 50 moles of said diorganophosphite ligand per mole of rhodium in said medium.

13. A process as defined in claim 12 wherein the diorganophosphite ligand complexed with the rhodium and the free diorganophosphite ligand also present are each individually ligands having the formula

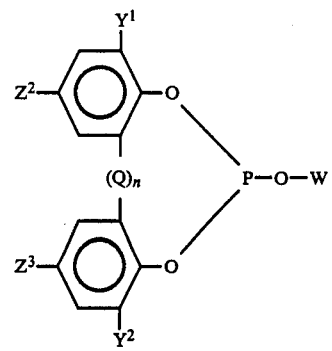

wherein Q is $-CR^1R^2$ wherein each $R^1$ and $R^2$ radical individually represents a radical selected from the group consisting of hydrogen, alkyl of 1 to 12 carbon atoms, phenyl, tolyl and anisyl, and n has a value of 0 to 1; wherein each $Y^1$, $Y^2$, $Z^2$, and $Z^3$ group individually represents a radical selected from the group consisting of hydrogen, an alkyl radical having from 1 to 18 carbon atoms, substituted or unsubstituted aryl, alkaryl, aralkyl and alicyclic radicals, cyano, halogen, nitro, trifluoromethyl, hydroxy, carbonyloxy, amino, acyl, phosphonyl, oxycarbonyl, amido, sulfinyl, sulfonyl, silyl, ether, and thionyl radicals with the proviso that both $Y^1$ and $Y^2$ are radicals having a steric hindrance of isopropyl or greater, and wherein W represents a substituted or unsubstituted alkyl radical.

14. A process as defined in claim 13, wherein the olefin starting material is selected from the group consisting of butene-1, butene-2, isobutylene, and an olefin mixture consisting essentially of butene-1 and butene-2, wherein Q is $-CH_2-$ or $-CHCH_3-$, wherein $Y^1$ and $Y^2$ are branched alkyl radicals having from 3 to 5 carbon atoms and wherein W is an unsubstituted alkyl radical having from 1 to 10 carbon atoms.

15. A process as defined in claim 14 wherein $Y^1$ and $Y^2$ are t-butyl radicals, Q is $-CH_2-$ and wherein W is an unsubstituted alkyl radical having from 1 to 8 carbon atoms.

16. A process as defined in claim 14, wherein $Y^1$ and $Y^2$ are t-butyl radicals, Q is $-CH_2-$ and wherein W is a phosphonyl substituted alkyl radical of the formula

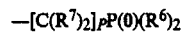

$$-[C(R^7)_2]_pP(O)(R^6)_2$$

wherein each $R^6$ is the same or different and is individually selected from the group consisting of alkyl, phenyl and cyclohexyl radicals, wherein each $R^7$ is the same or different and is individually selected from the group consisting of hydrogen and alkyl radicals having from 1 to 4 carbon atoms and wherein p has a value of 1 to 10, with the proviso that one $R^6$ radical can also be hydrogen.

17. A process as defined in claim 16, wherein W is a $-CH_2CH_2P(O)(C_6H_5)_2$ radical.

18. A process as defined in claim 12, wherein the diorganophosphite ligand complexed with the rhodium and the free diorganophosphite ligand also present are each individually ligands having a formula selected from the group consisting of

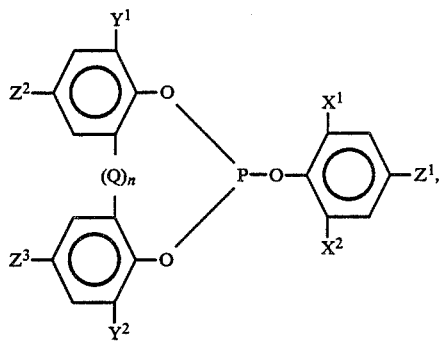
(III)

and

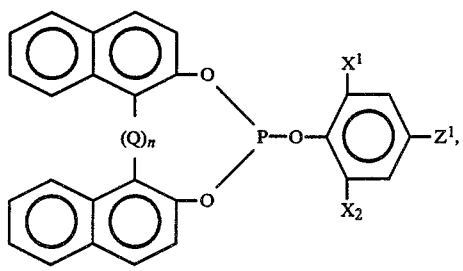
(IV)

wherein Q is —$CR^1R^2$ wherein each $R^1$ and $R^2$ radical individually represents a radical selected from the group consisting of hydrogen, alkyl of 1 to 12 carbon atoms, phenyl, tolyl and anisyl, and n has a value of 0 to 1; wherein each $X^1$, $X^2$, $Y^1$, $Y^2$, $Z^1$, $Z^2$, and $Z^3$ group individually represents a radical selected from the group consisting of hydrogen, an alkyl radical having from 1 to 18 carbon atoms, substituted or unsubstituted aryl, alkaryl, aralkyl and alicyclic radicals above (e.g. phenyl, benzyl, cyclohexyl, 1-methylcyclohexyl, and the like), cyano, halogen, nitro, trifluoromethyl, hydroxy, amino, acyl, carbonyloxy, oxycarbonyl, amido, sulfonyl, sulfinyl, silyl, ether, phosphonyl, and thionyl radicals, with the proviso that at least both of the $X^1$ and $X^2$ groups or at least both of the $Y^1$ and $Y^2$ groups on a given diorganophosphite of Formulas (III) and (IV) above are radicals having a steric hindrance of isopropyl, or greater, and with the proviso that in Formula (III) above no more than three of the $X^1$, $X^2$, $Y^1$, or $Y^2$ groups is a radical having a steric hindrance of iospropyl or greater at the same time.

19. A process as defined in claim 18 wherein Q is —$CH_2$— or —$CHCH_3$— and wherein $Y^1$ and $Y^2$ are branched chain alkyl radicals having from 3 to 5 carbon atoms.

20. A process as defined in claim 19 wherein the olefin starting material is selected from the group consisting of butene-1, butene-2, isobutylene and an olefin mixture consisting essentially of butene-1 and butene-2, wherein Q is —$CH_2$— and wherein each $X^1$, $X^2$, $Y^1$, $Y^2$, $Z^1$, $Z^2$, and $Z^3$ group individually represents a radical selected from the group consisting of hydrogen, an alkyl radical having from 1 to 8 carbon atoms, cyano, halogen, nitro, trifluoromethyl, hydroxy, amino, acyl, carbonyloxy, oxycarbonyl, amido, sulfonyl, sulfinyl, silyl, ether, phosphonyl and thionyl radicals.

21. A process as defined in claim 20 wherein the diorganophosphite ligand is selected from the group consisting of

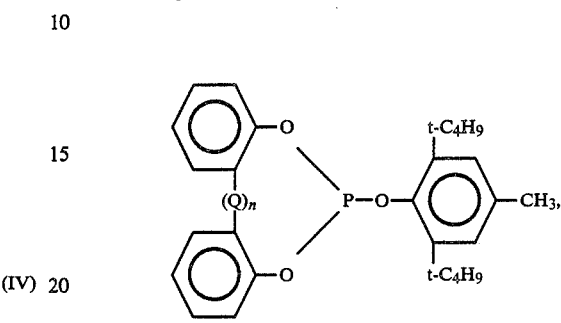

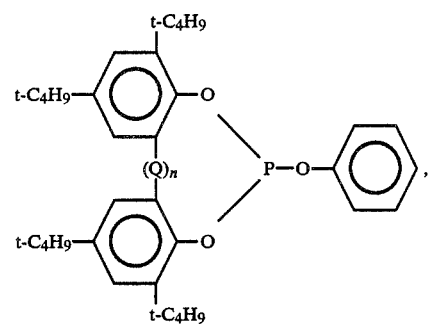

and

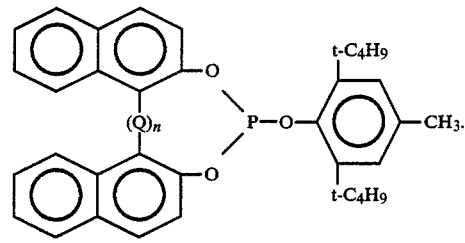

22. A process as defined in claim 21 wherein the olefin starting material is an olefin mixture consisting essentially of butene-1 and butene-2.

23. A process as defined in claim 22, wherein the hydroformylation comprises a continuous catalyst containing liquid recycle procedure.

24. A process as defined in claim 11 wherein the diorganophosphite complexed with the rhodium and the free diorganophosphite ligand also present are each individually ligands having the formula

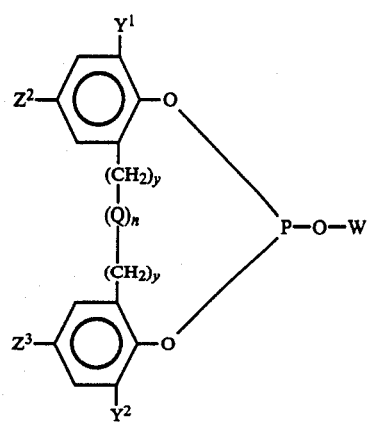

wherein $Z^2$ and $Z^3$ each individually represent a radical selected from the group consisting of hydroxy and an oxy radical —$OR^6$, wherein $R^6$ represents a substituted or unsubstituted monovalent hydrocarbon radical; wherein $Y^1$ and $Y^2$ each individually represents a radical selected from the group consisting of hydrogen, an alkyl radical having from 1 to 8 carbon atoms, substituted or unsubstituted aryl, alkaryl, and alicyclic radicals; wherein W represents a substituted or unsubstituted monovalent hydrocarbon radical; wherein each v individually has a value of 0 to 1, wherein Q is a divalent bridging group selected from the class consisting of —$CR^1R^2$, —O—, —S—, —$NR^3$—, —$SiR^4R^5$— and —CO—, wherein each $R^1$ and $R^2$, radical individually represents a radical selected from the group consisting of hydrogen, alkyl of 1 to 12 carbon atoms, phenyl, tolyl and anisyl, wherein each $R^3$, $R^4$, and $R^5$ radical individually represents —H or —$CH_3$, and wherein n has a value of 0 or 1.

25. A process as defined in claim 24 wherein each y has a value of zero, wherein Q is —$CH_2$— or —$CHCH_3$—; wherein $R^6$ is an alkyl radical of 1 to 10 carbon atoms; wherein $Y^1$ and $Y^2$ each individually represent a radical selected from the group consisting of hydrogen, branched chain alkyl radicals having from 3 to 12 carbon atoms, phenyl, benzyl, cyclohexyl and 1-methylcyclohexyl; and wherein W represents a radical selected from the group consisting of an alkyl radical of 1 to 18 carbon atoms, alpha-naphthyl, beta-naphthyl, and an aryl radical of the formula

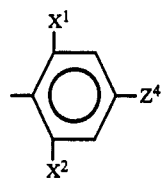

wherein $X^1$, $X^2$ and $Z^4$ each individually represent a radical selected from the group consisting of hydrogen, an alkyl radical having from 1 to 18 carbon atoms, substituted and unsubstituted aryl, alkaryl, aralkyl and alicyclic radicals, cyano, halogen, nitro, trifluoromethyl, hydroxy, amino, acyl, carbonyloxy, oxycarbonyl, amido, sulfonyl, sulfinyl, silyl, ether, phosphonyl, and thionyl radicals, with the proviso that at least both of the $X^1$ and $X^2$ groups or at least both of the $Y^1$ and $Y^2$ groups on a given diorganophosphite ligand are radicals having a steric hinderance of isopropyl, or greater, and with the proviso that no more than three of the $X^1$, $X^2$, $Y^1$ or $Y^2$ groups is a radical having a steric hinderance of isopropyl or greater at the same time.

26. A process as defined in claim 25 wherein $Z^2$ and $Z^3$ each represent a —$OR^6$ radical wherein $R^6$ is an alkyl of 1 to 10 carbon atoms, wherein $Y^1$ and $Y^2$ are both branched chain alkyl radicals of 3 to 5 carbon atoms and wherein W is an alkyl radical of 1 to 10 carbon atoms.

27. A process as defined in claim 26 wherein $Z^2$ and $Z^3$ each represent a methoxy radical, wherein $Y^1$ and $Y^2$ each represent a tertiary butyl radical, and wherein W represents a methyl radical.

28. A process as defined in claim 26 wherein q is zero.

29. A process as defined in claim 11 wherein the hydroformylation comprises a continuous catalyst containing liquid recycle procedure.

30. A process as defined in claim 11 which comprises minimizing decomposition of the free diorganophosphite ligand by (a) removing a portion of the liquid hydroformylation reaction medium from the hydroformylation reaction zone, (b) treating the liquid medium so removed with a weakly basic anion exchange resin and (c) returning the treated reaction medium to the hydroformylation reaction zone.

31. A process as defined in claim 28, wherein the hydroformylation comprises a continuous catalyst containing liquid recycle procedure.

32. A process as defined in claim 29 which comprises removing a portion liquid hydroformylation reaction medium from the hydroformylation reaction zone and passing said medium, either prior to and/or after separation of aldehyde product therefrom, through a weakly basic anion exchange resin bed.

33. A process as defined in claim 30, wherein said weakly basic anion exchange resin comprises a crosslinked tertiary amine polystyrene anion exchange resin of the gel or macroreticular type.

* * * * *